United States Patent
Muratoglu et al.

(10) Patent No.: US 8,426,486 B2
(45) Date of Patent: *Apr. 23, 2013

(54) HIGHLY CRYSTALLINE CROSS-LINKED OXIDATION-RESISTANT POLYETHYLENE

(75) Inventors: Orhun K. Muratoglu, Cambridge, MA (US); Ebru Oral, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 997 days.

This patent is subject to a terminal disclaimer.

(21) Appl. No.: 10/597,652

(22) PCT Filed: Feb. 3, 2005

(86) PCT No.: PCT/US2005/003305
§ 371 (c)(1), (2), (4) Date: Mar. 14, 2007

(87) PCT Pub. No.: WO2005/074619
PCT Pub. Date: Aug. 18, 2005

(65) Prior Publication Data
US 2007/0265369 A1    Nov. 15, 2007

Related U.S. Application Data
(60) Provisional application No. 60/541,073, filed on Feb. 3, 2004.

(51) Int. Cl.
*B29C 35/08* (2006.01)
*H05B 6/00* (2006.01)
*B28B 5/00* (2006.01)
*A61F 2/02* (2006.01)

(52) U.S. Cl.
USPC ........ 522/157; 264/241; 264/488; 623/16.11; 424/423; 424/486; 523/113; 523/115

(58) Field of Classification Search .................. 522/157, 522/161; 264/479, 241, 488; 623/16.11; 424/423, 486; 523/113, 115
See application file for complete search history.

(56) References Cited

U.S. PATENT DOCUMENTS

| | | | |
|---|---|---|---|
| 5,827,904 A | 10/1998 | Hahn | ............................. 523/113 |
| 5,879,400 A * | 3/1999 | Merrill et al. | .............. 623/22.11 |

(Continued)

FOREIGN PATENT DOCUMENTS

| | | |
|---|---|---|
| JP | 07-502290 | 3/1995 |
| JP | 2003-530957 | 10/2003 |

(Continued)

OTHER PUBLICATIONS

Wolf, C.; Lederer, K.; Bergmeister, H.; Losert, U.; Böck, P. J. Mat. Sci.: Mat in Med, 2006, 17, 1341-1347; Springer Science + Business Media, LLC 2006.*

(Continued)

*Primary Examiner* — Michael Pepitone
(74) *Attorney, Agent, or Firm* — Perkins Coie LLP

(57) ABSTRACT

The present invention relates to methods for making highly crystalline cross-linked polymeric material, for example, highly crystalline cross-linked ultra-high molecular weight polyethylene (UHMWPE). The invention also provides methods of making antioxidant-doped highly crystalline cross-linked polymeric material using high pressure and high temperature crystallization processes, medical implants made thereof, and materials used therein.

50 Claims, 17 Drawing Sheets

U.S. PATENT DOCUMENTS

| | | | |
|---|---|---|---|
| 6,448,315 B1 * | 9/2002 | Lidgren et al. | 524/110 |
| 6,517,857 B2 | 2/2003 | Ylänen et al. | 424/422 |
| 6,562,540 B2 | 5/2003 | Saum et al. | |
| 6,620,198 B2 | 9/2003 | Burstein et al. | 623/20.28 |
| 6,641,617 B1 | 11/2003 | Merrill et al. | |
| 6,852,772 B2 | 2/2005 | Muratoglu et al. | |
| 7,431,874 B2 | 10/2008 | Muratoglu et al. | |
| 2002/0107300 A1 * | 8/2002 | Saum et al. | 522/161 |
| 2002/0125614 A1 * | 9/2002 | King et al. | 264/488 |
| 2003/0149125 A1 * | 8/2003 | Muratoglu et al. | 522/150 |
| 2004/0156879 A1 | 8/2004 | Muratoglu et al. | |
| 2005/0146070 A1 | 7/2005 | Muratoglu et al. | |
| 2007/0267030 A1 | 11/2007 | Muratoglu et al. | |

FOREIGN PATENT DOCUMENTS

| | | |
|---|---|---|
| WO | WO 93/10953 | 6/1993 |
| WO | WO97/29793 | 8/1997 |
| WO | WO 9952474 A1 * | 10/1999 |
| WO | WO01/05337 | 1/2001 |
| WO | WO 01/80778 | 11/2001 |
| WO | WO 03/059220 | 7/2003 |
| WO | WO2004/000159 | 12/2003 |
| WO | WO2004/064618 | 8/2004 |
| WO | WO2005/074619 | 8/2005 |

OTHER PUBLICATIONS

Baker et al., Polymer 41: 795-808 (2000).
Kurtz et al., Biomaterials 20(18): 1659-1688 (1999).
Collier et al., The Journal of Anthroplasty 11(4): 377-389 (1996).
McKellop et al., Journal of Orthopaedic Research 17: 157-167 (1999).
Muratoglu et al., Biomaterials 20: 1463-1470 (1999).
Muratoglu et al., The Journal of Anthroplasty 16(2): 149-160 (2001).
Parth et al., Journal of Materials Science: Materials in Medicine 13: 917-921 (2002).
Wunderlich et al., Journal of Polymer Science: Part A-2, vol. 7: 2043-2050 (1969).
Bassett et al., J Appl. Phys. 45(10): 4146-4150 (1974).
Bistolfi et al., 51st Annual Meeting of the Orthopaedic Research Society, Paper No. 0240 (Morphological, Tensile and Wear Properties of High Crystallinity Crosslinked UHMWPE).
McCrum et al., Anelastic and Dielectric Effects in Polymeric Solids, Molecular Theories of Relaxation, pp. 141-145 (1967).
Oral et al., 51st Annual Meeting of the Orthopaedic Reserach Society, Poster No. 0988 (High-Pressure Crystallized, Irradiated and α-Tocopherol-Stabilized UHMWPE with High Biomaterials 26: 6657-6663 (2005).
Pruitt et al., 50th Annual Meeting of the Orthopaedic Research Society (Poster No: 1471) Fatigue Behavior of Crosslinked UHMWPE with High Crystallinity.
Wolf et al., Journal of Materials Science: Materials in Medicine 13: 701-705 (2002).

* cited by examiner (a)

(b)

HIGHLY CRYSTALLINE CROSS-LINKED OXIDATION-RESISTANT POLYETHYLENE

This application is a national stage of PCT/US2005/003305 filed Feb. 3, 2005, which claims priority to Provisional Application No. 60/541,073 filed Feb. 3, 2004. The entirety of which are hereby incorporated by reference.

FIELD OF THE INVENTION

The present invention relates to methods for making crystalline oxidation-resistant cross-linked polymeric materials, including highly crystalline oxidation-resistant cross-linked polymeric materials. Methods of crystallizing cross-linked polymeric materials under high pressure at elevated temperature and materials used therewith also are provided.

BACKGROUND OF THE INVENTION

Total joint arthroplasty for end-stage joint diseases most commonly involves a metal/polymer articular pair. Polyethylene, particularly ultrahigh molecular weight polyethylene (UHMWPE), has been and remains the material of choice for the load-bearing, articulating surface for this articular pair for more than four decades (Kurtz, et al., Biomaterials, 1999. 20(18): p. 1659-1688). Despite high long-term success rates for such reconstructions, wear and fatigue damage of polyethylene limit the longevity of total joints. In total knees, implant failure is caused primarily by fatigue damage to the polyethylene components (Collier, et al., J. Arthroplasty, 1996. 11(4): p. 377-389). One solution to prevent osteolysis in total hips is cross-linking, which markedly reduces polyethylene wear (Muratoglu, et al., J Arthroplasty, 2001. 16(2): p. 149-160; Muratoglu, et al., Biomaterials, 1999. 20(16): p. 1463-1470; McKellop, et al., J Orthop Res, 1999. 17(2): p. 157-167).

Increased crosslink density in polymeric material is desired in bearing surface applications for joint arthroplasty because it significantly increases wear resistance. Oxidation-resistant cross-linked polymeric material, such as UHMWPE, is desired in medical devices because it significantly increases the wear resistance of the devices. A method of cross-linking is by exposing the UHMWPE to ionizing radiation. However, cross-linking also reduces the fatigue strength of polyethylene, therefore limiting the use of highly cross-linked polyethylenes in total knees where the components are subjected to cyclic loading accompanied by high stresses. Ionizing radiation, in addition to cross-linking, also will generate residual free radicals, which are the precursors of oxidation-induced embrittlement. This is known to adversely affect in vivo device performance. Therefore, it is desirable to reduce the concentration of residual free radicals, preferably to undetectable levels, following irradiation to avoid long-term oxidation.

One way of substantially reducing the concentration of residual free radicals in irradiated UHMWPE is to heat the irradiated UHMWPE to above its melting temperature (for example, about 137° C.-140° C.). Melting frees or eliminates the crystalline structure, where the residual free radicals are believed to be trapped. This increase in the free radical mobility facilitates the recombination reactions, through which the residual free radical concentration can be markedly reduced. This technique, while effective at recombining the residual free radicals, has been shown to decrease the final crystallinity of the material. This loss of crystallinity will reduce the modulus of the UHMWPE. Yet for high stress applications, such as unicompartmental knee designs, thin polyethylene tibial knee inserts, low conformity articulations, etc., high modulus is desired to minimize creep.

Cross-linking by irradiation decreases the fatigue strength of UHMWPE. In addition, post-irradiation melting further decreases the fatigue strength of the UHMWPE. Radiation and melting also decrease the yield strength, ultimate tensile strength, toughness and elongation at break of UHMWPE.

Melting in combination with irradiation creates cross-links and facilitates recombination of the residual free radicals trapped mostly in the crystalline regions, which otherwise would cause oxidative embrittlement upon reactions with oxygen. Both cross-linking and melting, however, decrease the crystallinity of UHMWPE. Cross-linking and decrease in the crystallinity is thought to be the reason for decrease in fatigue strength, yield strength, ultimate tensile strength, toughness and elongation at break. Some or all of these changes in properties limit the use of low wear highly cross-linked UHMWPE to low stress applications. Therefore, a cross-linked UHMWPE with higher crystallinity is desirable for low wear and high fatigue resistance for high stress application that require low wear.

It is, therefore, desirable to reduce the irradiation-created residual free radical concentration in cross-linked UHMWPE without reducing crystallinity, so as to achieve high fatigue resistance for high stress application that require low wear. Alternative methods to melting can be used to prevent the long-term oxidation of irradiated UHMWPE to preserve higher levels of crystallinity and fatigue strength.

The effect of crystallinity on the fatigue strength of conventional UHMWPE is known. Investigators increased the crystallinity of unirradiated UHMWPE by high-pressure crystallization, which increased the fatigue crack propagation resistance of unirradiated UHMWPE by about 25% (Baker et al., Polymer, 2000. 41(2): p. 795-808). Others found that under high pressures (2,000-7,000 bars) and high temperatures (>200° C.), polyethylene grows extended chain crystals and achieves a higher crystallinity level (Wunderlich et al., Journal of Polymer Science Part A-2: Polymer Physics, 1969. 7(12): p. 2043-2050). However, high-pressure crystallization of highly cross-linked UHMWPE has not been previously attempted or discussed. Also, the crystallization behavior of highly cross-linked polyethylene at high pressures has not been determined.

Polyethylene undergoes a phase transformation at elevated temperatures and pressures from the orthorhombic to the hexagonal crystalline phase. The hexagonal phase can grow extended chain crystals and result in higher crystallinity in polyethylene. This is believed to be a consequence of less hindered crystallization kinetics in the hexagonal phase compared with the orthorhombic phase. One could further reduce the hindrance on the crystallization kinetics by introducing a plasticizing or a nucleating agent into the polyethylene prior to high-pressure crystallization. The polyethylene can be doped with a plasticizing agent, for example, α-tocopherol or vitamin E, prior to high-pressure crystallization. The doping can be achieved either by blending the polyethylene resin powder with the plasticizing agent and consolidating the blend or by diffusing the plasticizing agent into the consolidated polyethylene. Various processes of doping can be employed as described in U.S. application Ser. No. 10/757,551, filed Jan. 15, 2004, and PCT/US/04/00857, filed Jan. 15, 2004, the entirety of which are hereby incorporated by reference.

SUMMARY OF THE INVENTION

The present invention relates generally to methods of making crystalline oxidation-resistant cross-linked polymeric material, preferably the cross-linked material has higher crystallinity than obtainable with previous methodologies. More specifically, the invention relates to methods of radiation cross-linking highly crystalline UHMWPE and subsequently treating the UHMWPE to increase its oxidation resistance. Also the invention relates to methods of crystallizing cross-linked ultra-high molecular weight polyethylene (UHMWPE) under high pressure at elevated temperature in the hexagonal phase, whereby extended chain crystals are present and high crystallinity are achieved, followed by treating the UHMWPE to increase its oxidation resistance. The invention also relates to methods of crystallizing cross-linked ultra-high molecular weight polyethylene (UHMWPE) under high pressure at elevated temperature in the hexagonal phase where high crystallinity is achieved and the residual free radical population is reduced. Also the invention relates to methods of increasing the crystallinity of oxidation-resistant crosslinked UHMWPE containing no detectable residual free radicals or with a reduced free radical population by high-pressure crystallization.

The process comprises steps of crystallizing polyethylene under high pressure at elevated temperature, irradiating at different temperatures below the melt to control the amount of amorphous, folded and extended chain crystals during cross-linking. This invention also relates to processes to increase oxidation resistance where an antioxidant is incorporated into polyethylene, or a cross-linked polyethylene is mechanically deformed and annealed, or a high pressure and high temperatures are applied to the cross-linked polyethylene. The processes can be used separately or together in various orders in accordance with the teachings herein and the skill in the art. All ranges set forth herein in the summary and description of the invention include all numbers or values thereabout or therebetween of the numbers of the range. The ranges of the invention expressly denominate and set forth all integers and fractional values in the range.

One aspect of the invention provides methods of making highly crystalline cross-linked polymeric material comprising: a) heating a polymeric material to a temperature above the melt; b) pressurizing the heated polymeric material, preferably under a pressure of at least about 10-1000 MPa, preferably at least about 150 MPa, more preferably at least about 250 MPa; c) holding at this pressure; d) cooling the heated polymeric material to about room temperature; e) releasing the pressure to about an atmospheric pressure level, thereby forming a highly crystalline polymeric material; and f) irradiating the highly crystalline polymeric material at a temperature below the melt with ionizing radiation, thereby forming a highly crystalline cross-linked polymeric material.

In another aspect, the invention provides methods of making oxidation-resistant cross-linked polymeric material comprising: a) heating a polymeric material to a temperature above the melt; b) pressurizing the heated polymeric material under at least about 10-1000 MPa, preferably at least about 150 MPa, more preferably at least about 250 MPa; c) holding at this pressure; d) cooling the heated polymeric material to about room temperature; e) releasing the pressure to about an atmospheric pressure level, thereby forming a highly crystalline polymeric material; f) irradiating the highly crystalline polymeric material at temperature below the melt with ionizing radiation, thereby forming a highly crystalline cross-linked polymeric material; g) heating the highly crystalline cross-linked polymeric material to a temperature above the melt; h) pressurizing the heated polymeric material under at least about 10-1000 MPa, preferably at least about 150 MPa, more preferably at least about 250 MPa, i) holding at this pressure; j) cooling the heated polymeric material to about room temperature; and k) releasing the pressure to about an atmospheric pressure level, thereby forming oxidation-resistant cross-linked polymeric material.

In another aspect, invention provides methods of making highly crystalline cross-linked polymeric material comprising: a) pressurizing a polymeric material under at least about 10-1000 MPa, preferably at least about 150 MPa, more preferably at least about 250 MPa; b) heating the pressurized polymeric material to a temperature above 100° C. to below the melt of the pressurized polymeric material; c) holding at this pressure; d) cooling the heated polymeric material to about room temperature; e) releasing the pressure to about an atmospheric pressure level, thereby forming a highly crystalline polymeric material; and f) irradiating the highly crystalline polymeric material at a temperature below the melt with ionizing radiation, thereby forming a highly crystalline cross-linked polymeric material.

In another aspect, the invention provides methods of making oxidation-resistant cross-linked polymeric material comprising: a) pressurizing a polymeric material under at least about 10-1000 MPa, preferably at least about 150 MPa, more preferably at least about 250 MPa; b) heating the pressurized polymeric material to a temperature below the melt of the pressurized polymeric material, such as below 140° C.; c) holding at this pressure; d) cooling the heated polymeric material to about room temperature; e) releasing the pressure to about an atmospheric pressure level, thereby forming a highly crystalline polymeric material; f) irradiating the highly crystalline polymeric material at temperature below the melt with ionizing radiation, thereby forming a highly crystalline cross-linked polymeric material; g) heating the highly crystalline cross-linked polymeric material to a temperature above the melt; h) pressurizing the heated polymeric material under at least about 10-1000 MPa, preferably at least about 150 MPa, more preferably at least about 250 MPa; i) holding at this pressure; j) cooling the heated polymeric material to about room temperature; and k) releasing the pressure to about an atmospheric pressure level, thereby forming oxidation-resistant cross-linked polymeric material.

In another aspect, the oxidation-resistant highly crystalline cross-linked polymeric material is machined, thereby forming a medical implant. In another aspect, the oxidation-resistant highly crystalline cross-linked medical implant is packaged and sterilized by ionizing radiation or gas sterilization, thereby forming a sterile oxidation-resistant highly crystalline cross-linked medical implant.

In one aspect, the invention provides methods of making a cross-linked highly crystalline blend of polymer and additive comprising: a) blending polymeric material with an additive; b) consolidating the blend; c) pressurizing the blend under at least about 10-1000 MPa, preferably at least about 150 MPa, more preferably at least about 250 MPa; d) heating the pressurized the blend to a temperature of above 100° C. to below the melt of the pressurized blend; e) holding at this pressure; f) cooling the heated the blend to about room temperature; g) releasing the pressure to about an atmospheric pressure level, thereby forming a highly crystalline polymeric material; and h) irradiating the highly crystalline polymeric material at temperature below the melt with ionizing radiation, thereby forming a highly crystalline cross-linked blend of polymer and additive.

In one aspect, the invention provides methods of making a cross-linked highly crystalline blend of polymer and additive comprising: a) blending polymeric material with an additive; b) consolidating the blend; c) heating the blend to a temperature above the melting point of the blend; d) pressurizing the blend under at least about 10-1000 MPa, preferably at least about 150 MPa, more preferably at least about 250 MPa; e) holding at this pressure; f) cooling the heated the blend to about room temperature; g) releasing the pressure to about an atmospheric pressure level, thereby forming a highly crystalline polymeric material; and h) irradiating the highly crystalline polymeric material at temperature below the melt with ionizing radiation, thereby forming oxidation-resistant highly crystalline cross-linked blend of polymer and additive.

In one aspect, the invention provides methods of making oxidation-resistant cross-linked highly crystalline blend of polymer and additive comprising: a) blending polymeric material with an additive; b) consolidating the blend; c) irradiating the highly crystalline polymeric material at temperature below the melt with ionizing radiation; d) heating the cross-linked blend to a temperature above the melting point of the blend; e) pressurizing the cross-linked blend under at least about 10-1000 MPa, preferably at least about 150 MPa, more preferably at least about 250 MPa; f) holding at this pressure; g) cooling the heated the cross-linked blend to about room temperature; and h) releasing the pressure to about an atmospheric pressure level, thereby forming a an oxidation-resistant highly crystalline cross-linked blend of polymer and additive.

In one aspect, the invention provides methods of making a cross-linked highly crystalline blend of polymer and additive comprising: a) blending polymeric material with an additive; b) consolidating the blend; c) heating the blend to a temperature above the melting point of the blend; d) pressurizing the blend under at least about 10-1000 MPa, preferably at least about 150 MPa, more preferably at least about 250 MPa; e) holding at this pressure; f) cooling the heated the blend to about room temperature; g) releasing the pressure to about an atmospheric pressure level, thereby forming a highly crystalline polymeric material; h) machining the polymeric material thereby forming a medical implant; and i) irradiating the medical implant at temperature below the melt with ionizing radiation, thereby forming a highly crystalline cross-linked medical implant.

One aspect of the invention provides methods of making a cross-linked highly crystalline blend of polymer and additive comprising: a) blending polymeric material with an additive; b) consolidating the blend; c) pressurizing the blend under at least about 10-1000 MPa, preferably at least about 150 MPa, more preferably at least about 250 MPa; d) heating the pressurized the blend to a temperature of above 100° C. to below the melt of the pressurized blend; e) holding at this pressure; f) cooling the heated the blend to about room temperature; g) releasing the pressure to about an atmospheric pressure level, thereby forming a highly crystalline polymeric material; h) machining the polymeric material thereby forming a medical implant; and i) irradiating the medical implant at temperature below the melt with ionizing radiation, thereby forming a highly crystalline cross-linked medical implant.

In one aspect, invention provides methods of making oxidation-resistant cross-linked highly crystalline blend of polymer and additive comprising: a) blending polymeric material with an additive; b) consolidating the blend; c) irradiating the highly crystalline polymeric material at temperature below the melt with ionizing radiation; d) heating the cross-linked blend to a temperature above the melting point of the blend; e) pressurizing the cross-linked blend under at least about 10-1000 MPa, preferably at least about 150 MPa, more preferably at least about 250 MPa; f) holding at this pressure; g) cooling the heated the cross-linked blend to about room temperature; h) releasing the pressure to about an atmospheric pressure level, thereby forming oxidation-resistant cross-linked highly crystalline cross-linked blend of polymer and additive; and i) machining the polymeric material, thereby forming oxidation-resistant highly crystalline cross-linked medical implant.

In another aspect, the highly crystalline cross-linked blend of polymer and additive is machined, thereby forming a medical implant. In another aspect, the highly crystalline cross-linked medical implant is packaged and sterilized by ionizing radiation or gas sterilization, thereby forming a sterile highly crystalline cross-linked medical implant.

In another aspect, the invention provides a method of making highly crystalline blend of polymer with an additive comprising a plasticizing agent or a nucleating agent as additive.

In another aspect, the invention provides a method of making oxidation-resistant highly cross-linked blend of polymer comprising plasticizing the polymer with an additive like an antioxidant plasticizing agent, such as vitamin E.

In another aspect, the invention provides methods of making oxidation-resistant highly crystalline cross-linked polymeric material further comprising doping the highly crystalline cross-linked polymeric material with an antioxidant by diffusion, thereby forming antioxidant-doped highly crystalline cross-linked polymeric material.

In another aspect, the invention provides methods of making highly crystalline cross-linked polymeric material further comprising: a) machining the highly crystalline cross-linked polymeric material, thereby forming a medical implant; and b) doping the medical implant with an antioxidant by diffusion, thereby forming antioxidant-doped highly crystalline cross-linked medical implant.

In another aspect, the invention provides methods of making highly crystalline cross-linked polymeric material further comprising: a) doping the highly crystalline cross-linked polymeric material with an antioxidant by diffusion, thereby forming antioxidant-doped highly crystalline cross-linked polymeric material; and b) machining the antioxidant-doped highly crystalline cross-linked polymeric material, thereby forming antioxidant-doped highly crystalline cross-linked medical implant.

In one aspect, the antioxidant-doped highly crystalline cross-linked medical implant is packaged and sterilized by ionizing radiation or gas sterilization, thereby forming a sterile and antioxidant-doped highly crystalline cross-linked medical implant.

In another aspect, the invention provides methods of making highly crystalline cross-linked polymeric material further comprising: a) pressurizing the polymeric material under at least about 10-1000 MPa, preferably at least about 150 MPa, more preferably at least about 250 MPa; b) heating the pressurized polymeric material to a temperature of above 100° C. to below the melt of the pressurized polymeric material; c) cooling the heated polymeric material to about room temperature; d) releasing the pressure to about an atmospheric pressure level; e) doping the polymeric material with an antioxidant by diffusion, thereby forming antioxidant-doped polymeric material; and f) irradiating the antioxidant-doped polymeric material at temperature below the melt with ionizing radiation, thereby forming antioxidant-doped highly crystalline cross-linked polymeric material.

In another aspect, the invention provides methods of making a highly crystalline cross-linked polymeric material further comprising: a) pressurizing the polymeric material under at least about 10-1000 MPa, preferably at least about 150 MPa, more preferably at least about 250 MPa; b) heating the pressurized polymeric material to a temperature of above 100° C. to below the melt of the pressurized polymeric material; c) cooling the heated polymeric material to about room temperature; d) releasing the pressure to about an atmospheric pressure level; e) machining the highly crystalline polymeric material, thereby forming a medical implant; f) doping the medical implant with an antioxidant by diffusion, thereby forming antioxidant-doped medical implant; and g) irradiating the antioxidant-doped medical implant at temperature below the melt with ionizing radiation, thereby forming antioxidant-doped highly crystalline cross-linked polymeric material.

In another aspect, the invention provides a method of making oxidation-resistant highly crystalline cross-linked polymeric material comprising: a) doping the polymeric material (such as UHMWPE) with an antioxidant by diffusion, thereby forming an antioxidant-doped polymeric material; b) irradiating the antioxidant-doped polymeric material at a temperature below the melting point with ionizing radiation, thereby forming an antioxidant-doped cross-linked polymeric material; c) heating the antioxidant-doped cross-linked polymeric material to a temperature above the melting point; d) pressuring the polymeric material to at least about 10-1000 MPa, preferably at least about 150 MPa, more preferably at least about 250 MPa; e) holding at this pressure; f) cooling the heated polymeric material to about room temperature; and g) releasing the pressure to about an atmospheric pressure level, thereby forming an antioxidant-doped, cross-linked, highly crystalline polymeric material.

In another aspect, the invention provides a method of making oxidation-resistant highly crystalline cross-linked polymeric material comprising: a) doping the polymeric material (such as UHMWPE) with an antioxidant by diffusion, thereby forming an antioxidant-doped polymeric material; b) irradiating the antioxidant-doped polymeric material at a temperature below the melt with ionizing radiation, thereby forming an antioxidant-doped cross-linked polymeric material; c) pressurizing the cross-linked polymeric material under at least about 10-1000 MPa, preferably at least about 150 MPa, more preferably at least about 250 MPa; d) heating the pressurized cross-linked polymeric material to a temperature of above 100° C. to below the melting point of the pressurized cross-linked polymeric material; e) holding at the pressure and temperature; f) cooling the heated polymeric material to about room temperature; and g) releasing the pressure to about an atmospheric pressure level, thereby forming an antioxidant-doped cross-linked highly crystalline polymeric material.

In another aspect, the invention provides a method of making highly crystalline cross-linked polymeric material further comprising: a) heating the polymeric material to a temperature above the melt; b) pressurizing the heated polymeric material under at least about 10-1000 MPa, preferably at least about 150 MPa, more preferably at least about 250 MPa; c) cooling the heated polymeric material to about room temperature; d) releasing the pressure to about an atmospheric pressure level; e) doping the polymeric material with an antioxidant by diffusion, thereby forming an antioxidant-doped polymeric material; and f) irradiating the antioxidant-doped polymeric material at temperature below the melt with ionizing radiation, thereby forming an antioxidant-doped highly crystalline cross-linked polymeric material.

In another aspect, the invention provides methods of making highly crystalline cross-linked polymeric material comprising: a) heating the polymeric material to a temperature above the melt; b) pressurizing the heated polymeric material under at least about 10-1000 MPa, preferably at least about 150 MPa, more preferably at least about 250 MPa; c) cooling the heated polymeric material to about room temperature; d) releasing the pressure to about an atmospheric pressure level; e) machining the highly crystalline polymeric material, thereby forming a medical implant; f) doping the medical implant with an antioxidant by diffusion, thereby forming antioxidant-doped medical implant; and g) irradiating the antioxidant-doped medical implant at temperature below the melt with ionizing radiation, thereby forming antioxidant-doped highly crystalline cross-linked polymeric material.

In another aspect, the antioxidant-doped highly crystalline cross-linked polymeric material is machined, thereby forming a medical implant.

In another aspect, the antioxidant-doped highly crystalline cross-linked medical implant is washed, packaged and sterilized by ionizing radiation or gas sterilization, thereby forming a sterile and antioxidant-doped highly crystalline cross-linked medical implant.

In one aspect, before packaging and sterilization, the antioxidant-doped highly crystalline cross-linked medical implant is washed in an industrial washing machine with detergent. In another aspect, before packaging and sterilization, the antioxidant-doped highly crystalline cross-linked medical implant is washed by soaking in a solvent, such as ethanol.

In another aspect, the antioxidant-doped highly crystalline cross-linked polymeric material is washed, then machined, thereby forming a medical implant.

In another aspect, the antioxidant-doped highly crystalline cross-linked medical implant is packaged and sterilized by ionizing radiation or gas sterilization, thereby forming a sterile and antioxidant-doped highly crystalline cross-linked medical implant.

In another aspect, the antioxidant-doped highly crystalline cross-linked medical implant is packaged and sterilized by gas sterilization, thereby forming a sterile and antioxidant-doped highly crystalline cross-linked medical implant.

In another aspect, the highly crystalline and antioxidant-doped medical implant is packaged and irradiated with ionizing radiation to a radiation dose of more than 1 kGy, such as about 25-400 kGy or more, to cross-link and sterilize the medical implant. Preferably the radiation dose level is above 75 kGy, more preferably above 100 kGy, and yet more preferably about 150 kGy.

In one aspect, the polymeric material is heated to a temperature above the melting point of the pressurized polymeric material, for example, at 150° C., 180° C., 225° C., 300° C., or 320° C., and any temperature therebetween or thereabout as long as the temperature is below the thermal decomposition point.

In another, aspect, the invention provides a method of making oxidation-resistant highly crystalline cross-linked polymeric material comprising: a) heating a polymeric material to a temperature above the melt; b) pressurizing the heated polymeric material under at least about 10-1000 MPa, preferably at least about 150 MPa, more preferably at least about 250 MPa; c) holding at this pressure; d) cooling the heated polymeric material to about room temperature; e) releasing the pressure to about an atmospheric pressure level, thereby forming a highly crystalline polymeric material; f) irradiating the highly crystalline polymeric material at a temperature below the melt with ionizing radiation, thereby forming a highly crystalline cross-linked polymeric material, g) doping with an antioxidant, such as vitamin E, thereby forming an antioxidant-doped highly crystalline cross-linked polymeric material; h) mechanically deforming the antioxidant-doped highly crystalline cross-linked polymeric material below its melting point; and i) annealing the mechanically deformed antioxidant-doped polymeric material at a temperature below the melting point.

In another aspect, the invention provides a method of making an oxidation-resistant highly crystalline cross-linked polymeric material comprising: a) pressurizing a polymeric material under at least about 10-1000 MPa, preferably at least about 150 MPa, more preferably at least about 250 MPa; b) heating the pressurized polymeric material to a temperature above 100° C. to below the melt of the pressurized polymeric material; c) holding at this pressure; d) cooling the heated polymeric material to about room temperature; e) releasing the pressure to about an atmospheric pressure level, thereby forming a highly crystalline polymeric material; f) irradiating the highly crystalline polymeric material at a temperature below the melt with ionizing radiation, thereby forming a highly crystalline cross-linked polymeric material; g) doping with an antioxidant, such as vitamin E, thereby forming an antioxidant-doped highly crystalline cross-linked polymeric material; h) mechanically deforming the antioxidant-doped highly crystalline cross-linked polymeric material below its melting point; and i) annealing the mechanically deformed antioxidant-doped polymeric material at a temperature below the melting point.

In another aspect, the invention provides methods of making oxidation-resistant cross-linked highly crystalline blend of polymer and additive comprising: a) blending polymeric material with an additive; b) consolidating the blend; c) heating the blend to a temperature above the melting point of the blend; d) pressurizing the blend under at least about 10-1000 MPa, preferably at least about 150 MPa, more preferably at least about 250 MPa; e) holding at this pressure; f) cooling the heated the blend to about room temperature; g) releasing the pressure to about an atmospheric pressure level, thereby forming a highly crystalline polymeric material; h) irradiating the highly crystalline polymeric material at temperature below the melt with ionizing radiation, thereby forming oxidation-resistant highly crystalline cross-linked blend of polymer and additive; i) doping with an antioxidant, such as vitamin E, thereby forming antioxidant-doped highly crystalline cross-linked blend; j) mechanically deforming the antioxidant-doped highly crystalline cross-linked blend below its melting point; and k) annealing the mechanically deformed antioxidant-doped blend at a temperature below the melting point.

In another aspect, the invention provides methods of making oxidation-resistant cross-linked highly crystalline blend of polymer and additive comprising: a) blending polymeric material with an additive; b) consolidating the blend; c) pressurizing the blend under at least about 10-1000 MPa, preferably at least about 150 MPa, more preferably at least about 250 MPa; d) heating the pressurized the blend to a temperature between above 100° C. and below the melting point of the pressurized blend; e) holding at this pressure; f) cooling the heated the blend to about room temperature; g) releasing the pressure to about an atmospheric pressure level, thereby forming a highly crystalline polymeric material; h) irradiating the highly crystalline polymeric material at temperature below the melt with ionizing radiation, thereby forming a highly crystalline cross-linked blend of polymer and additive; i) doping with an antioxidant, such as vitamin E, thereby forming an antioxidant-doped highly crystalline cross-linked blend; j) mechanically deforming the antioxidant-doped highly crystalline cross-linked blend below its melting point; and k) annealing the mechanically deformed antioxidant-doped blend at a temperature below the melting point.

In another aspect, the highly crystalline polymeric material is irradiated at a temperature between about room temperature and about 90° C., or at a temperature between about 90° C. and the peak melting point of the highly crystalline polymeric material.

In another aspect, the irradiated polymeric material is annealed at a temperature below the melting point of the polymeric materials for example, a temperature between about 90° C. and peak melting point of the irradiated polymeric material.

In another aspect, the polymeric material can be pressurized to above about 150 MPa, for example, about 200 MPa, 250 MPa, 310 MPa, 300 MPa, 320 MPa, 400 MPa, or 450 MPa.

Yet in another aspect, the invention provides medical implants comprising the highly crystalline cross-linked and antioxidant-doped highly crystalline cross-linked polymeric material and highly crystalline cross-linked polymer blend with an additive made as described herein. In another aspect, the polymeric material is compression molded to another piece or a medical implant, thereby forming an interface or an interlocked hybrid material. The medical implants, according to an aspect of the invention, comprises medical devices including acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, vascular grafts.

According to one aspect, the invention provides radiation treated UHMWPE having more than 2 melting peaks and a crystallinity above about 50%. In another aspect, the invention provides finished products, for example, an article, a medical device or a medical prosthesis and the like, comprising UHMWPE, wherein the UHMWPE having at least two melting peaks and a crystallinity of at least about 50%. According to the invention, the UHMWPE or the finished product is doped with vitamin E, irradiated to a dose of more than 1 kGy, such as about 25-400 kGy or more, preferably to about 150 kGy, and has detectable free radicals.

According to another aspect, the invention provides UHMWPE made by blending the UHMWPE powder with vitamin E, irradiating the vitamin E blended UHMWPE, high pressure crystallizing the blend by heating to a temperature above the melting point of the irradiated UHMWPE at an ambient pressure, pressurizing to at least about 10-1000 MPa, preferably at least about 150 MPa, more preferably at least about 250 MPa, cooling to about room temperature while under pressure, and releasing the pressure. According to the invention, the UHMWPE is irradiated to a dose of more than 1 kGy, such as about 25-400 kGy or more, preferably to about 150 kGy, and machined to form a finished product, for example, a medical implant and the like. The finished product can be packaged and sterilized.

According to another aspect, the invention provides methods of making oxidation-resistant cross-linked highly crystalline blend of polymer (such as UHMWPE) and additive comprising: a) blending polymeric material with an additive; b) consolidating the blend; c) irradiating the highly crystalline polymeric material at a temperature below the melt with ionizing radiation, thereby providing a cross-linked blend of polymeric material and additive; d) pressurizing the cross-linked blend under at least about 10-1000 MPa, preferably at least about 150 MPa, more preferably at least about 250 MPa; e) heating the pressurized cross-linked blend to a temperature above 100° C. to below the melting point of the pressurized cross-linked blend; f) holding at this pressure and temperature; g) cooling the heated blend to about room temperature;

and h) releasing the pressure to about an atmospheric pressure level, thereby forming a highly crystalline cross-linked blend of polymeric material and additive. According to the invention, the UHMWPE is irradiated to a dose of more than 1 kGy, such as about 25-400 kGy or more, preferably to about 150 kGy, has detectable free radicals, and is machined to form a finished product, for example, a medical implant and the like. The finished product can be packaged and sterilized.

According to another aspect, the invention provides UHMWPE made by blending the UHMWPE powder with vitamin E, irradiating the vitamin E blended UHMWPE, Pressurizing to at least 10-1000 MPa, preferably at least about 150 MPa, more preferably at least about 250 MPa, heating to a temperature above the melting of the irradiated polyethylene at ambient pressure, cooling to about room temperature while under pressure, and releasing the pressure. According to the invention, the UHMWPE is irradiated to a dose of more than 1 kGy, such as about 25-400 kGy or more, preferably to about 150 kGy, has detectable free radicals, and is machined to form a finished product, for example, a medical implant and the like. The finished product can be packaged and sterilized.

According to another aspect, the invention provides methods of making oxidation-resistant cross-linked highly crystalline blend of polymer (such as UHMWPE) and additive comprising: a) blending polymeric material with an additive; b) consolidating the blend; c) irradiating the highly crystalline polymeric material at a temperature below the melt with ionizing radiation, thereby providing a cross-linked blend of polymeric material and additive; d) machining the blend, thereby forming a finished product, for example, a medical implant and the like; e) heating the medical implant to a temperature above the melting point; f) pressuring the medical implant to at least 10-1000 MPa, preferably at least about 150 MPa, more preferably at least about 250 MPa; g) holding at this pressure; h) cooling the heated medical implant to about room temperature; and i) releasing the pressure to about an atmospheric pressure level, thereby forming antioxidant-doped cross-linked highly crystalline medical implant. According to the invention, the UHMWPE is irradiated to a dose of more than 1 kGy, such as about 25-400 kGy or more, preferably to about 150 kGy, has detectable free radicals, and is machined to form a finished product, for example, a medical implant and the like. The finished product can be packaged and sterilized.

According to another aspect, the invention provides UHMWPE made by blending the UHMWPE powder with vitamin E, irradiating the vitamin E blended UHMWPE, forming a finished product, for example a medical implant, high pressure crystallizing the blend by heating to a temperature above the melting point of the irradiated polyethylene at ambient pressure, pressurizing to at least 10-1000 MPa, preferably at least about 150 MPa, more preferably at least about 250 MPa, cooling to about room temperature while under pressure, and releasing the pressure. According to the invention, the UHMWPE is irradiated to a dose of more than 1 kGy, such as about 25-400 kGy or more, preferably to about 150 kGy, wherein the finished product is formed by consolidating the vitamin E-doped UHMWPE and by machining. In another aspect, the finished product is formed by direct compression molding the vitamin E-doped UHMWPE into implant shape, wherein the implant shape is a finished shape of the implant or the implant shape may require further machining for a finished shape of the implant. The finished product can be packaged and sterilized.

According to another aspect, the invention provides UHMWPE made by blending the UHMWPE powder with vitamin E, irradiating the vitamin E blended UHMWPE, forming a finished product, for example a medical implant, pressurizing to at least about 10-1000 MPa, preferably at least about 150 MPa, more preferably at least about 250 MPa, heating to a temperature above the melting point of the irradiated polyethylene at ambient pressure, cooling to about room temperature, and releasing the pressure. According to the invention, the UHMWPE is irradiated to a dose of more than 1 kGy, such as about 25-400 kGy or more, preferably to about 150 kGy, wherein the finished product has detectable free radicals. The finished product can be formed by direct compression molding the vitamin E-doped UHMWPE into implant shape, wherein the implant shape is a finished shape of the implant or the implant shape may require further machining for a finished shape of the implant. The finished product can be packaged and sterilized.

According to another aspect, the invention provides methods of making oxidation-resistant cross-linked highly crystalline blend of polymer (such as UHMWPE) and additive comprising: a) blending polymeric material with an additive; b) consolidating the blend; c) irradiating the highly crystalline polymeric material at a temperature below the melt with ionizing radiation, thereby providing a cross-linked blend of polymeric material and additive, d) machining the blend, thereby forming a finished product, for example, a medical implant and the like; e) pressurizing the implant under at least about 10-1000 MPa, preferably at least about 150 MPa, more preferably at least about 250 MPa; f) heating the pressurized implant to a temperature above 100° C. to below the melt of the pressurized implant; g) holding at this pressure and temperature; h) cooling the heated implant to about room temperature; and i) releasing the pressure to about an atmospheric pressure level, thereby forming a highly crystalline cross-linked medical implant. According to the invention, the UHMWPE is irradiated to a dose of more than 1 kGy, such as about 25-400 kGy or more, preferably to about 150 kGy, has detectable free radicals, and is machined to form a finished product, for example, a medical implant and the like. The finished product can be packaged and sterilized.

According to another aspect, the invention provides irradiated UHMWPE, wherein the UHMWPE is machined to form a finished product, for example, an article, an implant, or a medical prosthesis and the like, and wherein the finished product is high pressure crystallized. According to the invention, the UHMWPE is irradiated to a dose of more than 1 kGy, such as about 25-400 kGy or more, preferably to about 150 kGy, more preferably to about 65 kGy, wherein the UHMWPE is irradiated at above about 80° C. and below the melting point of the irradiated UHMWPE, wherein the UHMWPE is melted before machining to form a finished product or an article. High pressure crystallization is carried out by heating to a temperature above the melting point of the irradiated polyethylene at ambient pressure, pressurizing to at least about 10-1000 MPa, preferably at least about 150 MPa, more preferably at least about 250 MPa, heating to a temperature above the melting point of the irradiated polyethylene at ambient pressure, cooling to about room temperature, and releasing the pressure. High pressure crystallization also can be carried out by pressurizing to at least about 10-1000 MPa, preferably at least about 150 MPa, more preferably at least about 250 MPa, heating to a temperature above the melting point of the irradiated polyethylene at ambient pressure, cooling to about room temperature, and releasing the pressure. The finished product can be packaged and sterilized.

In another aspect, the invention provides methods of making a cross-linked highly crystalline polymeric material comprising: a) heating the polymeric material to a temperature above the melt; b) pressurizing the polymeric material under at least 10-1000 MPa, preferably at least about 150 MPa, more preferably at least about 250 MPa; c) holding at this pressure and temperature; d) cooling the heated polymeric material to about room temperature; e) releasing the pressure to about an atmospheric pressure level, thereby forming a highly crystalline polymeric material; f) irradiating the polymeric-material at a temperature below the melt with ionizing radiation, thereby forming a highly crystalline cross-linked polymeric material; g) pressuring the highly crystalline highly cross-linked polymeric material under at least 10-1000 MPa, preferably at least about 150 MPa, more preferably at least about 250 MPa; h) heating the pressurized polymeric material to a temperature of above 100° C. to below the melt of the pressurized highly crystalline, highly cross-linked polymeric material; i) holding at this pressure and temperature; j) cooling the heated polymeric material to about room temperature; and k) releasing the pressure to about an atmospheric pressure level, thereby forming a highly crystalline highly cross-linked polymeric material.

In another aspect, the invention provides methods of making a cross-linked highly crystalline polymeric material comprising: a) pressuring the polymeric material under at least 10-1000 MPa, preferably at least about 150 MPa, more preferably at least about 250 MPa; b) heating the pressurized polymeric material to a temperature of above 100° C. to below the melt of the pressurized polymeric material; c) holding at this pressure and temperature; d) cooling the heated polymeric material to about room temperature; e) releasing the pressure to about an atmospheric pressure level, thereby forming a highly crystalline polymeric material; f) irradiating the polymeric material at a temperature below the melt with ionizing radiation, thereby forming a highly crystalline cross-linked polymeric material; g) pressuring the highly crystalline, highly cross-linked polymeric material under at least 10-1000 MPa, preferably at least about 150 MPa, more preferably at least about 250 MPa; h) heating the pressurized polymeric material under at least about 10-1000 MPa, preferably at least about 150 MPa, more preferably at least about 250 MPa; i) heating the pressurized polymeric material to a temperature of above 100° C. to below the melt of the pressurized highly crystalline, highly cross-linked polymeric material; j) holding at this pressure and temperature; k) cooling the heated polymeric material to about room temperature; and l) releasing the pressure to about an atmospheric pressure level, thereby forming a highly crystalline highly cross-linked polymeric material.

In another aspect, the invention provides methods of making oxidation-resistant cross-linked highly crystalline polymeric material comprising: a) heating the polymeric material to a temperature above the melt; b) pressurizing the polymeric material under at least 10-1000 MPa, preferably at least about 150 MPa, more preferably at least about 250 MPa; c) holding at this pressure and temperature; d) cooling the heated polymeric material to about room temperature; e) releasing the pressure to about an atmospheric pressure level, thereby forming a highly crystalline polymeric material; f) irradiating the polymeric material at a temperature below the melt with ionizing radiation, thereby forming a highly crystalline cross-linked polymeric material; and g) doping the highly crystalline highly cross-linked polymeric material with an antioxidant by diffusion, thereby forming oxidation-resistant highly crystalline highly cross-linked polymeric material.

In another aspect, the invention provides methods of making oxidation-resistant cross-linked highly crystalline polymeric material comprising: a) pressuring the polymeric material under at least 10-1000 MPa, preferably at least about 150 MPa, more preferably at least about 250 MPa; b) heating the pressurized polymeric material to a temperature of above 100° C. to below the melt of the pressurized polymeric material; c) holding at this pressure and temperature; d) cooling the heated polymeric material to about room temperature; e) releasing the pressure to about an atmospheric pressure level, thereby forming a highly crystalline polymeric material; f) irradiating the polymeric material at a temperature below the melt with ionizing radiation, thereby forming a highly crystalline cross-linked polymeric material; and g) doping the highly crystalline, highly cross-linked polymeric material with an antioxidant by diffusion, thereby forming oxidation-resistant highly crystalline highly cross-linked polymeric material.

In another aspect, the invention provides methods of making oxidation-resistant cross-linked highly crystalline polymeric material comprising: a) heating the polymeric material to a temperature above the melt; b) pressurizing the polymeric material under at least 10-1000 MPa, preferably at least about 150 MPa, more preferably at least about 250 MPa; c) holding at this pressure and temperature; d) cooling the heated polymeric material to about room temperature; e) releasing the pressure to about an atmospheric pressure level, thereby forming a highly crystalline polymeric material; f) irradiating the polymeric material at a temperature below the melt with ionizing radiation, thereby forming a highly crystalline cross-linked polymeric material; g) mechanically deforming the highly crystalline highly cross-linked polymeric material below its melting point; and h) annealing the mechanically deformed highly crystalline highly crosslinked polymeric material at a temperature below the melting point, thereby forming oxidation-resistant highly crystalline highly cross-linked polymeric material.

In another aspect, the invention provides methods of making oxidation-resistant cross-linked highly crystalline polymeric material comprising: a) pressuring the polymeric material under at least 10-1000 MPa, preferably at least about 150 MPa, more preferably at least about 250 MPa; b) heating the pressurized polymeric material to a temperature of above 100° C. to below the melt of the pressurized polymeric material; c) holding at this pressure and temperature; d) cooling the heated polymeric material to about room temperature; e) releasing the pressure to about an atmospheric pressure level, thereby forming a highly crystalline polymeric material; f) irradiating the polymeric material at a temperature below the melt with ionizing radiation, thereby forming a highly crystalline cross-linked polymeric material; g) mechanically deforming the highly crystalline highly cross-linked polymeric material below its melting point; and h) annealing the mechanically deformed highly crystalline highly crosslinked polymeric material at a temperature below the melting point, thereby forming oxidation-resistant highly crystalline, highly cross-linked polymeric material.

In another aspect, the invention provides methods of making oxidation-resistant cross-linked highly crystalline blend of polymeric material and additive comprising: a) blending the polymeric material with an additive; b) consolidating the blend; c) heating the polymeric material to a temperature above the melt; d) pressurizing the polymeric material under at least 10-1000 MPa, preferably at least about 150 MPa, more preferably at least about 250 MPa; e) holding at this pressure and temperature; f) cooling the heated polymeric material to about room temperature; g) releasing the pressure to about an atmospheric pressure level, thereby forming a highly crystalline polymeric material; h) irradiating the polymeric material at a temperature below the melt with ionizing radiation, thereby forming a highly crystalline cross-linked polymeric material; i) heating the highly crystalline highly cross-linked blend to above the melt; j) pressuring the highly cross-linked blend under at least 10-1000 MPa, preferably at least about 150 MPa, more preferably at least about 250 MPa; k) holding at this pressure and temperature; l) cooling the heated blend to about room temperature; and m) releasing the pressure to about an atmospheric pressure level, thereby forming oxidation-resistant highly crystalline highly cross-linked blend of polymeric material and additive.

In another aspect, the invention provides methods of making oxidation-resistant cross-linked highly crystalline blend of polymeric material and additive comprising: a) blending the polymeric material with an additive; b) consolidating the blend; c) heating the polymeric material to a temperature above the melt; d) pressurizing the polymeric material under at least 10-1000 MPa, preferably at least about 150 MPa, more preferably at least about 250 MPa; e) holding at this pressure and temperature; f) cooling the heated polymeric material to about room temperature; g) releasing the pressure to about an atmospheric pressure level, thereby forming a highly crystalline polymeric material; h) irradiating the polymeric material at a temperature below the melt with ionizing radiation, thereby forming a highly crystalline cross-linked polymeric material; i) pressuring the highly crystalline highly cross-linked polymeric material under at least 10-1000 MPa, preferably at least about 150 MPa, more preferably at least about 250 MPa; j) heating the pressurized polymeric material to a temperature of above 100° C. to below the melt of the pressurized highly crystalline highly cross-linked polymeric material; k) holding at this pressure and temperature; l) cooling the heated polymeric material to about room temperature; and m) releasing the pressure to about an atmospheric pressure level, thereby forming a highly crystalline highly cross-linked blend of polymeric material and additive.

In another aspect, the invention provides methods of making oxidation-resistant highly cross-linked highly crystalline blend of polymeric material and additive comprising: a) pressuring the polymeric material under at least 10-1000 MPa, preferably at least about 150 MPa, more preferably at least about 250 MPa; b) heating the pressurized polymeric material to a temperature of above 100° C. to below the melt of the pressurized polymeric material; c) holding at this pressure and temperature; d) cooling the heated polymeric material to about room temperature; e) releasing the pressure to about an atmospheric pressure level, thereby forming a highly crystalline blend; f) irradiating the blend at a temperature below the melt with ionizing radiation, thereby forming a highly crystalline cross-linked blend; g) heating the highly crystalline highly cross-linked blend to a temperature above the melt; h) pressurizing the highly cross-linked blend under at least 10-1000 MPa, preferably at least about 150 MPa, more preferably at least about 250 MPa; i) holding at this pressure and temperature; j) cooling the heated highly cross-linked blend to about room temperature; and k) releasing the pressure to about an atmospheric pressure level, thereby forming oxidation-resistant highly crystalline highly cross-linked blend of polymeric material and additive.

In another aspect, the invention provides methods of making oxidation-resistant highly cross-linked highly crystalline blend of polymeric material and additive comprising: a) pressuring the polymeric material under at least 10-1000 MPa, preferably at least about 150 MPa, more preferably at least about 250 MPa; b) heating the pressurized polymeric material to a temperature of above 100° C. to below the melt of the pressurized polymeric material; c) holding at this pressure and temperature; d) cooling the heated polymeric material to about room temperature; e) releasing the pressure to about an atmospheric pressure level, thereby forming a highly crystalline blend; f) irradiating the blend at a temperature below the melt with ionizing radiation, thereby forming a highly crystalline cross-linked blend; g) pressuring the highly crystalline, highly cross-linked blend under at least 10-1000 MPa, preferably at least about 150 MPa, more preferably at least about 250 MPa; h) heating the pressurized cross-linked blend under at least about 10-1000 MPa, preferably at least about 150 MPa, more preferably at least about 250 MPa; i) heating the pressurized cross-linked blend to a temperature of above 100° C. to below the melt of the pressurized highly crystalline, highly cross-linked blend; j) holding at this pressure and temperature; k) cooling the heated cross-linked blend to about room temperature; and l) releasing the pressure to about an atmospheric pressure level, thereby forming oxidation-resistant highly crystalline highly cross-linked blend of polymeric material and additive.

In another aspect, the invention provides methods of making oxidation-resistant cross-linked highly crystalline blend of polymeric material and additive comprising: a) blending the polymeric material with an additive; b) consolidating the blend; c) heating the blend to a temperature above the melt; d) pressurizing the blend under at least 10-1000 MPa, preferably at least about 150 MPa, more preferably at least about 250 MPa; e) holding at this pressure and temperature; f) cooling the heated blend to about room temperature; g) releasing the pressure to about an atmospheric pressure level, thereby forming a highly crystalline blend; h) irradiating the blend at a temperature below the melt with ionizing radiation, thereby forming a highly crystalline cross-linked blend; i) mechanically deforming the highly crystalline highly cross-linked blend below its melting point; and j) annealing the mechanically deformed highly crystalline highly crosslinked blend at a temperature below the melting point, thereby forming oxidation-resistant highly crystalline highly cross-linked blend of polymeric material and additive.

In another aspect, the invention provides methods of making oxidation-resistant cross-linked highly crystalline blend of polymeric material and additive comprising: a) blending the polymeric material with an additive; b) consolidating the blend; c) pressuring the blend under at least 10-1000 MPa, preferably at least about 150 MPa, more preferably at least about 250 MPa; d) heating the pressurized blend to a temperature of above 100° C. to below the melt of the pressurized blend; e) holding at this pressure and temperature; f) cooling the heated blend to about room temperature; g) releasing the pressure to about an atmospheric pressure level, thereby forming a highly crystalline blend; h) irradiating the blend at a temperature below the melt with ionizing radiation, thereby forming a highly crystalline cross-linked blend; i) mechanically deforming the highly crystalline highly cross-linked blend below its melting point; and j) annealing the mechanically deformed highly crystalline highly crosslinked blend at a temperature below the melting point, thereby forming oxidation-resistant highly crystalline highly cross-linked blend of polymeric material and additive.

In another aspect, the invention provides methods of making oxidation-resistant antioxidant-doped cross-linked highly crystalline polymeric material comprising: a) doping the polymeric material with an antioxidant by diffusion; b) heating the antioxidant-doped polymeric material to a temperature above the melt; c) pressurizing the antioxidant-doped polymeric material under at least 10-1000 MPa, preferably at least about 150 MPa, more preferably at least about 250 MPa; d) holding at this pressure and temperature; e) cooling the heated antioxidant-doped polymeric material to about room temperature; f) releasing the pressure to about an atmospheric pressure level, thereby forming a highly crystalline antioxidant-doped polymeric material; g) irradiating the antioxidant-doped polymeric material at a temperature below the melt with ionizing radiation, thereby forming a highly crystalline cross-linked antioxidant-doped polymeric material; h) heating the highly crystalline, highly cross-linked antioxidant-doped polymeric material to above the melt; i) pressuring the highly cross-linked antioxidant-doped polymeric material under at least 10-1000 MPa, preferably at least about 150 MPa, more preferably at least about 250 MPa; j) holding at this pressure and temperature; k) cooling the heated antioxidant-doped polymeric material to about room temperature; and l) releasing the pressure to about an atmospheric pressure level, thereby forming oxidation-resistant highly crystalline highly cross-linked antioxidant-doped polymeric material.

In another aspect, the invention provides methods of making oxidation-resistant antioxidant-doped cross-linked highly crystalline polymeric material comprising: a) doping the polymeric material with an antioxidant by diffusion; b) heating the antioxidant-doped polymeric material to a temperature above the melt; c) pressurizing the antioxidant-doped polymeric material under at least 10-1000 MPa, preferably at least about 150 MPa, more preferably at least about 250 MPa; d) holding at this pressure and temperature; e) cooling the heated antioxidant-doped polymeric material to about room temperature; f) releasing the pressure to about an atmospheric pressure level, thereby forming a highly crystalline antioxidant-doped polymeric material; g) irradiating the antioxidant-doped polymeric material at a temperature below the melt with ionizing radiation, thereby forming a highly crystalline cross-linked antioxidant-doped polymeric material; h) pressuring the highly crystalline highly cross-linked antioxidant-doped polymeric material under at least 10-1000 MPa, preferably at least about 150 MPa, more preferably at least about 250 MPa; i) heating the pressurized antioxidant-doped polymeric material to a temperature of above 100° C. to below the melt of the pressurized highly crystalline highly cross-linked antioxidant-doped polymeric material; j) holding at this pressure and temperature; k) cooling the heated antioxidant-doped polymeric material to about room temperature; and l) releasing the pressure to about an atmospheric pressure level, thereby forming a highly crystalline highly cross-linked antioxidant-doped polymeric material.

In another aspect, the invention provides methods of making oxidation-resistant antioxidant-doped cross-linked highly crystalline polymeric material comprising: a) doping the polymeric material with an antioxidant by diffusion; b) pressuring the antioxidant-doped polymeric material under at least 10-1000 MPa, preferably at least about 150 MPa, more preferably at least about 250 MPa; c) heating the pressurized antioxidant-doped polymeric material to a temperature of above 100° C. to below the melt of the pressurized antioxidant-doped polymeric material; d) holding at this pressure and temperature; e) cooling the heated antioxidant-doped polymeric material to about room temperature; f) releasing the pressure to about an atmospheric pressure level, thereby forming a highly crystalline antioxidant-doped polymeric material; g) irradiating the blend at a temperature below the melt with ionizing radiation, thereby forming a highly crystalline cross-linked antioxidant-doped polymeric material; h) heating the highly crystalline highly cross-linked antioxidant-doped polymeric material to a temperature above the melt; i) pressurizing the highly cross-linked antioxidant-doped polymeric material under at least 10-1000 MPa, preferably at least about 150 MPa, more preferably at least about 250 MPa; j) holding at this pressure and temperature; k) cooling the heated highly cross-linked antioxidant-doped polymeric material to about room temperature; and l) releasing the pressure to about an atmospheric pressure level, thereby forming oxidation-resistant highly crystalline highly cross-linked antioxidant-doped polymeric material.

In another aspect, the invention provides methods of making oxidation-resistant antioxidant-doped cross-linked highly crystalline polymeric material comprising: a) doping the polymeric material with an antioxidant by diffusion; b) pressuring the antioxidant-doped polymeric material under at least 10-1000 MPa, preferably at least about 150 MPa, more preferably at least about 250 MPa; c) heating the pressurized antioxidant-doped polymeric material to a temperature of above 100° C. to below the melt of the pressurized antioxidant-doped polymeric material; d) holding at this pressure and temperature; e) cooling the heated antioxidant-doped polymeric material to about room temperature; f) releasing the pressure to about an atmospheric pressure level, thereby forming a highly crystalline antioxidant-doped polymeric material; g) irradiating the highly crystalline antioxidant-doped polymeric material at a temperature below the melt with ionizing radiation, thereby forming a highly crystalline cross-linked antioxidant-doped polymeric material; h) pressuring the highly crystalline, highly cross-linked antioxidant-doped polymeric material under at least 10-1000 MPa, preferably at least about 150 MPa, more preferably at least about 250 MPa; i) heating the pressurized cross-linked antioxidant-doped polymeric material under at least about 10-1000 MPa, preferably at least about 150 MPa, more preferably at least about 250 MPa; j) heating the pressurized cross-linked antioxidant-doped polymeric material to a temperature of above 100° C. to below the melt of the pressurized highly crystalline, highly cross-linked antioxidant-doped polymeric material; k) holding at this pressure and temperature; l) cooling the heated cross-linked antioxidant-doped polymeric material to about room temperature; and m) releasing the pressure to about an atmospheric pressure level, thereby forming oxidation-resistant highly crystalline highly cross-linked antioxidant-doped polymeric material.

In another aspect, the invention provides methods of making oxidation-resistant cross-linked highly crystalline antioxidant-doped polymeric material comprising: a) doping the polymeric material with an antioxidant by diffusion; b) heating the antioxidant-doped polymeric material to a temperature above the melt; c) pressurizing the antioxidant-doped polymeric material under at least 10-1000 MPa, preferably at least about 150 MPa, more preferably at least about 250 MPa; d) holding at this pressure and temperature; e) cooling the heated antioxidant-doped polymeric material to about room temperature; f) releasing the pressure to about an atmospheric pressure level, thereby forming a highly crystalline antioxidant-doped polymeric material; g) irradiating the antioxidant-doped polymeric material at a temperature below the melt with ionizing radiation, thereby forming a highly crystalline cross-linked antioxidant-doped polymeric material; h) mechanically deforming the highly crystalline, highly cross-linked antioxidant-doped polymeric material below its melting point; and i) annealing the mechanically deformed highly crystalline highly crosslinked antioxidant-doped polymeric material at a temperature below the melting point, thereby forming oxidation-resistant highly crystalline, highly cross-linked antioxidant-doped polymeric material.

In another aspect, the invention provides methods of making oxidation-resistant cross-linked highly crystalline antioxidant-doped polymeric material comprising: a) doping the polymeric material with an antioxidant by diffusion; b) pressuring the antioxidant-doped polymeric material under at least 10-1000 MPa, preferably at least about 150 MPa, more preferably at least about 250 MPa; c) heating the pressurized antioxidant-doped polymeric material to a temperature of above 100° C. to below the melt of the pressurized antioxidant-doped polymeric material; d) holding at this pressure and temperature; e) cooling the heated antioxidant-doped polymeric material to about room temperature; f) releasing the pressure to about an atmospheric pressure level, thereby forming a highly crystalline antioxidant-doped polymeric material; g) irradiating the antioxidant-doped polymeric material at a temperature below the melt with ionizing radiation, thereby forming a highly crystalline cross-linked antioxidant-doped polymeric material; h) mechanically deforming the highly crystalline, highly cross-linked antioxidant-doped polymeric material below its melting point; and i) annealing the mechanically deformed highly crystalline, highly crosslinked antioxidant-doped polymeric material at a temperature below the melting point, thereby forming oxidation-resistant highly crystalline, highly cross-linked antioxidant-doped polymeric material.

In another aspect, the invention provides methods of making oxidation-resistant highly cross-linked blend of polymeric material and additive comprising: a) blending the polymeric material with an additive; b) consolidating the blend; c) irradiating the blend at a temperature below the melt with ionizing radiation, thereby forming a cross-linked blend; d) mechanically deforming highly cross-linked blend below its melting point; and e) annealing the mechanically deformed highly crosslinked blend at a temperature below the melting point, thereby forming oxidation-resistant highly cross-linked blend of polymeric material and additive.

In another aspect, the invention provides methods of making oxidation-resistant highly cross-linked blend of polymeric material and additive comprising: a) blending the polymeric material with an additive; b) consolidating the blend; c) irradiating the blend at a temperature below the melt with ionizing radiation, thereby forming a cross-linked blend; d) mechanically deforming highly cross-linked blend below its melting point; and e) annealing the mechanically deformed highly crosslinked blend at a temperature below the melting point, thereby forming oxidation-resistant highly cross-linked blend, f) pressurizing the oxidation-resistant, highly cross-linked blend to at least 10-1000 MPa, preferably at least about 150 MPa, more preferably at least about 250 MPa; g) heating the pressurized highly cross-linked blend to a temperature of above 100° C. to below the melt of the pressurized highly cross-linked blend; h) holding at this pressure and temperature; i) cooling the heated highly cross-linked blend to about room temperature; and j) releasing the pressure to about an atmospheric pressure level, thereby forming oxidation-resistant highly crystalline highly cross-linked blend of polymeric material and additive.

In another aspect, the invention provides UHMWPE made by heating to a temperature above the melting point, pressurizing to at least 10-1000 MPa, preferably at least 150 MPa, more preferably at least 250 MPa, holding at this temperature, cooling to about room temperature, releasing the pressure, irradiating the high pressure crystallized UHMWPE and then diffusing with an antioxidant such as vitamin E. High pressure crystallization also can be carried out by pressurizing to at least 10-1000 MPa, preferably at least 150 MPa, more preferably at least 250 MPa, heating above 100° C. to below the melt of the pressurized polymeric material, holding at this pressure and temperature, cooling to about room temperature and releasing the pressure. According to the invention, the UHMWPE is irradiated to a dose of more than 1 kGy, such as about 25-400 kGy or more, preferably to about 150 kGy, wherein the finished product has detectable free radicals, wherein the finished product is formed by direct compression molding of the vitamin E-doped UHMWPE into implant shape, wherein the implant shape is a finished shape of the implant or the implant shape may require further machining for a finished shape of the implant. The finished product can be packaged and sterilized.

In another aspect, the invention provides UHMWPE made by heating to a temperature above the melting point temperature, pressurizing to at least 10-1000 MPa, preferably at least 150 MPa, more preferably at least 250 MPa, holding at this temperature, cooling to room temperature, releasing the pressure, irradiating the high pressure crystallized UHMWPE, mechanically deforming the high pressure crystallized UHMWPE below the melt and annealing at a temperature below the melt. High pressure crystallization also can be carried out by pressurizing to at least 10-1000 MPa, preferably at least 150 MPa, more preferably at least 250 MPa, heating above 100° C. to below the melt of the pressurized polymeric material, holding at this pressure and temperature, cooling to about room temperature and releasing the pressure. According to the invention, the UHMWPE is irradiated to a dose of more than 1 kGy, such as about 25-400 kGy or more, preferably to about 150 kGy, wherein the finished product has no detectable free radicals. The finished product can be machined to form a medical device. The medical device can be packaged and sterilized.

In another aspect, the invention provides UHMWPE made by diffusing an antioxidant such as vitamin E, heating to a temperature above the melting point temperature, pressurizing to at least 10-1000 MPa, preferably at least 150 MPa, more preferably at least 250 MPa, holding at this temperature, cooling to about room temperature, releasing the pressure, irradiating the high pressure crystallized UHMWPE, mechanically deforming the high pressure crystallized UHMWPE below the melt and annealing at a temperature below the melt. High pressure crystallization also can be carried out by pressurizing to at least 10-1000 MPa, preferably at least 150 MPa, more preferably at least 250 MPa, heating above 100° C. to below the melt of the pressurized polymeric material, holding at this pressure and temperature, cooling to about room temperature and releasing the pressure. According to the invention, the UHMWPE is irradiated to a dose of more than 1 kGy, such as about 25-400 kGy or more, preferably to about 150 kGy, wherein the finished product has no detectable free radicals. The finished product can be machined to form a medical device. The medical device can be packaged and sterilized.

In another aspect, the invention provides UHMWPE made by diffusing an antioxidant such as vitamin E, heating to a temperature above the melting point temperature, pressurizing to at least 10-1000 MPa, preferably at least 150 MPa, more preferably at least 250 MPa, holding at this temperature, cooling to about room temperature, releasing the pressure, irradiating the high pressure crystallized UHMWPE, heating to a temperature above the melting point temperature, pressurizing to at least 10-1000 MPa, preferably at least 150 MPa, more preferably at least 250 MPa, holding at this temperature, cooling to room temperature, and releasing the pressure. High pressure crystallization also can be carried out by pressurizing to at least 10-1000 MPa, preferably at least 150 MPa, more preferably at least 250 MPa, heating above 100° C. to below the melt of the pressurized polymeric material, holding at this pressure and temperature, cooling to about room temperature and releasing the pressure. According to the invention, the UHMWPE is irradiated to a dose of more than 1 kGy, such as about 25-400 kGy or more, preferably to about 150 kGy. The finished product can be machined to form a medical device. The medical device can be packaged and sterilized.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, and advantages of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

DETAILED DESCRIPTION OF THE INVENTION

The invention provides methods of making highly crystalline oxidation-resistant cross-linked polymeric material, medical implants made thereof, which comprise medical devices, including permanent and non-permanent medical devices. The invention pertains to methods of crystallizing polyethylene, such as UHMWPE, under high pressure at elevated temperature, irradiating at different temperatures, doping the cross-linked polyethylene with an antioxidant. The invention also pertains to methods of blending polyethylene with an additive, such as Vitamin E, crystallizing the blend, irradiating at different temperatures including cold irradiation below the melt and subsequent mechanical annealing.

Figure 1:
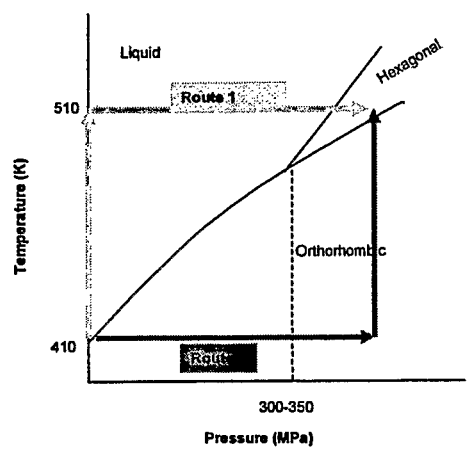
FIG. 1 shows schematically the high-pressure crystallization process and phases of polyethylene under various temperature and pressure conditions.

Polyethylene is a semi-crystalline material (55-60%) and contains folded chain crystals when crystallized from the melt under ambient pressures. The majority of the crystals are in the orthorhombic phase with lattice dimensions of 7.42, 4.95, and 2.55 Å for a, b and c dimensions, respectively. The unit cell axes are at 90° to each other. Deformation gives rise to the monoclinic phase with lattice dimensions of 8.09, 4.79, and 2.55 Å. In the hexagonal phase, which is only encountered at pressures in excess of 300 MPa (see FIG. 1, for example), the unit cell dimensions become 8.42, 4.56, and <2.55 Å. In this phase, the individual chain stems are rotated at random phase angles with respect to each other allowing for chains to slide past each other to form a densely packed structure. The crystals in this phase are termed the 'Extended Chain Crystals' (ECC) because the dense packing allows the crystals to grow to a larger extent than folded chain crystals.

It is known that the crystallinity of uncross-linked UHMWPE can be increased by high pressure and high temperature crystallization. For instance, when crystallized uncross-linked UHMWPE at pressures above 300 MPa and 180° C. to obtain the hexagonal phase transition, the peak melting point of the crystals, as determined by differential scanning calorimetry (DSC), shifted to higher temperatures and the overall crystallinity increased. Uncross-linked high pressure crystallized polyethylene with high crystallinity appeared to have higher fatigue resistance as a function of increasing crystallinity (see Baker et al., *Polymer*, 2000. 41(2): p. 795-808). Therefore, an object of the invention was to achieve a highly cross-linked (25-1000 kGy) polyethylene with high crystallinity (>51%) and good oxidation resistance.

High toughness and high fatigue strength of polymers are attributed to energy absorbing mechanisms such as cavitation and plastic deformation. The major energy absorbing mechanism in polyethylene is the plastic deformation of the crystalline domains (crystal plasticity), which depends on ductility and crystallinity. Cross-linking polyethylene with high dose levels of irradiation drastically reduces the mobility of the chains, hence reducing the overall ductility. Melting in the presence of cross-links limits the ability of the chains to reorder and hence decreases the crystallinity of polyethylene. The combination of these two factors, namely reduced chain mobility and reduced crystallinity, reduces cross-linked and melted polyethylene's fatigue resistance.

Figure 2:
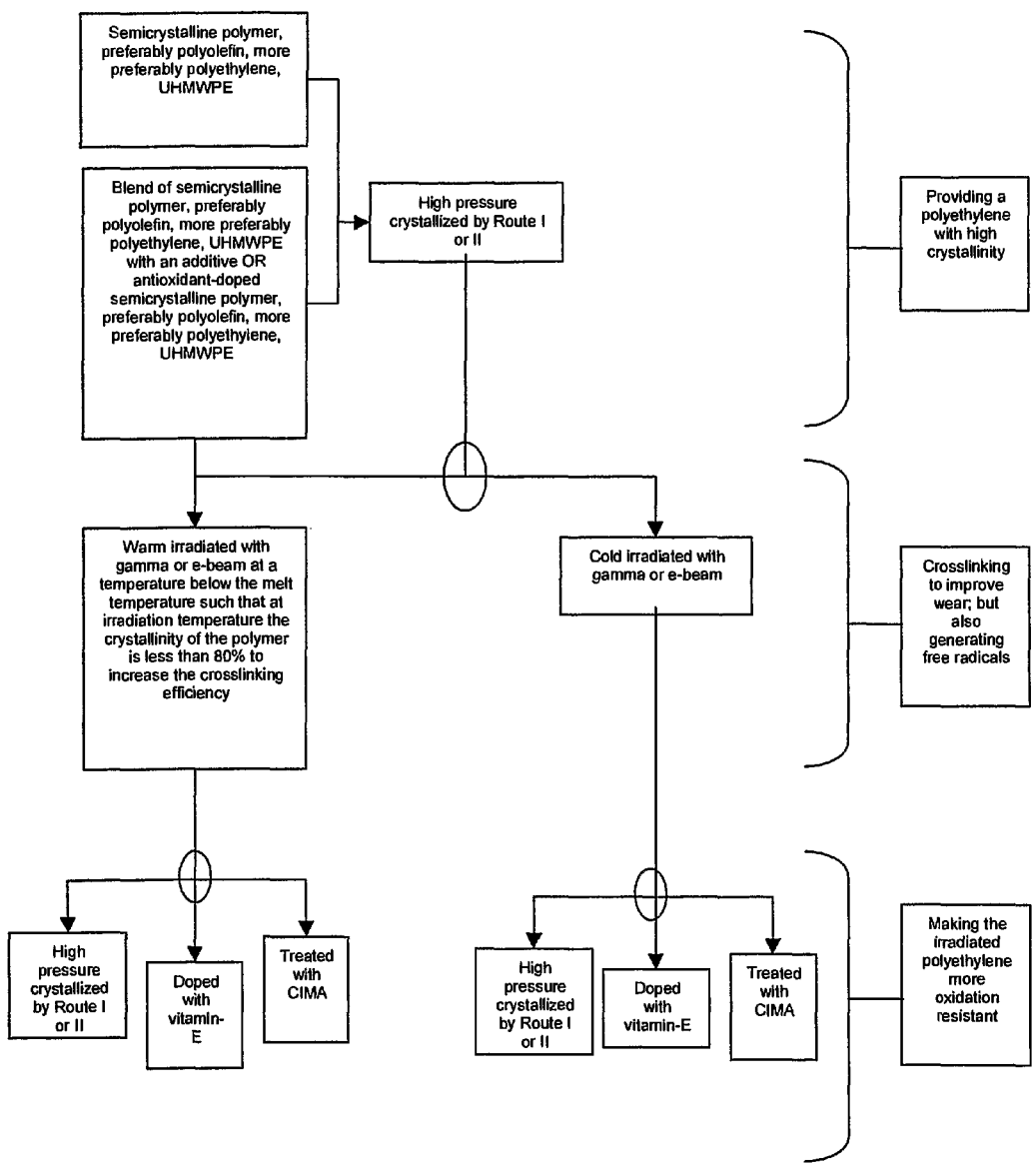
FIG. 2 schematically shows various steps and methods of making highly crystalline oxidation-resistant cross-linked polymeric material.

According to the invention, highly crystalline cross-linked oxidation-resistant polyethylene can be obtained following various processes and steps (see FIG. 2, for example), as described below, for example:

1. High pressure crystallize unirradiated/uncross-linked polyethylene using either Route I or Route II:
   A. Route I: Heat to the desired temperature, for example, above the melt (for example, about 140° C., about 180° C., about 200° C., about 250° C., or about 300° C.); then pressurize; then hold pressure at about the same pressure, for one minute to a day or more, preferably about 0.5 hours to 12 hours, more preferably 1 to 6 hours; then release the pressure (pressure has to be released after cooling down to room temperature to avoid melting of the crystals achieved under high pressure).
   B. Route II: Pressurize to the desired pressure; then heat to the desired temperature, for example, below the melt of pressurized polyethylene (for example, about 150° C., about 180° C., about 195° C., about 225° C., about 300° C., and about 320° C.); then hold pressure at about the same pressure, for one minute to a day or more, preferably about 0.5 hours to 12 hours, more preferably 1 to 6 hours; then cool to room temperature; then release the pressure (pressure has to be released after cooling down to room temperature to avoid melting of the crystals achieved under high pressure).
2. Then irradiate the high-pressure crystallized (HPC) polyethylene using either cold or warm irradiation:
   A. Cold Irradiation (CI): irradiate at between about room temperature and 90° C. using either e-beam or gamma radiation. If the crystallinity of the HPC-polyethylene is too high, there may not be enough amorphous polyethylene available for cross-linking. Therefore, it may require higher than usual dose levels, that is the dose levels required for polyethylene crystallized without high-pressure (as described herein, for example, usual dose levels of 75 kGy or 100 kGy), to achieve a desired wear resistance or crosslink density.
   B. Warm Irradiation (WI): irradiate at between about 90° C. and the peak melting point of HPC-polyethylene, which is generally around 145° C. The temperature of irradiation can be adjusted to achieve a desired extent of amorphous polyethylene during irradiation.
3. Then treat the irradiated HPC-polyethylene (I-HPC) by either one of the following methods or a combination thereof:
   A. Repeat the high-pressure crystallization following Route I or Route II, as described above.
   B. Dope with an antioxidant, such as vitamin E, which can be done by various ways, for example,
      i. machine the final product, soak in vitamin E or its solution at between room temperature and boiling point of vitamin E solution; then wash, package and sterilize with either gas plasma, ethylene oxide, or ionizing radiation, such as gamma either in air or in inert gas.
      ii. soak highly crystalline polymeric material in vitamin E or its solution at between room temperature and boiling point of vitamin E solution; machine medical implant, then wash, package and irradiate packaged medical implant to cross-link and sterilize.
   C. Treat with a CIMA (Cold Irradiation and Mechanically Annealed) method, for example,
      i. heat to a temperature between 90° C. and peak melting point of I-HPC, deform under compression to a compression ratio of above 2.5, hold deformation and cool to room temperature, anneal at a temperature between 90° C. and peak melting point of I-HPC, machine the final product, package and sterilize, preferably sterilize with ethylene oxide or gas plasma. CIMA methods can be applied as described in US Patent publication 20030149125 (U.S. application Ser. No. 10/252,582), filed Sep. 24, 2002, the entirety of which is hereby incorporated by reference.

In one aspect of the invention, the polymeric material is heated to a temperature above the melting point, for example, about 140° C., about 180° C., about 200° C., about 250° C., or about 300° C. during the Route I high pressure crystallization.

In another aspect, the polymeric material is heated to a temperature below the melting point of the pressurized polymeric material, for example, about 150° C., about 180° C., about 195° C., about 225° C., about 300° C., and about 320° C. during the Route II high pressure crystallization.

An antioxidant, which is compatible with lipophilic polyethylene, blends well with and protects irradiated polyethylene against oxidation, at radiation doses as high as 100 kGy. Moreover, antioxidant was found not to interfere with cross-linking of polyethylene, when diffused after irradiation. Therefore, cross-linked polyethylene diffused with antioxidant after irradiation showed wear rates comparable to contemporary cross-linked and melted polyethylenes. Mechanical deformation at temperatures below the melt also is an alternative approach of removing residual free radicals from irradiated polyethylene without melting.

The present invention also provides methods of crystallizing a blend of polymer with an additive under a high pressure and high temperatures and irradiating thus formed highly crystalline blend to obtain a highly crystalline, cross-linked blend of polymer and the additive. The present invention also provides methods of crystallizing a blend of polymer with additive, which is also an antioxidant, under a high pressure and high temperatures and irradiating thus formed highly crystalline blend to obtain a highly crystalline, cross-linked oxidation-resistant blend of polymer and an additive, which is also an antioxidant.

The present invention also provides methods of improving the oxidation resistance of highly crystalline cross-linked UHMWPE without melting. Melting of the highly crystalline UHMWPE will eliminate the ECC and reduce the crystallinity of the polymer. Therefore, the present invention provides the methods that use antioxidant or mechanical deformation below the melting point. According to the invention, improvement of oxidation resistance can be achieved either by doping with an antioxidant as described herein or by mechanical deformation methods. The mechanical deformation is used after irradiation to reduce the population of residual free radicals without melting the polymer, for example, uniaxially compressing to a compression ratio of at least 2.0 below the melting point (for example, less than about 150° C.) is utilized to reduce the residual free radical concentration. According to the invention, orientation and some of the thermal stresses that can persist following the mechanical deformation are reduced by further annealing at an elevated temperature below the melting point and cooling down. Following annealing, it may be desirable to cool down the polyethylene at slow enough cooling rate (for example, at about 10° C./hour) so as to minimize thermal stresses.

As described herein, it is demonstrated that mechanical deformation can eliminate residual free radicals in a radiation cross-linked UHMWPE. The invention also provides that one can first deform UHMWPE to a new shape either at solid- or at molten-state, for example, by compression. According to a process of the invention, mechanical deformation of UHMWPE when conducted at a molten-state, the polymer is crystallized under load to maintain the new deformed shape. Following the deformation step, the deformed UHMWPE sample is irradiated at a temperature below the melting point to crosslink, which generates residual free radicals. To reduce or eliminate these free radicals, the irradiated polymer specimen is heated to a temperature below the melting point of the deformed and irradiated polyethylene (for example, up to about 150° C.) to allow for the shape memory to partially recover the original shape. Generally, it is expected to recover about 80-90% of the original shape. During this recovery, the crystals undergo motion, which can help the free radical recombination and elimination. The above process is termed as a 'reverse-IBMA'. The reverse-IBMA (reverse-irradiation below the melt and mechanical annealing) technology can be a suitable process in terms of bringing the technology to large-scale production of UHMWPE-based medical devices.

In one aspect, the invention discloses medical implants, including permanent and non-permanent medical devices, comprising polymeric material having high crosslink density, high crystallinity, wear and oxidation resistance comparable with a highly cross-linked and melted polyethylene with fatigue resistance above highly cross-linked and melted polyethylene.

Medical implants, as disclosed herein can be obtained by various processes disclosed herein, for example, consolidating polymeric material; crystallizing the consolidated polymeric material under a high temperature, such as at above 150° C. and at a high pressure, such as at above 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, subsequently, cooling down to room temperature followed by reducing the pressure to ambient, subsequently heating and holding the high pressure crystallized polymeric material at a certain temperature, such as at below 150° C., so as to achieve partly amorphous polyethylene; irradiating by ionizing radiation to a dose of more than 1 kGy, such as about 25-400 kGy or more, preferably to above about 75 kGy, more preferably about 100 kGy; yet more preferably about 150 kGy; increasing the oxidation resistance by either doping with an antioxidant or decreasing the concentration of residual free radicals, for example, by mechanical deformation and annealing and/or crystallizing under high pressure and temperature.

Crystallization under high pressure can be done by first melting the polyethylene at low pressure, subsequently pressurizing to above 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, and cooling to about room temperature; or by first pressurizing to above 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, then increasing the temperature until orthorhombic to hexagonal phase transition occurs, then cooling down and depressurizing.

The holding time in the melt, the holding time under pressure, the ultimate temperature and pressure and the cooling rate can be changed to obtain the highest crystallinity and a roughly equal amount of extended and folded chain crystals.

The temperature at which the folded chain crystals of the high pressure crystallized polyethylene are melted and the holding time at the temperature can be changed to obtain a desired ratio of extended to folded chain crystals and amorphous content.

Irradiation cross-links the high pressure crystallized polyethylene and provides wear resistance. Irradiation can be done at room temperature or at elevated temperatures below the melting point of polyethylene. Irradiation can be done in air, in vacuum, or in oxygen-free environment, including inert gases such as nitrogen or noble gases. Irradiation can be done by using electron-beam, gamma irradiation, or x-ray irradiation.

The adverse oxidative effects of residual free radicals caused by ionizing radiation are reduced by diffusing an antioxidant such as α-tocopherol into high pressure crystallized, partially melted and cross-linked polyethylene. The antioxidant prevents oxidation of irradiated materials. Doping of polyethylene by an antioxidant is performed as described herein.

The adverse oxidative effects of residual free radicals caused by ionizing radiation is reduced by using a blend of polymer and additive, which is also an antioxidant, such as α-tocopherol to high pressure crystallize and irradiate.

In another aspect, the residual free radicals caused by ionizing radiation are removed by mechanical annealing, where the polyethylene is heated to a temperature below the melting point (less than about 150° C.), preferably 145° C., more preferably at about 140° C. and deformed mechanically to provide mobility for the residual free radicals to recombine and stabilize.

In another aspect, the residual free radicals generated during ionizing radiation is removed by heating polyethylene to melt. Melting of the irradiated polyethylene is used as part of high-pressure crystallization subsequent to irradiation.

A high crystalline polyethylene can be made by a process comprising high-pressure crystallization of unirradiated polyethylene, followed by irradiation, and elimination of the free radicals generated during the process, with minimum compromise in the crystallinity achieved.

According to one aspect of the invention, polyethylene is pressurized to above about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least 250 MPa, yet more preferably to above 320 MPa, heated to either about 180 or about 225° C., held at that temperature and that pressure, cooled to room temperature, reduced pressure to ambient, and irradiated at room temperature. Subsequently, one of the following processes can be employed in order to improve oxidation resistance of the high pressure crystallized polyethylene: a) doping the high pressure crystallized polyethylene with an antioxidant, such as vitamin E; or b) mechanically deforming the high pressure crystallized polyethylene below its melting point followed by annealing near its melting point, essentially applying any of the CIMA methods, and c) heating to above the melting point, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least 250 MPa, yet more preferably above 320 MPa, holding at this temperature and pressure, cooling to about room temperature, reducing pressure to ambient.

A potential draw-back of irradiating a highly crystalline polyethylene at room temperature can be that the reduced concentration of amorphous phase, where cross-linking primarily takes place, in a polyethylene with increased crystallinity can also reduce the concentration of crosslinks formed by irradiation. Therefore, it is preferable to irradiate polyethylene at an elevated temperature where the polymer is approximately 60% or less crystalline to increase the amorphous content. High pressure crystallized polyethylene exhibits two melting peaks, one at about 137° C. and the other at above about 140° C. The second peak is formed during high-pressure crystallization and represents extended chain crystals (larger ones). The following sequence of events is applied according to one aspect of the invention: Heated to a temperature below 140° C. to melt some of the smaller crystals and also cross-linked the regions that contain smaller crystals; irradiated at this temperature (warm irradiation (WI)), then one of the following processes are employed in order to improve oxidation resistance of the high pressure crystallized polyethylene:

a) doping the high-pressure crystallized polyethylene with an antioxidant, such as vitamin E;

b) mechanically deforming the high-pressure crystallized polyethylene below its melting point followed by annealing near its melting point, essentially applying any of the CIMA methods; and c) melt by heating to above the melting point, then pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least 250 MPa, yet more preferably above 320 MPa, holding pressure and temperature about constant, cooling to about room temperature, and reducing pressure to ambient. The melting step of this process will eliminate the crystals; therefore, the process is followed by high-pressure crystallization to achieve a high level of crystallinity.

In one aspect of the invention, the doping of high pressure crystallized polyethylene can be carried out by diffusion of an antioxidant, for example, $\alpha$-tocopherol, such as vitamin E. According to one aspect of the invention, diffusion of the antioxidant is accelerated by increasing the temperature and/or pressure.

According to another aspect of the invention, an antioxidant is delivered in various forms, including in a pure form, for example, as pure vitamin E, or dissolved in a solvent.

According to another aspect of the invention, the diffusion rate of an antioxidant into the polyethylene is increased by increasing the concentration of the antioxidant solution, for example, a vitamin E solution.

In accordance with another aspect of the invention, diffusion rate of an antioxidant into the polyethylene is increased by swelling the high pressure crystallized polyethylene in a supercritical fluid, for example, in a supercritical $CO_2$, i.e., the temperature being above the supercritical temperature, which is 31.3° C., and the pressure being above the supercritical pressure, which is 73.8 bar.

In general, for example, in case of vitamin E, as the antioxidant, mixing the resin powder, flakes, particles, or a mixture thereof, with vitamin E and consolidation thereafter result in changes in color of polymeric material to yellow. According to one of aspect of the instant invention, doping subsequent to consolidation avoids the exposure of vitamin E to high temperatures and pressures of consolidation and prevents the discoloration of the polymeric material.

Doping in the consolidated state also allows one to achieve a gradient of antioxidant in consolidated polymeric material. One can dope a certain thickness surface layer where the oxidation of the polymeric material in a medical device is of concern in terms of wear. This can be achieved by simply dipping or soaking finished devices, for example, a finished medical implant, for example, in pure vitamin E or in a solution of vitamin E at a given temperature and for a given amount of time.

According to the methods described herein, an antioxidant, for example, vitamin E, can be doped into the high-pressure crystallized polymeric material before, during, or after irradiation.

It may be possible that the doped antioxidant can leach out of the polymeric material used in fabrication of medical implants or medical devices either during storage prior to use or during in vivo service. For a permanent medical device, the in vivo duration can be as long as the remaining life of the patient, which is the length of time between implantation of the device and the death of the patient, for example, 1-120 years. If leaching out of the antioxidant is an issue, the irradiation of the medical implant or medical device or irradiation of any portion thereof can be carried out after doping the antioxidant. This can ensure cross-linking of the antioxidant to the host polymer through covalent bonds and thereby minimize or prevent loss of antioxidant from the medical implant or the device.

According to another aspect of the invention, antioxidant-doped polymeric material or an antioxidant-doped medical implant can be washed in an industrial washer with detergent before packaging and sterilization. An industrial washer, for example, a washer/dryer such as a HAMO T-21 or a washer/disinfectant/dryer such as a HAMO M-100 (HAMO AG, Pieterlen, Switzerland) can be used.

According to another aspect of the invention, antioxidant-doped polymeric material; or an antioxidant-doped medical implant can be soaked in a solvent such as ethanol before packaging and sterilization. A solvent, in which the antioxidant dissolves, is chosen so that the cleaning environment can provide a conducive environment for removing the antioxidant from the polymeric material. This decreases the possibility of antioxidant leaching from the antioxidant-doped polymeric material. The solvent can be at room temperature or at elevated temperatures, under ambient pressure or under elevated pressures, still or stirred. The time for the antioxidant-doped polymeric material or medical implant in contact with the solvent can range from about an hour to at least as long as the time that the doping was done, preferably less than 16 hours.

According to another aspect of the invention, polymeric material, for example, resin powder, flakes, particles, or a mixture thereof, is mixed with an antioxidant and then the mixture is consolidated. The consolidated antioxidant doped polymeric material (blend) can be machined to use as a component in a medical implant or as a medical device.

According to another aspect of the invention, high-pressure crystallized polymeric material, for example, high pressure crystallized resin powder, molded sheet, blown films, tubes, balloons, flakes, particles, or a mixture thereof, can be doped with an antioxidant, for example, vitamin E in the form of $\alpha$-Tocopherol, by diffusion. High pressure crystallized polymeric material, for example, high pressure crystallized UHMWPE can be soaked in 100% vitamin E or in a solution of $\alpha$-Tocopherol in an alcohol, for example, ethanol or isopropanol. A solution of $\alpha$-Tocopherol, about 50% by weight in ethanol can be used to diffuse in to UHMWPE in contact with a supercritical fluid, such as $CO_2$.

The invention also relates to the following processing steps to fabricate medical devices made out of highly cross-linked polyethylene and containing metallic pieces such as bipolar hip replacements, tibial knee inserts with reinforcing metallic and polyethylene posts, intervertebral disc systems; and for any implant that contains a surface that cannot be readily sterilized by a gas sterilization method.

According to one aspect of the invention, the high pressure crystallized polyethylene component of a medical implant is in close contact with another material (that is a non-modular implant), such as a metallic mesh or back, a non-metallic mesh or back, a tibial tray, a patella tray, or an acetabular shell, wherein the polyethylene, such as resin powder, flakes and particles are directly compression molded to these counter faces. For example, a polyethylene tibial insert is manufactured by compression molding of polyethylene resin powder to a tibial tray, to a metallic mesh or back or to a non-metallic mesh or back. In the latter case, the mesh is shaped to serve as a fixation interface with the bone, through either bony ingrowth or the use of an adhesive, such as polymethylmethacrylate (PMMA) bone cement. These shapes are of various forms including, acetabular liner, tibial tray for total or unicompartmental knee implants, patella tray, and glenoid component, ankle, elbow or finger component. Another aspect of the invention relates to mechanical interlocking of the molded polyethylene with the other piece(s), for example, a metallic or a non-metallic piece, that makes up part of the implant. The consolidated polyethylene with metallic piece is then high-pressure crystallized (HPC) to achieve a highly crystalline polyethylene. The HPC can is carried out by either first heating or pressurizing the non-modular implant.

The interface geometry is crucial in that polyethylene assumes the geometry as its consolidated shape. Polyethylene has a remarkable property of 'shape memory' due to its very high molecular weight that results in a high density of physical entanglements. Following consolidation, plastic deformation introduces a permanent shape change, which attains a preferred high entropy shape when melted. This recovery of the original consolidated shape is due to the 'shape memory', which is achieved when the polyethylene is consolidated. Because of this shape memory, the mechanical interlock will remain intact-during and after the high-pressure crystallization of the non-modular implant.

Another aspect of the invention provides that following the high-pressure crystallization of the polyethylene that was molded to the counterface with the mechanical interlock, the hybrid component is irradiated using ionizing radiation to a desired dose level, for example, about 25 kGy to about 1000 kGy, preferably between about 50 kGy and about 150 kGy. Another aspect of the invention discloses that the irradiation step generates residual free radicals and therefore, a melting step is introduced thereafter to quench the residual free radicals followed by another step of high-pressure crystallization. Since the polyethylene is first consolidated into the shape of the interface, thereby setting a 'shape memory' of the polymer, the polyethylene does not separate from the counterface during melting and subsequent high-pressure crystallization step.

In another aspect of the invention, there are provided methods of cross-linking polyethylene, to create a polyethylene-based medical device, wherein the device is immersed in an oxidation-resistant medium such as inert gas or inert fluid, wherein the medium is heated to above the melting point of the irradiated highly crystalline polyethylene, for example, high pressure crystallized UHMWPE (above about 140° C.) to eliminate the crystalline matter and to allow the recombination/elimination of the residual free radicals. Because the shape memory of the compression molded polymer is set at the mechanically interlocked interface and that memory is strengthened by the cross-linking step, there is no significant separation at the interface between the polyethylene and the counterface.

Another aspect of the invention provides that following the above steps of free radical elimination, the interface between the metal and the polymer become sterile due to the high irradiation dose level used during irradiation. When there is substantial oxidation on the outside surface of the HPC-polyethylene induced during the free radical elimination step or irradiation step, the device surface can be further machined to remove the oxidized surface layer. In another aspect, the invention provides that in the case of a post-melting machining of an implant, the melting step can be carried out in the presence of an inert gas.

Another aspect of the invention includes methods of sterilization of the fabricated device, wherein the device is further sterilized with ethylene oxide, gas plasma, or the other gases, when the interface is sterile but the rest of the component is not.

Irradiation of a Finished Product Made of a Blend of UHMWPE with an Additive Followed by High-Pressure Crystallization:

According to one aspect of the invention, a finished product, for example, an article, a medical device, or a medical prosthesis and the like, is irradiated and then high pressure crystallized as follows: Polymeric material, for example, resin powder, flakes, particles, or a mixture thereof, is mixed/blended with an additive, for example, an antioxidant, preferably vitamin E (preferably less than about 10%, more preferably less than 5%, more preferably less than 0.3%, and yet more preferably 0.1% vitamin E) and then form an article or a medial device by:
 a. Consolidating the blend, preferably by adding a step to anneal the consolidated blend to remove thermal stresses; and
 b. Machining the blend to form a finished product; or
 c. Direct compression molding the blend to form a finished product.

The finished product is irradiated to at least 1 kGy, preferably about 25 kGy to about 1000 kGy or more, more preferably a dose of about 25, 50, 75, 100, 125, 150, 175, or 200 kGy by gamma, e-beam, or x-ray.

The irradiated finished product is high pressure crystallized by either:
 a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
 b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Irradiation of a Finished Product Made of a Blend of UHMWPE with an Additive Followed by High-Pressure Crystallization:

According to one aspect of the invention, a finished product, for example, an article, a medical device, or a medical prosthesis and the like, is irradiated and then high pressure crystallized as follows: Polymeric material, for example, resin powder, flakes, particles, or a mixture thereof, is mixed/blended with an additive, for example, an antioxidant, preferably vitamin E (preferably less than about 10%, more preferably less than 5%, more preferably less than 0.3%, and yet more preferably 0.1% vitamin E) and then form an article or a medial device by:
 a. Doping the polymeric material with an antioxidant by diffusion; and
 b. Machining the blend to form a finished product; or
 c. Direct compression molding the blend to form a finished product.

The finished product is irradiated to at least 1 kGy, preferably about 25 kGy to about 1000 kGy or more, more preferably a dose of about 25, 50, 75, 100, 125, 150, 175, or 200 kGy by gamma, e-beam, or x-ray.

The irradiated finished product is high pressure crystallized by either:
 a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
 b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Irradiation of a Finished Product Made of a Blend of UHMWPE with an Additive Followed by High-Pressure Crystallization:

According to one aspect of the invention, a finished product, for example, an article, a medical device, or a medical prosthesis and the like, is irradiated and then high pressure crystallized as follows: Polymeric material, for example, resin powder, flakes, particles, or a mixture thereof, is mixed/blended with an additive, for example, an antioxidant, preferably vitamin E (preferably less than about 10%, more preferably less than 5%, more preferably less than 0.3%, and yet more preferably 0.1% vitamin E) and then form an article or a medial device by:
 a. Machining the blend to form a finished product; or
 b. Direct compression molding the blend to form a finished product; and
 c. Doping the finished product with an antioxidant by diffusion.

The finished product is irradiated to at least 1 kGy, preferably about 25 kGy to about 1000 kGy or more, more preferably a dose of about 25, 50, 75, 100, 125, 150, 175, or 200 kGy by gamma, e-beam, or x-ray.

The irradiated finished product is high pressure crystallized by either:
 a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
 b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Irradiation, Melting, and Machining of a Finished Product Prior to High-Pressure Crystallization:

According to another aspect of the invention, a finished product, for example, an article, a medical device or a medical prosthesis and the like, is irradiated, melted, machined, and then high pressure crystallized as follows:

Polymeric material is irradiated, melted, and machined to form a finished product, for example, an article, a medical device, or a medical prosthesis and the like.

The finished product is high pressure crystallized by either:
 a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
 b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Irradiation and Machining of a Finished Product Prior to High-Pressure Crystallization:

According to another aspect of the invention, a finished product, for example, an article, a medical device or a medical prosthesis and the like, is irradiated, machined and then high pressure crystallized as follows:

Polymeric material is irradiated and machined to form a finished product, for example, an article, a medical device, or a medical prosthesis and the like.

The finished product is high pressure crystallized by either:
 a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
 b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Warm Irradiation, Melting, and Machining of a Finished Product Prior to High-Pressure Crystallization:

According to another aspect of the invention, a finished product, for example, an article, a medical device or a medical prosthesis and the like, is warm irradiated, melted, machined, and then high pressure crystallized as follows:

Polymeric material is warm irradiated to above room temperature, such as a temperature above about 80° C. and below the melting point of the polymeric material. The warm irradiated polymeric material is melted, and machined to form a finished product, for example, an article, a medical device, or a medical prosthesis and the like.

The finished product is high pressure crystallized by either:
a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Warm Irradiation and Machining of a Finished Product Prior to High-Pressure Crystallization:

According to another aspect of the invention, a finished product, for example, an article, a medical device or a medical prosthesis and the like, is warm irradiated, machined, and then high pressure crystallized as follows:

Polymeric material is warm irradiated to above room temperature, such as a temperature above about 80° C. and below the melting point of the polymeric material and machined to form a finished product, for example, an article, a medical device, or a medical prosthesis and the like.

The finished product is high pressure crystallized by either:
a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
b. Pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Cold Irradiation and Mechanically Annealing (CIMA) and Machining of a Finished Product Prior to High-Pressure Crystallization:

According to another aspect of the invention, a finished product, for example, an article, a medical device or a medical prosthesis and the like, is irradiated by a CIMA method, machined, and then high pressure crystallized as follows:

Polymeric material is irradiated and mechanically deformed at an elevated temperature, such as above 90° C. and below 140° C. and deformed under pressure until cooled down to room temperature, annealed above room temperature, such as at above 90° C. and below 140° C. to recover the deformed state, and machined to form a finished product, for example, an article, a medical device, or a medical prosthesis and the like.

The finished product is high pressure crystallized by either:
a. Heating to a temperature above the melting point of the irradiated polyethylene under an ambient pressure, pressurizing to at least about 10-1000 MPa (for example, at least about 150 MPa, 200 MPa, 250 MPa, 310 MPa, 300 MPa, 320 MPa, 400 MPa, or 450 MPa), preferably at least about 150 MPa, more preferably at least about 250 MPa, cooling to about room temperature while under pressure, and releasing the pressure; or
b. Pressurizing to at least about 10-1000 MPa (for example, at least about 150 MPa, 200 MPa, 250 MPa, 310 MPa, 300 MPa, 320-MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Definitions:

"High pressure crystallized" (HPC) refers to a state of a polymeric material that has undergone high-pressure crystallization process, according to the invention, as described herein.

"High-pressure crystallization" refers to a method of making high pressure crystallized polyethylene, according to the invention, as described herein.

The term "highly crystalline" or "high crystallinity" refers to a state of a material of at least about 51% crystallinity.

"Antioxidant" refers to what is known in the art as (see, for example, WO 01/80778, U.S. Pat. No. 6,448,315). Alpha- and delta-tocopherol; propyl, octyl, or dedocyl gallates; lactic, citric, and tartaric acids and their salts; orthophosphates, tocopherol acetate. Preferably vitamin E.

"Supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar. More specifically, supercritical condition refers to a condition of a mixture, for example, UHMWPE with an antioxidant, at an elevated temperature and pressure, when a supercritical fluid mixture is formed and then evaporate $CO_2$ from the mixture, UHMWPE doped with an antioxidant is obtained (see, for example, U.S. Pat. No. 6,448,315 and WO 02/26464)

The term "compression molding" as referred herein related generally to what is known in the art and specifically relates to high temperature molding polymeric material wherein polymeric material is in any physical state, including powder form, is compressed into a slab form or mold of a medical implant, for example, a tibial insert, an acetabular liner, a glenoid liner, a patella, or an unicompartmental insert.

The term "direct compression molding" as referred herein related generally to what is known in the art and specifically relates to molding applicable in polyethylene-based devices, for example, medical implants wherein polyethylene in any physical state, including powder form, is compressed to solid support, for example, a metallic back, metallic mesh, or metal surface containing grooves, undercuts, or cutouts. The compression molding also includes high temperature compression molding of polyethylene at various states, including resin powder, flakes and particles, to make a component of a medical implant, for example, a tibial insert, an acetabular liner, a glenoid liner, a patella, or an unicompartmental insert, to the counterface.

The term "mechanically interlocked" refers generally to interlocking of polyethylene and the counterface, that are produced by various methods, including compression molding, heat and irradiation, thereby forming an interlocking interface, resulting into a 'shape memory' of the interlocked polyethylene. Components of a device having such an interlocking interface can be referred to as a "hybrid material". Medical implants having such a hybrid material, contain a substantially sterile interface.

The term "substantially sterile" refers to a condition of an object, for example, an interface or a hybrid material or a medical implant containing interface(s), wherein the interface is sufficiently sterile to be medically acceptable, i.e., will not cause an infection or require revision surgery.

"Metallic mesh" refers to a porous metallic surface of various pore sizes, for example, 0.1-3 mm. The porous surface can be obtained through several different methods, for example, sintering of metallic powder with a binder that is subsequently removed to leave behind a porous surface; sintering of short metallic fibers of diameter 0.1-3 mm; or sintering of different size metallic meshes on top of each other to provide an open continuous pore structure.

"Bone cement" refers to what is known in the art as an adhesive used in bonding medical devices to bone. Typically, bone cement is made out of polymethylmethacrylate (PMMA).

"High temperature compression molding" refers to the compression molding of polyethylene in any form, for example, resin powder, flakes or particles, to impart new geometry under pressure and temperature. During the high temperature (above the melting point of polyethylene) compression molding, polyethylene is heated to above its melting point, pressurized into a mold of desired shape and allowed to cool down under pressure to maintain a desired shape.

"Shape memory" refers to what is known in the art as the property of polyethylene, for example, an UHMWPE, that attains a preferred high entropy shape when melted. The preferred high entropy shape is achieved when the resin powder is consolidated through compression molding.

The phrase "substantially no detectable residual free radicals" refers to a state of a polyethylene component, wherein enough free radicals are eliminated to avoid oxidative degradation, which can be evaluated by electron spin resonance (ESR). The phrase "detectable residual free radicals" refers to the lowest level of free radicals detectable by ESR. The lowest level of free radicals detectable with state-of-the-art instruments is about $10^{14}$ spins/gram and thus the term "detectable" refers to a detection limit of $10^{14}$ spins/gram by ESR.

The terms "about" or "approximately" in the context of numerical values and ranges refers to values or ranges that approximate or are close to the recited values or ranges such that the invention can perform as intended, such as having a desired degree of crystallinity or cross-linking and/or a desired lack of free radicals, as is apparent to the skilled person from the teachings contained herein. This is due, at least in part, to the varying properties of polymer compositions. Thus these terms encompass values beyond those resulting from systematic error.

Polymeric Material:

Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, PCT/US97/02220, filed Feb. 11, 1997, and US Patent publication 20030149125 (U.S. application Ser. No. 10/252,582), filed Sep. 24, 2002.

The products and processes of this invention also apply to various types of polymeric materials, for example, any polyolefin, including high-density-polyethylene, low-density-polyethylene, linear-low-density-polyethylene, ultra-high molecular weight polyethylene (UHMWPE), or mixtures thereof. Polymeric materials, as used herein, also applies to polyethylene of various forms, for example, resin powder, flakes, particles, powder, or a mixture thereof, or a consolidated form derived from any of the above.

The term "additive" refers to any material that can be added to a base polymer in less than 50 v/v %. This material can be organic or inorganic material with a molecular weight less than that of the base polymer. An additive can impart different properties to the polymeric material, for example, it can be a plasticizing agent, a nucleating agent, or an antioxidant.

"Blending" generally refers to mixing of a polyolefin in its pre-consolidated form with an additive. If both constituents are solid, blending can be done by using a third component such as a liquid to mediate the mixing of the two components, after which the liquid is removed by evaporating. If the additive is liquid, for example (X-tocopherol, then the solid can be mixed with large quantities of liquid, then diluted down to desired concentrations with the solid polymer to obtain uniformity in the blend. In the case where an additive is also an antioxidant, for example vitamin E, or α-tocopherol, then blended polymeric material is also antioxidant-doped. Polymeric material, as used herein, also applies to blends of a polyolefin and a plasticizing agent, for example a blend of UHMWPE resin powder blended with α-tocopherol and consolidated. Polymeric material, as used herein, also applies to blends of an additive, a polyolefin and a plasticizing agent, for example UHMWPE soaked in α-tocopherol.

"Plasticizing agent" refers to a what is known in the art, a material with a molecular weight less than that of the base polymer, for example α-tocopherol in polyethylene or low molecular weight polybutadiene in polyethylene, in both cases polyethylene being the base polymer. The plasticizing agent is typically added to the base polymer in less than about 20 weight percent. The plasticizing agent increases flexibility and softens the polymeric material.

The term "plasticization" or "plasticizing" refers to the properties that a plasticizing agent imparts on the polymeric material into which it has been added. There properties may include but are not limited to increased elongation at break, reduced stiffness, and increased ductility.

A "nucleating agent' refers to an additive known in the art, an organic or inorganic material with a molecular weight less than that of the base polymer, which increases the rate of crystallization in the polymeric material. Typically, organo-carboxylic acid salts, for example calcium carbonate, are good nucleation agents for polyolefins. Also, nucleating agents are typically used in small concentrations such as 0.5 wt %.

Doping:

Doping refers to a process well known in the art (see, for example, U.S. Pat. Nos. 6,448,315 and 5,827,904). In this connection, doping generally refers to contacting a polymeric material with an antioxidant under certain conditions, as set forth herein, for example, doping UHMWPE with an antioxidant under supercritical conditions. "Doping" also refers to introducing a second component into the base polymeric material in quantities less than 50 v/v %. More specifically, doping refers to introducing an antioxidant into a polymeric material, most often by diffusion of the antioxidant from a surrounding media into the polymeric material. A polymeric material treated in such a way is termed as "antioxidant-doped" polymeric material. However, the process of doping an antioxidant into a polymeric material is not limited to the diffusion process. The polymeric material can be 'doped'; however, by other additives as well, such as a plasticizing agent, in which case the polymeric material treated in such a way may be termed as 'plasticizing agent-doped'.

More specifically, for example, HPC polymeric material can be doped with an antioxidant by soaking the material in a solution of the antioxidant. This allows the antioxidant to diffuse into the polymer. For instance, the material can be soaked in 100% antioxidant. The material also can be soaked in an antioxidant solution where a carrier solvent can be used to dilute the antioxidant concentration. To increase the depth of diffusion of the antioxidant, the material can be doped for longer durations, at higher temperatures, at higher pressures, and/or in presence of a supercritical fluid.

The doping process can involve soaking of a polymeric material, medical implant or device with an antioxidant, such as vitamin E, for about an hour up to several days, preferably for about one hour to 24 hours, more preferably for one hour to 16 hours. The antioxidant can be heated to room temperature or up to about 160° C. and the doping can be carried out at room temperature or up to about 160° C. Preferably, the antioxidant can be heated to 10° C. and the doping is carried out at 10° C.

To further increase the uniformity of antioxidant in the base polymeric material, the doped polymeric material is annealed below or above the melt. The annealing is preferably for about an hour up to several days, more preferably for about one hour to 24 hours, most preferably for one hour to 16 hours. The doped polymeric material can be heated to room temperature or up to about 160° C. and the annealing can be carried out at room temperature or up to about 160° C. Preferably, the doped polymeric material can be heated to 100° C. and the annealing is carried out at 100° C.

The term "conventional UHMWPE" refers to commercially available polyethylene of molecular weights greater than about 500,000. Preferably, the UHMWPE starting material has an average molecular weight of greater than about 2 million.

By "initial average molecular weight" is meant the average molecular weight of the UHMWPE starting material, prior to any irradiation.

Cross-Linking Polymeric Material:

Polymeric Materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE can be obtained according to the teachings of U.S. Pat. No. 5,879,400, PCT/US99/16070, filed on Jul. 16, 1999, PCT/US97/02220, filed Feb. 11, 1997, US Patent Publication 20030149125 (U.S. application Ser. No. 10/252,582), filed Sep. 24, 2002, and U.S. Pat. No. 6,641,617, the entirety of which are hereby incorporated by reference.

Consolidated Polymeric Material:

Consolidated polymeric material refers to a solid, consolidated bar stock, solid material machined from stock, or semi-solid form of polymeric material derived from any forms as described herein, for example, resin powder, flakes, particles, or a mixture thereof, that can be consolidated. The consolidated polymeric material also can be in the form of a slab, block, solid bar stock, machined component, film, tube, balloon, pre-form, implant, or finished medical device.

By "crystallinity" is meant the fraction of the polymer that is crystalline. The crystallinity is calculated by knowing the weight of the sample (weight in grams), the heat absorbed by the sample in melting (E, in J/g) and the heat of melting of polyethylene crystals ($\Delta H=291$ J/g), and using the following equation:

$$\% \text{ Crystallinity} = E/w \cdot \Delta H$$

By tensile "elastic modulus" is meant the ratio of the nominal stress to corresponding strain for strains as determined using the standard test ASTM 638 M III and the like or their successors.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

"Permanent device" refers to what is known in the art that is intended for implantation in the body for a period longer than several months. Permanent devices include medical devices, for example, ace tabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts.

"Pharmaceutical compound", as described herein, refers to a drug in the form of a powder, suspension, emulsion, particle, film, cake, or molded form. The drug can be free-standing or incorporated as a component of a medical device.

The term "pressure chamber" refers to a vessel or a chamber in which the interior pressure can be raised to levels above atmospheric pressure.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "heat-shrinkable packaging" refers to plastic films, bags, or tubes that have a high degree of orientation in them. Upon application of heat, the packaging shrinks down as the oriented chains retract, often wrapping tightly around the medical device.

"Melt transition temperature" refers to the lowest temperature at which all the crystalline domains in a material disappear.

"Melting point" refers to the peak melting temperature measured by a differential scanning calorimeter at a heating rate of 10° C. per minute when heating from 200° C. to 220° C.

Medical implants containing factory-assembled pieces that are in close contact with the polyethylene form interfaces. In most cases, the interfaces are not readily accessible to EtO gas or the GP during a gas sterilization process.

Irradiation:

In one aspect of the invention, the type of radiation, preferably ionizing, is used. According to another aspect of the invention, a dose of ionizing radiation ranging from about 25 kGy to about 1000 kGy is used. The radiation dose can be about 50 kGy, about 65 kGy, about 75 kGy, about 100 kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any integer or fractional value thereabout or therebetween. Preferably, the radiation dose can be between about 50 kGy and about 200 kGy. These types of radiation, including x-ray, gamma and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any integer thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a vacuum.

In accordance with a preferred feature of this invention, the irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

Metal Piece:

In accordance with the invention, the piece forming an interface with polymeric material is, for example, a metal. The metal piece in functional relation with polyethylene, according to the present invention, can be made of a cobalt chrome alloy, stainless steel, titanium, titanium alloy or nickel cobalt alloy, for example. Various metal types can also be found in U.S. Ser. No. 60/424,709, filed Nov. 8, 2002 (PCT/US03/18053, filed Jun. 10, 2003, WO 2004000159).

Non-Metallic Piece:

In accordance with the invention, the piece forming an interface with polymeric material is, for example, a non-metal. The non-metal piece in functional relation with polyethylene, according to the present invention, can be made of ceramic material, for example.

Interface:

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as, orthopedic joints and bone replacement parts, for example, hip, knee, elbow or ankle replacements. Various metal/non-metal types and interfaces also can be found in U.S. Ser. No. 60/424,709, filed Nov. 8, 2002 (PCT/US03/18053, filed Jun. 10, 2003, WO 2004000159), the entirety of which is hereby incorporated by reference.

Inert Atmosphere:

The term "inert atmosphere" refers to an environment having no more than 1% oxygen and more preferably, an oxidant-free condition that allows free radicals in polymeric materials to form cross links without oxidation during a process of sterilization. An inert atmosphere is used to avoid $O_2$, which would otherwise oxidize the medical device comprising a polymeric material, such as UHMWPE. Inert atmospheric conditions such as nitrogen, argon, helium, or neon are used for sterilizing polymeric medical implants by ionizing radiation.

Inert atmospheric conditions such as nitrogen, argon, helium, neon, or vacuum are also used for sterilizing interfaces of polymeric-metallic and/or polymeric-polymeric in medical implants by ionizing radiation.

Inert atmospheric conditions also refers to a insert gas, inert fluid, or inert liquid medium, such as nitrogen gas or silicon oil.

Anoxic Environment:

"Anoxic environment" refers to an environment containing gas, such as nitrogen, with less than 21%-22% oxygen, preferably with less than 2% oxygen. The oxygen concentration in an anoxic environment also can be at least 1%, 2%, 4%, 6%, 8%, 10%, 12% 14%, 16%, 18%, 20%, or up to about 22%, or any integer or any integer or fractional value thereabout or therebetween.

Vacuum:

The term "vacuum" refers to an environment having no appreciable amount of gas, which otherwise would allow free radicals in polymeric materials to form cross links without oxidation during a process of sterilization. A vacuum is used to avoid $O_2$, which would otherwise oxidize the medical device comprising a polymeric material, such as UHMWPE. A vacuum condition can be used for sterilizing polymeric medical implants by ionizing radiation.

A vacuum condition can be created using a commercially available vacuum pump. A vacuum condition also can be used when sterilizing interfaces of polymeric-metallic and/or polymeric-polymeric in medical implants by ionizing radiation.

Residual Free Radicals:

"Residual free radicals" refers to free radicals that are generated when a polymer is exposed to ionizing radiation such as gamma or e-beam irradiation. While some of the free radicals recombine with each other to from crosslinks, some become trapped in crystalline domains. The trapped free radicals are also known as residual free radicals.

According to one aspect of the invention, the levels of residual free radicals in the polymer generated during an ionizing radiation (such as gamma or electron beam) is preferably determined using electron spin resonance and treated appropriately to reduce the free radicals through recombination.

Sterilization:

One aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-70 kGy, or by gas sterilization with ethylene oxide or gas plasma.

Another aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-200 kGy. The dose level of sterilization is higher than standard levels used in irradiation. This is to allow cross-linking or further cross-linking of the medical implants during sterilization.

The term "alpha transition" refers to a transitional temperature and is normally around 90-95° C.; however, in the presence of a sensitizing environment that dissolves in polyethylene, the alpha transition may be depressed. The alpha transition is believed (An explanation of the "alpha transition temperature" can be found in *Anelastic and Dielectric Effects in Polymeric Solids*, pages 141-143, by N. G. McCrum, B. E. Read and G. Williams; J. Wiley and Sons, N.Y., N.Y., published 1967) to induce motion in the crystalline phase, which is hypothesized to increase the diffusion of the sensitizing environment into this phase and/or release the trapped free radicals. Heating above the alpha transition will also increase the diffusion of the additive, such as plasticizing agent or the antioxidant into the base polymer.

The term "critical temperature" corresponds to the alpha transition of the polyethylene. The term "below melting point" or "below the melt" refers to a temperature below the melting point of a polyethylene, for example, UHMWPE. The term "below melting point" or "below the melt" refers to a temperature less than 155° C., which may vary depending on the melting temperature of the polyethylene. The term "above melting point" or "above the melt" refers to a temperature above the melting point of a polyethylene, for example, UHMWPE. The term "above melting point" or "above the melt" refers to a temperature more than 145° C., which may vary depending on the melting temperature of the polyethylene. The melting temperature of the polyethylene can be, for example, 155° C., 145° C., 140° C. or 135° C., which again depends on the properties of the polyethylene being treated, for example, extended chain crystals, crystallinity, molecular weight averages and ranges, batch variations, etc. For example, "above melting point" or "above the melt" of a polymeric material under high pressure during a high-pressure crystallization process refers to a temperature at or above 150° C. The melting temperature is typically measured using a differential scanning calorimeter (DSC) at a heating rate of 100° C. per minute. The peak melting temperature thus measured is referred to as melting point and occurs, for example, at approximately 137° C. for some grades of UHMWPE. It may be desirable to conduct a melting study on the starting polyethylene material in order to determine the melting temperature and to decide upon an irradiation and annealing temperature.

The term "annealing" refers to heating the polymer below its peak melting point. Annealing time can be at least 1 minute to several weeks long. In one aspect the annealing time is about 4 hours to about 48 hours, preferably 24 to 48 hours and more preferably about 24 hours. The annealing time required to achieve a desired level of recovery following mechanical deformation is usually longer at lower annealing temperatures. "Annealing temperature" refers to the thermal condition for annealing in accordance with the invention.

The term "contacted" includes physical proximity with or touching such that the sensitizing agent can perform its intended function. Preferably, a polyethylene composition or pre-form is sufficiently contacted such that it is soaked in the sensitizing agent, which ensures that the contact is sufficient. Soaking is defined as placing the sample in a specific environment for a sufficient period of time at an appropriate temperature, for example, soaking the sample in a solution of an antioxidant. The environment is heated to a temperature ranging from room temperature to a temperature below the melting point of the material. The contact period ranges from at least about 1 minute to several weeks and the duration depending on the temperature of the environment.

The term "oxidation-resistant" refers to a state of polymeric material having an oxidation index (A. U.) of less than about 0.5 following aging polymeric materials for 5 weeks in air at 80° C. oven. Thus, an oxidation-resistant cross-linked polymeric material generally shows an A. U. of less than about 0.5 after the aging period.

"Oxidation index" refers to the extent of oxidation in polymeric material. Oxidation index is calculated by obtaining an infrared spectrum for the polymeric material and analyzing the spectrum to calculate an oxidation index, as the ratio of the areas under the 1740 cm$^{-1}$ carbonyl and 1370 cm$^{-1}$ methylene stretching absorbances after subtracting the corresponding baselines.

The term "Mechanical deformation" refers to deformation taking place below the melting point of the material, essentially 'cold-working' the material. The deformation modes include uniaxial, channel flow, uniaxial compression, biaxial compression, oscillatory compression, tension, uniaxial tension, biaxial tension, ultra-sonic oscillation, bending, plane stress compression (channel die) or a combination of any of the above. The deformation could be static or dynamic. The dynamic deformation can be a combination of the deformation modes in small or large amplitude oscillatory fashion. Ultrasonic frequencies can be used. All deformations can be performed in the presence of sensitizing gases and/or at elevated temperatures.

The term "deformed state" refers to a state of the polyethylene material following a deformation process, such as a mechanical deformation, as described herein, at solid or at melt. Following the deformation process, deformed polyethylene at a solid state or at melt is be allowed to solidify/crystallize while still maintains the deformed shape or the newly acquired deformed state.

"IBMA" refers to irradiation below the melt and mechanical annealing. "IBMA" also is referred to as "CIMA" (Cold Irradiation and Mechanically Annealed).

Sonication or ultrasonic at a frequency range between 10 and 100 kHz can be used, with amplitudes on the order of 1-50 microns. The time of sonication is dependent on the frequency and temperature of sonication. In one aspect, sonication or ultrasonic frequency ranged from about 1 second to about one week, preferably about 1 hour to about 48 hours, more preferably about 5 hours to about 24 hours and yet more preferably about 12 hours.

The invention is further described by the following examples, which do not limit the invention in any manner.

EXAMPLES

Example 1

Electron Beam Irradiation of Polyethylene for Sterilization or Cross-Linking

Blocks or rods of UHMWPE were machined into 1 cm thick pieces. These samples were irradiated using a 2.5 MeV van de Graff generator (e-beam) at Massachusetts Institute of Technology by passing under the electron beam multiple times to achieve the desired radiation dose level (approximately 12.5 kGy per pass).

Example 2

Gamma Irradiation of Polyethylene for Sterilization or Cross-Linking

Cylindrical blocks (diameter 89 mm, length larger than 50 cm) were gamma irradiated using a $Co^{60}$ source (Steris Isomedix, Northborough, Mass.). A group of these blocks were vacuum packaged prior to irradiation and packaged blocks were irradiated. Another group of blocks were packaged and irradiated under nitrogen.

Example 3

Crystallization of Polyethylene Under High Pressure with Prior Melting (Route I)

Slab-compression molded GUR 1050 was used. Cylinders (5 cm diameter and 3 cm high) were machined from these blocks and were covered with aluminum, placed in a metal-laminated thermally-sealable pouch. Vacuum was pulled inside the pouch and the pouch was sealed. The vacuum-sealed pouched sample was then placed in a pressure chamber. The samples thus packaged were heated to 180° C. in argon, held at 180° C. for at least 4 hours, and then isothermally pressurized to 320 MPa (45,000 psi). The pressure was held at about constant for 5 hours. At the completion of the pressurizing cycle, the samples were cooled to room temperature under pressure. Subsequently, the pressure was released.

Example 4

Crystallization of Polyethylene Under High Pressure Below the Melt (Route II)

Slab-compression molded GUR 1050 was used. Cylinders (5 cm diameter and 3 cm high) were machined from these blocks and were covered in aluminum, placed in a metal-laminated thermally-sealable pouch. Vacuum was pulled inside the pouch and the pouch was sealed. The vacuum-sealed pouched sample was then placed in a pressure chamber. The samples thus packaged were pressurized to 320 MPa (45,000 psi). Then the temperature was increased to below the melting temperature of the pressurized UHMWPE (180° C.) at this pressure and held for 5 hours. The samples were cooled to room temperature under a constant pressure and the pressure was then released.

Example 5

Diffusion of Antioxidant into Polyethylene

Slab-compression molded GUR 1050 UHMWPE blocks were machined into thin sections of UHMWPE (thickness=3.2 mm) These samples were placed in contact with CL-tocopherol under 0.5 atm of partial nitrogen vacuum at 132° C. for 96 hours. Then, the is samples were taken out, surfaces cleaned by wiping off antioxidant, and annealed at 132° C. under 0.5 atm of partial nitrogen/vacuum for 96 hours.

Example 6

Diffusion of Antioxidant into Polyethylene Subsequent to Irradiation (100 kGy)

Slab-compression molded GUR 1050 UHMWPE blocks were gamma irradiated to a dose of 111 kGy in nitrogen. Thin sections of UHMWPE (thickness=3.2 mm) were machined and were placed in contact with α-tocopherol under 0.5 atm of partial nitrogen vacuum at 136° C. for 96 hours. Then, the samples were taken out, surfaces cleaned by wiping off antioxidant and annealed at 136° C. under 0.5 atm of partial nitrogen/vacuum for 96 hours.

Example 7

Measurement of Antioxidant Diffusion into Polyethylene

Figure 3:
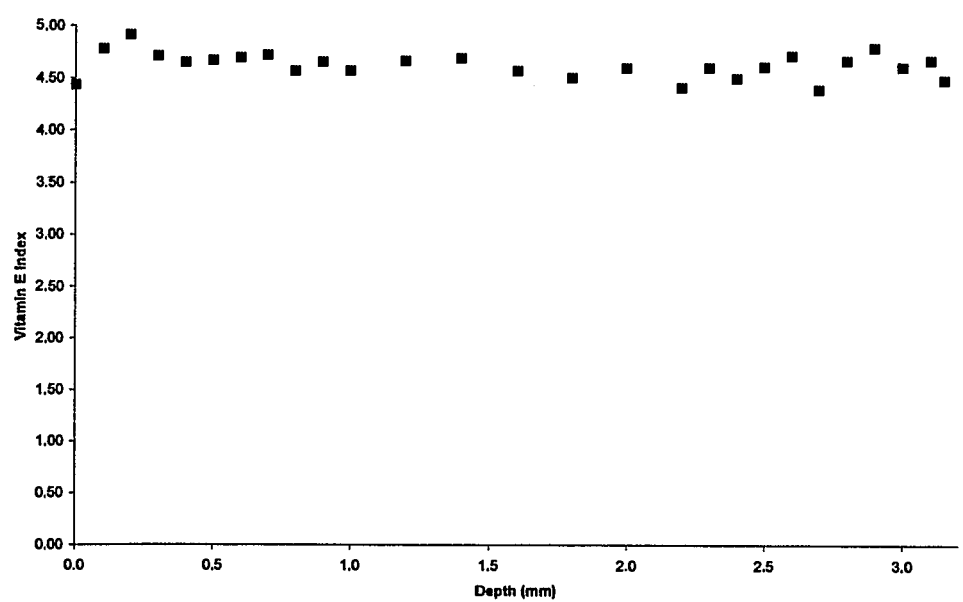
FIG. 3 shows α-tocopherol profile in UHMWPE doped for 96 hours and annealed for 96 hours at 132° C.

To measure the diffusion profile of the antioxidant in the test samples that were immersed in α-tocopherol (for example, see Examples 5 and 6), a cross-section was cut out of the immersed section (100-150 µm) using an LKB Sledge Microtome. The thin cross-section was then analyzed using a BioRad UMA 500 infrared microscope (Natick, Mass.). Infrared spectra were collected with an aperture size of 50×50 µm as a function of depth away from one of the edges that coincided with the free surface of the sample that contacted the antioxidant during immersion. The absorbance between 1226 and 1295 $cm^{-1}$ is characteristic of α-tocopherol and polyethylene does not absorb near these frequencies. For polyethylene, the 1895 $cm^{-1}$ wave number for the $CH_2$ rocking mode is a typical choice as an internal reference. The normalized value, which is the ratio of the integrated absorbances of 1260 $cm^{-1}$ and 1895 $cm^{-1}$, is an index that provides a relative metric of α-tocopherol composition in polyethylene. FIG. 3 shows the profile of α-tocopherol polyethylene doped by the procedure described in Example 5 and measured in the manner described in this example.

Example 8

Measurement of Oxidation Levels in Polyethylene

The oxidation level was quantified as a function of distance away from free surfaces on a number of UHMWPE test samples that were subjected to various processing steps as described in some of the examples below. For this, a thin cross-section (100-150 µm) of the UHMWPE test sample was cut using a LKB Sledge Microtome. A BioRad UMA 500 infrared microscope was used to measure the extent and depth of oxidation in this section. Infrared spectra were collected with an aperture size of 50×50 µm as a function of depth away from one of the edges that coincided with the free surface of the sample. The infrared spectra were analyzed to calculate an oxidation index, as the ratio of the areas under the 1740 $cm^{-1}$ carbonyl and 1370 $cm^{-1}$ methylene stretching absorbances.

Example 9

Fatigue Crack Propagation Testing

The fatigue crack propagation was quantified on a number of UHMWPE test samples that were subjected to various processing steps as described in some of the examples below. For this, fatigue crack propagation testing was performed on a MiniBionix 858 (MTS, Eden Prairie, Minn.) following ASTM E-647, the standard method for measurement of fatigue crack growth rates. Compact tension (CT) specimens of Type A1 was used, pre-cracked the notch, and conducted the tests with a stress ratio of 0.1 in a 40° C. water bath to simulate the in vivo environment.

Example 10

Bi-Directional Pin-on-Disk (Pod) Wear Testing

The wear rate was quantified on a number of UHMWPE test samples that were subjected to various processing steps as described in some of the examples below. For this, the wear behavior of the UHMWPE sample was tested using cylindrical shaped samples (9 mm diameter and 13 mm height) on a custom-built bi-directional pin-on-disk (POD) wear tester at a frequency of 2 Hz. Bovine calf serum was used as lubricant and quantified wear gravimetrically at 0.5 million-cycle intervals. Initially, the pins were subjected to 200,000 cycles of POD testing to remove reach a steady state wear rate independent of diffusion or asperities on the surface. Three pins from each group were tested for a total of 2 million cycles. The wear rate was calculated as the linear regression of wear vs. number of cycles from 0.2 to 2 million cycles.

Example 11

Determination of Crystallinity with Differential Scanning Calorimetry

The crystallinity was quantified on a number of UHMWPE test samples that were subjected to various processing steps as described in some of the examples below. For this, differential scanning calorimetry (DSC) was used to measure the crystallinity of the polyethylene test samples. The DSC specimens were weighed with a Sartorius CP 225D balance to a resolution of 0.01 milligrams and placed in an aluminum sample pan. The pan was crimped with an aluminum cover and placed in a TA instruments Q-1000 Differential Scanning Calorimeter. The samples and the reference were then heated at a heating rate of 10° C./min from −20° C. to 180° C., cooled to −10° C. and subjected to another heating cycle from −20° C. to 180° C. at 10° C./min. Heat flow as a function of time and temperature was recorded and the cycles are referred to as $1^{st}$ heat, $1^{st}$ cool and $2^{nd}$ heat, respectively.

Crystallinity was determined by integrating the enthalpy peak from 20° C. to 160° C., and normalizing it with the enthalpy of melting of 100% crystalline polyethylene, 291 J/g.

Example 12

Crystallinity Measurements of Polyethylene Following High-Pressure Crystallization by Route I Compression-molded GUR 1050 UHMWPE (also referred as conventional polyethylene) was high pressure-crystallized as described in Example 3. The control samples were compression-molded GUR 1050 UHMWPE without high-pressure crystallization. DSC test samples were prepared from these two types of polyethylenes and were analyzed using a TA Instruments Q-1000 calorimeter as described in Example 11.

Figure 4:
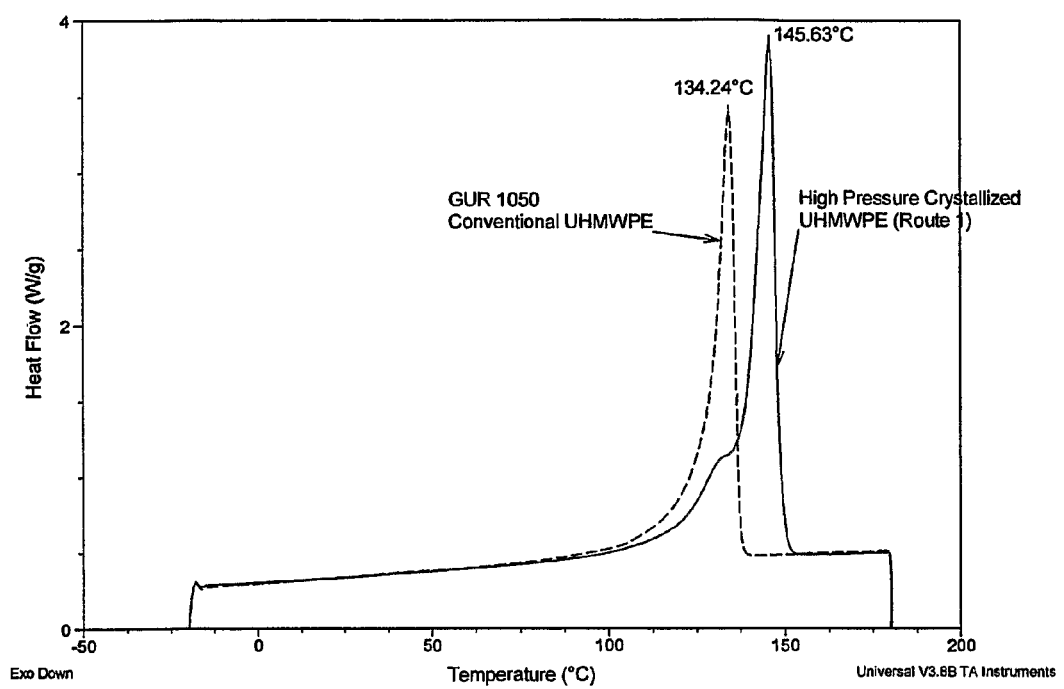
FIG. 4 depicts DSC thermograms of a conventional and a high pressure crystallized conventional unirradiated polyethylene.

The high pressure crystallized samples that were tested contained transparent and opaque sections. When a cross-section was cut out of the cylindrical blocks, the center was most often more transparent than the rim. FIG. 4 shows a representative thermogram of the heating cycle of conventional polyethylene with no high-pressure crystallization history and a section from the center of high pressure crystallized conventional polyethylene. The $1^{st}$ heat crystallinity of the conventional polyethylene was 62% with a peak melting temperature of 134° C. The high pressure crystallized polyethylene showed a $1^{st}$ heat is crystallinity of 78% with the peak melting temperature at 145° C. and a shoulder at 130° C.

The high-pressure crystallization parameters used here resulted in an increase in the crystallinity of the conventional polyethylene. In addition, the shift of the peak melting temperature from 134° C. to 145° C. indicated the formation of larger crystals (extended chain crystals) during high-pressure crystallization.

Figure 5:
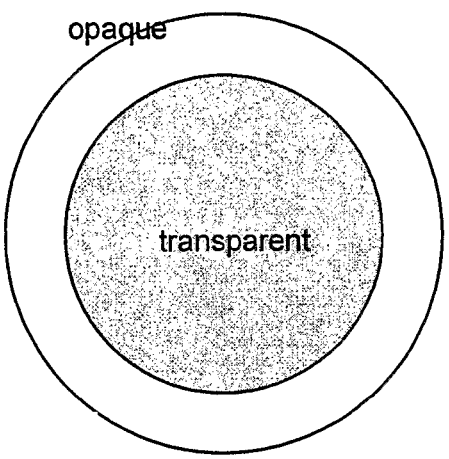
FIG. 5 shows an optical micrograph of a cylindrical cross-section of a high pressure crystallized conventional polyethylene.
Figure 5:
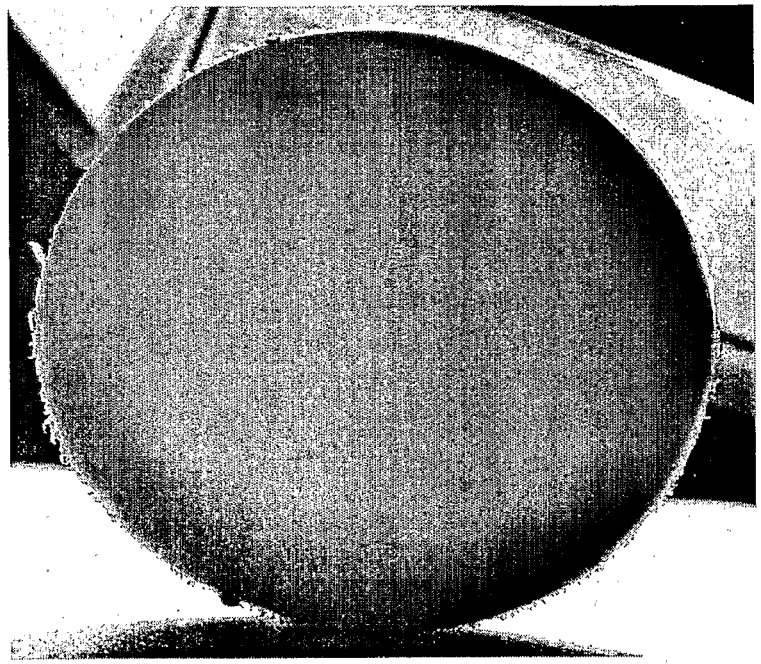

As discussed above, the high pressure crystallized cylinder of conventional polyethylene radially exhibited a non-uniform appearance (as shown schematically in FIG. 5). Variations in the crystallinity with the appearance of the polyethylene are shown in Table 1. A core with a diameter of approximately 2 cm showed high crystallinity. The crystallinity decreased towards the rim. At the opaque rim, the crystallinity was not significantly different from that of conventional polyethylene, which may be due to the pressurization medium (argon gas) diffusing into the outer layer of polyethylene and swelling. The swelling may have resulted in cavitation in polyethylene. Cavitation is known to scatter light and hence, make the polyethylene appear opaque.

TABLE 1

Crystallinity of conventional polyethylene and high pressure crystallized (HPC) conventional polyethylene.

| Material | Crystallinity (%) |
| --- | --- |
| Conventional polyethylene | 61.8 ± 1.4 |
| HPC conventional polyethylene, transparent | 77.7 ± 1.3 |
| HPC conventional polyethylene, opaque | 61.3 ± 2.6 |

Example 13

Crystallinity Measurements of Previously Irradiated and Melted Polyethylene Following High-Pressure Crystallization by Route I Compression-molded GUR 1050 was e-beam irradiated to 95 kGy at 120° C. and subsequently melted (WIAM-95). A cylindrical block (diameter 50 mm, length approximately 40 mm) was high pressure crystallized by Route I as described in Example 3.

The WIAM-95 and high-pressure crystallized WIAM-95 were tested using a TA Instruments Q-1000 calorimeter as described in Example 11.

Figure 6:
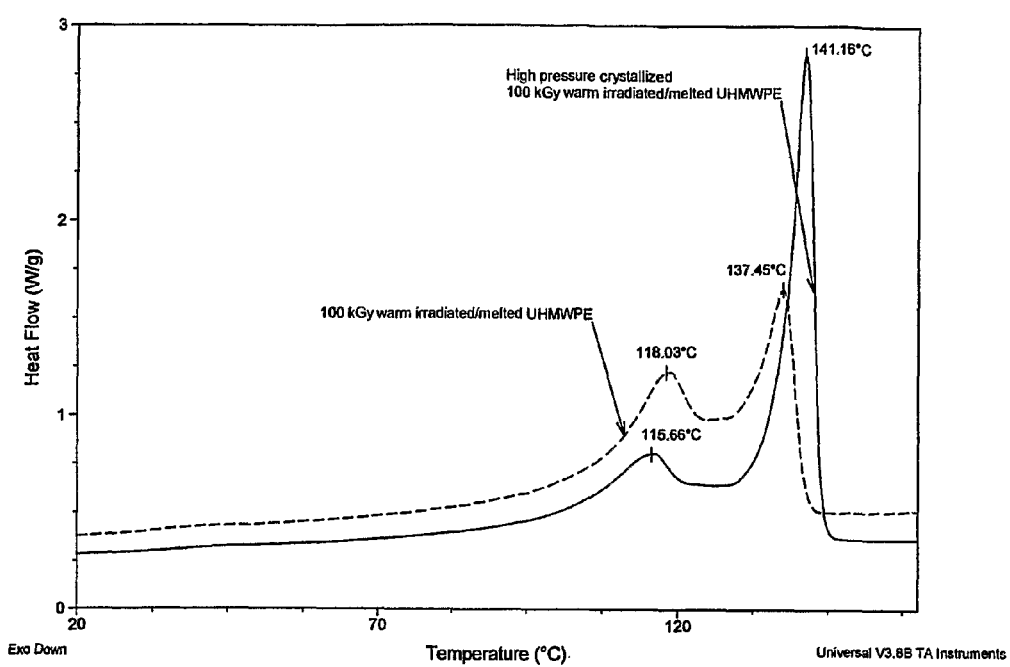
FIG. 6 depicts DSC thermograms of a warm irradiated/melted and a high pressure crystallized warm irradiated/melted polyethylene.

The $1^{st}$ heat crystallinity was 57% for the WIAM-95 and 62% for the high-pressure crystallized WIAM-95. This increase in the crystallinity was mainly attributed to larger crystals with a peak melting point at 141° C. (FIG. 6).

The increase in crystallinity and peak melting temperature with high-pressure crystallization was less profound on the irradiated/melted polyethylene compared to conventional polyethylene, as described in Example 12. The decrease in the number of high molecular weight linear chains and the reduction in mobility caused by the cross-linking decreased the rate of crystal growth. Consequently, during high-pressure crystallization in the hexagonal phase crystals did not grow to the same extent in the cross-linked polyethylene as they did in the conventional polyethylene.

These results showed that even at the relatively low pressure of 320 MPa, it is possible to obtain extended chain crystals for both conventional (see Example 12) and highly cross-linked polyethylene. The experiment showed that high-pressure crystallization of both conventional (see Example 12) and highly cross-linked polyethylene led to increases in crystallinity as well as increases in the population of larger crystals compared to conventional GUR 1050 crystallized at ambient pressure.

Example 14

Morphology of Transparent and Opaque Sections on High Pressure Crystallized Samples Consolidated GUR 1050 (diameter 50 mm, length 90 mm) block was high pressure crystallized by Route I, as described in Example 3.

Figure 7A:
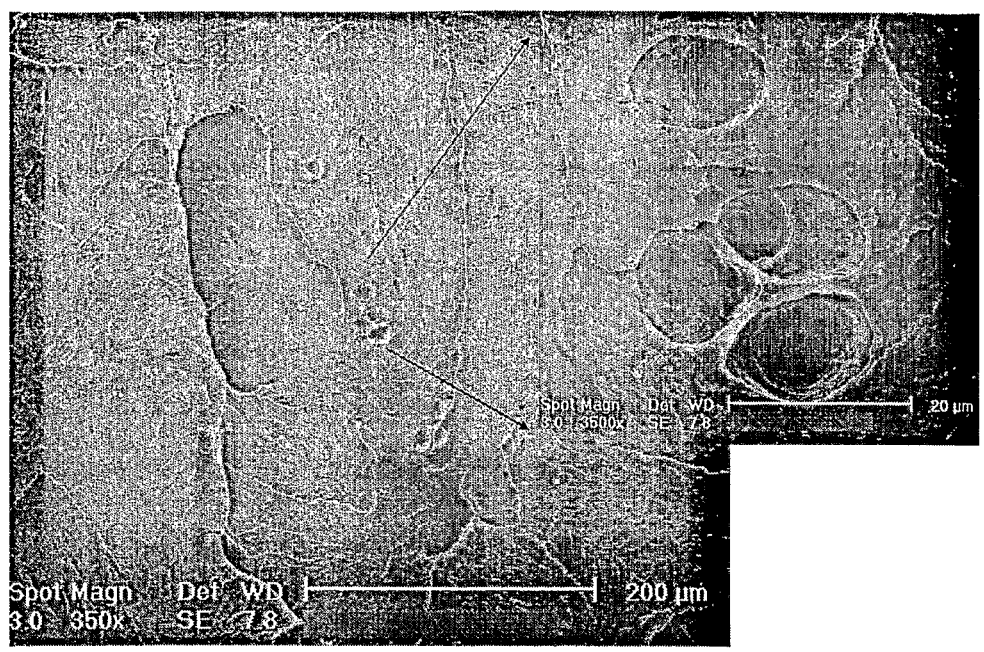
FIGS. 7A, 7B, and 7C depict scanning electron micrographs of (a) opaque (7A), (b) transparent (7B), and (c) transition between opaque and transparent (7C), respectively, sections of high pressure crystallized conventional UHMWPE.
Figure 7B:
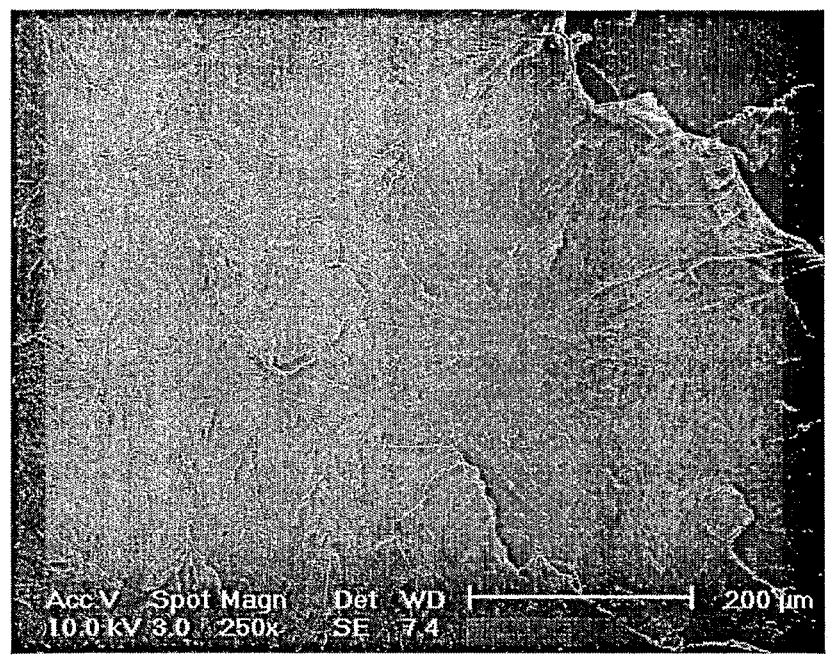
Figure 7C:
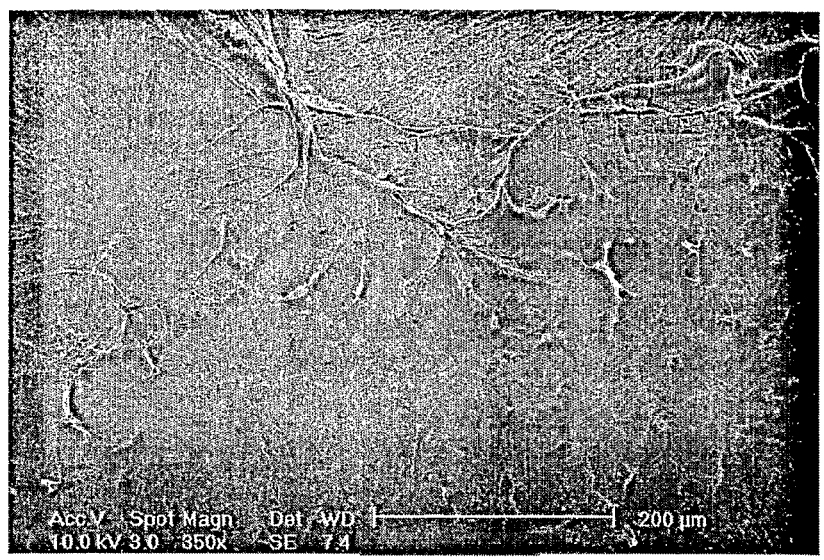

A thin cross-section of the block showing both transparent and opaque regions was freeze fractured and gold coated. This cross-section was analyzed on a scanning electron microscope under high vacuum using a field emission gun. FIGS. 7A, 7B, and 7C show the morphology of the opaque and transparent regions, and the transitional region, respectively.

The transparent side showed more uniform morphology with fewer grain boundaries and no cavities, whereas the opaque side showed a high number of grain boundaries and cavities, as seen in FIGS. 7A and 7B. It is postulated that the cavities are formed by swelling effect of the pressurizing gas (for example, argon gas) used during the high-pressure crystallization. Cavitation is known to scatter light and hence, make the polyethylene appear opaque.

Example 15

Determination of Warm Irradiation Temperature

Warm irradiation of polyethylene was performed in order to maintain a specific crystalline content during irradiation for high cross-linking. Differential scanning calorimetry (DSC) was used to measure the crystallinity of the polyethylene test samples. The sample and the reference were then heated at a heating rate of 10° C./min from −20° C. to 180° C., cooled to −20° C. at −100° C./min and subjected to another heating cycle from −20° C. to 180° C. at 10° C./min. Heat flow as a function of time and temperature was recorded and the cycles are referred to as $1^{st}$ heat, $1^{st}$ cool and $2^{nd}$ heat, respectively.

The heat flow was integrated as a function of temperature for the $1^{st}$ heating cycle of polyethylene from 20° C. to 160° C. The integral at each temperature was subtracted from the integral at 160° C. and the difference was divided by the theoretical enthalpy of fusion of a 100% crystalline UHMWPE (291 J/mol). In this way, a plot was obtained where percent crystallinity was given as a function of temperature. By using this plot, it was possible to determine the temperature where warm irradiation was to be performed with the desired amount of crystalline content.

Example 16

High Pressure Crystallized and Irradiated (I-HPC) UHMWPE

GUR 1050 UHMWPE high pressure-crystallized by Route I, as described in Example 3, was machined into 1 cm thick slices (diameter 5 cm) and electron beam irradiated to a radiation dose of 150 kGy, as described in Example 1, at two different temperatures; room temperature (cold irradiated) (I-HPC1-CI) and at a temperature at which polyethylene was approximately 50% crystalline; in this case, 136° C. (warm irradiated) (I-HPC1-WI). The temperature at which the UHMWPE was 50% crystalline was calculated as described in Example 15.

Example 17

High Pressure Crystallized and Irradiated UHMWPE (I-HPC) with Subsequent High-Pressure Crystallization UHMWPE prepared as described in Example 16 was further subjected to high-pressure crystallization by Route I, as described in Example 3.

Figure 8:
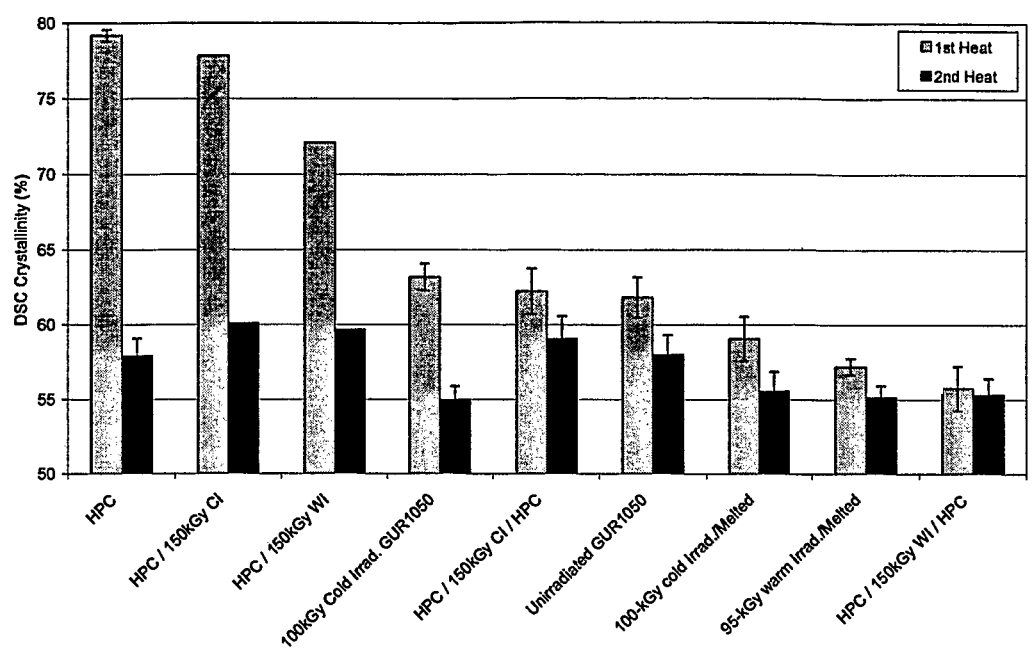
FIG. 8 shows crystallinity of various high pressure crystallized, irradiated, and control UHMWPEs.

The crystallinity values for UHMWPE high pressure-crystallized by Route I (HPC1), high pressure-crystallized and irradiated (HPC1-CI, HPC1-WI) and high pressure crystallized, cold- or warm-irradiated, and subsequently high pressure-crystallized by Route I (HPC1-CI-HPC1 or HPC1-WI-HPC1) samples are shown in FIG. 8. Detailed description of the abbreviated processes is shown below in Table 2. Control materials were unirradiated GUR 1050, 100 kGy cold irradiated GUR 1050, 100-kGy cold irradiated and subsequently melted and 95-kGy warm irradiated and subsequently melted UHMWPE.

The HPC1 had $1^{st}$ heat crystallinity of 79%, which decreased to 78% upon cold-irradiation to a dose of 150 kGy (I-HPC1-CI). The HPC1-CI is expected to contain residual free radicals because of the terminal irradiation step. Therefore, the HPC1-CI was subjected to another step of HPC1. When the HPC1-CI was heated above the melting point prior to pressurization during the second HPC1 step, the residual free radicals would have recombined. However, following the pressurization and crystallization, the crystallinity further decreased to 62% in the final HPC1-CI-HPC1. Nevertheless, the crystallinity of HPC1-CI-HPC1, which has been highly cross-linked and should contain no residual free radicals due to the melting during the high-pressure crystallization process, was still higher than the crystallinity of both the 100-kGy cold-irradiated and melted sample and the 95-kGy warm irradiated and melted sample.

TABLE 2

Description of test samples used in high-pressure crystallization and/or irradiation.

| Sample ID | Description of process |
|---|---|
| HPC1 | High pressure crystallized through Route I |
| HPC1-CI | High pressure crystallized through Route I, then e-beam irradiated to 150 kGy at room temperature (cold irradiated) |
| HPC1-WI | High pressure crystallized through Route I, then e-beam irradiated to 150 kGy at 136° C. (warm irradiated) |
| HPC1-CI-HPC1 | High pressure crystallized through Route I, then e-beam irradiated to 150 kGy at room temperature (cold irradiated) then high pressure crystallized again through Route I |
| HPC1-WI-HPC1 | High pressure crystallized through Route I, then e-beam irradiated to 150 kGy at 136° C. (warm irradiated), then high pressure crystallized through Route I |

Example 18

Cold Irradiation with Subsequent Mechanical Deformation

Two compression molded GUR 1050 rods (diameter 9.1 cm; length 41 cm) were subjected to 100 kGy gamma irradiation in a vacuum package. Both rods were then heated to 130° C. and one was subsequently deformed under uniaxial compression normal to its long-axis to a compression ratio of 2.7 (initial diameter/final diameter). The compression was carried out at 130° C. The compressed rod was held under constant deformation and cooled to room temperature. The load was then released and the dimensions of the rod were recorded (length=58 cm; width=16.6 cm; thickness=40.5 cm). Both the rods were heated to 135° C. to recover the residual deformation and the final dimensions were recorded (diameter=7.5 cm; length=40 cm). Thus, one rod was subjected to mechanical deformation and thermal processing, while the other was only subjected to the identical thermal history without deformation to serve as a control.

Example 19

Free Radical Concentration, Oxidation Levels, and Wear Rate of Irradiated and Mechanically Deformed UHMWPE Two GUR 1050 blocks, prepared as described in Example 18, were analyzed by using electron spin resonance (ESR) (University of Utah, Department of Physics) to quantify the concentration of residual free radicals. Crystallinity was determined by DSC, as described in Example 11. Cubes machined from both rods were subjected to accelerated aging at 80° C. in air for 5 weeks and the oxidation of the samples was determined by using infrared microscopy, as described in Example 8. Finally, the wear behavior of the mechanically annealed rods (n=3) was determined using our bi-directional wear tester, using a method as described in Example 10.

The ESR analysis showed $2\times10^{15}$ spins/gram for the thermal control, while the mechanically annealed sample showed no detectable residual free radicals, identical to 100 kGy irradiated and melted polyethylene. The DSC analysis showed a crystallinity level of 62±0.5% for the 1$^{st}$ heat of the mechanically annealed sample, comparable to that of non-irradiated UHMWPE. The crystallinity level typically decreases to 55-57% following post irradiation melting. Accelerated aging led to oxidation in the thermal control (oxidation index=1.30±0.2), which is significantly more than the mechanically annealed test sample (oxidation index=0.01±0.01) ($p<0.01$). The POD wear rate of the mechanically annealed rod was found to be 0.8±0.0 mg/million-cycles, which is comparable to that of 100-kGy irradiated and melted polyethylene.

Example 20

Fatigue Crack Propagation Testing of Unirradiated, Irradiated and Melted Samples Compression molded UHMWPE GUR 1050 (γ-sterilized in air to 25 kGy-40 kGy), highly cross-linked UHMWPE (γirradiated in vacuum to 100 kGy), and 100-kGy highly irradiated and melted polyethylene were used as control samples. Gamma irradiation was done as described in Example 2.

Fatigue crack propagation testing was performed as described in Example 0.9. The stress intensity factor at crack inception ($\Delta K_i$) along with crystallinity values of control samples are shown in Table 3. Crystallinity was determined by DSC as described in Example 11. Crystallinity of UHMWPE was comparable after low and high dose irradiation. When the high dose irradiated polyethylene was melted, crystallinity decreased significantly ($p<0.001$). The fatigue strength ($\Delta K_i$) decreased by 44% ($p<0.0001$) when the radiation dose was increased from 25-40 kGy to 100 kGy, presumably due to increased number of cross-links. Melting of the 100-kGy irradiated UHMWPE further decreased the fatigue strength by 19% ($p<0.001$)), presumably due to the decrease in crystallinity.

TABLE 3

Stress intensity factor range at crack inception of control and irradiated and melted polyethylenes.

| | Material | | |
|---|---|---|---|
| | 25-40-kGy irradiated (no melting) | 100-kGy irradiated (no melting) | 100-kGy irradiated and melted |
| Samples tested | 3 | 4 | 5 |
| $\Delta K_i$ (MPa·m$^{1/2}$) | 1.29 ± 0.04 | 0.72 ± 0.04 | 0.58 ± 0.03 |
| Crystallinity (%) | 62 ± 1.4 | 64 ± 0.9 | 57 ± 0.6 |

Example 21

Fatigue Crack Propagation Testing of High Pressure Crystallized UHMWPE

Fatigue crack propagation testing was performed, as described in Example 9, on compression-molded unirradiated GUR 1050 UHMWPE that was high pressure-crystallized by Route I as described in Example 3.

The stress intensity factor at crack inception ($\Delta K_i$) was 1.37±0.06 (n=3) and 1.49 MPa√m (n=2) for GUR 1050 UHMWPE and high pressure-crystallized GUR 1050 UHMWPE, respectively. We machined the compact tension specimens with crack tip at the core of the high pressure-crystallized cylinder, which, as described in Example 12, was found to be the highly crystalline region.

Example 22

Pin-on-Disk (POD) Wear Test of UHMWPE Blended with 0.1% and 0.3% Vitamin E Prior to Consolidation The effects of Vitamin E blended with UHMWPE resin powder prior to irradiation on the wear resistance of irradiated GUR 1050 UHMWPE were determined. Vitamin E (α-tocopherol) was mixed with GUR 1050 UHMWPE powder, in two concentrations, 0.1 wt % and 0.3 wt %, and consolidated. The consolidation of UHMWPE into blocks was achieved by compression molding. One additional consolidation was carried out without α-tocopherol additive and used as a control. The three consolidated blocks were machined into halves and one half of each was packaged in vacuum and gamma irradiated to 100 kGy, as described in Example 2.

Cylindrical pins, 9 mm in diameter and 13 mm in length, were cut out of the irradiated blocks. The pins were first subjected to accelerated aging at 80° C. for 5 weeks in air and subsequently tested on a bi-directional pin-on-disk (POD), as described in Example 10.

The typical wear rate of UHMWPE with no radiation history and no α-tocopherol treatment is around 8.0 milligram per million cycles and for 100-kGy irradiated and melted UHMWPE is 1 mg/MC. The wear rates for the 100-kGy irradiated α-tocopherol blended pins were 2.10±0.17 and 5.01±0.76 milligram per million cycles for the 0.1% and 0.3 wt% α-tocopherol concentration, respectively. The reduction in wear resistance is less with higher α-tocopherol content.

These results suggest that the cross-link density of UHMWPE, achieved by a high irradiation dose, decreases with increasing concentration of α-tocopherol content in the mixture. We believe that this is because of the antioxidant activity of α-tocopherol acting on the free radicals on UHMWPE chains that would in its absence form cross-links with each other.

Example 23

Oxidative Stabilization of Irradiated UHMWPE by α-Tocopherol Doping

Consolidated GUR 1050 UHMWPE bar stock was gamma irradiated to 65 and 100 kGy as described in Example 2. 2 cm cubes were machined of this bar stock. The samples were doped with Vitamin E (α-Tocopherol (α-T)) for 16 hours at room temperature in air. Following doping, the samples were further gamma sterilized at a dose of 27 kGy. These two groups are referred to as α-T-92 and α-T-127 with a total radiation dose of 92 kGy and 127 kGy, respectively. The control materials was 100-kGy gamma irradiated GUR 1050.

All samples were accelerated aged at 80° C. in air for five weeks. After this, the cubes were cut in halves and oxidation levels were assessed as described in Example 8.

Figure 9:
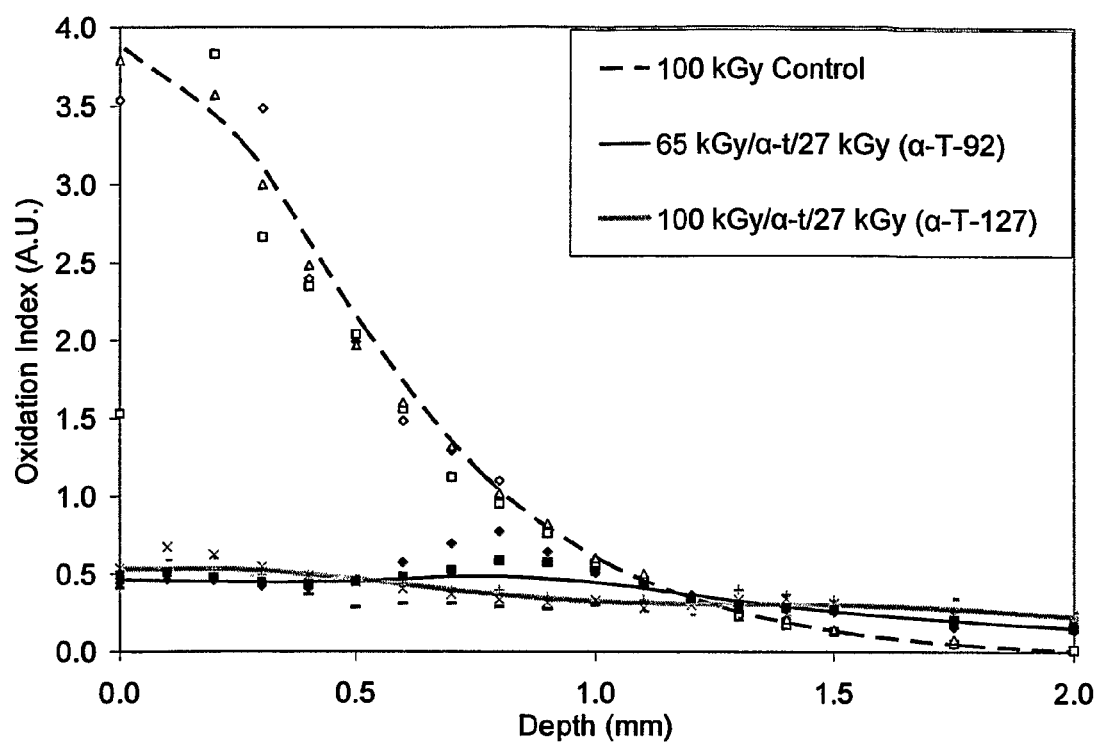
FIG. 9 shows Oxidation Index as a function of distance away from the surface of accelerated aged 100-kGy irradiated, α-T-92 and α-T-127 samples. The curves represent splined averages of three test samples.

The effects of aging on the oxidation of un-doped and α-T doped samples are shown in FIG. 9. The curves represent splined averages of three samples. The 100-kGy irradiated control samples showed significantly higher oxidation levels when compared to α-T-92 and α-T-127 samples; maximum oxidation indices were 3.74±0.16, 0.48±0.25 ($p<0.001$), and 0.44±0.06 ($p<0.001$), respectively. It appeared that α-tocopherol protected irradiated polyethylene against oxidation during accelerated aging at 80° C. in air.

Example 24

Oxidative Stabilization of High Pressure Crystallized and Irradiated UHMWPE by Vitamin E Doping Compression-molded GUR 1050 (diameter 0.2") block was high pressure-crystallized, as described in Example 3. The block was machined into thin sections of approximately 8.5 mm thickness. These thin sections were irradiated to a dose of 100-kGy by electron beam, as described in Example 1.

One of the resulting circular sections was cut into four quarters. One was doped in α-tocopherol (vitamin E) for 16 hours at room temperature in air, another was doped in α-tocopherol for 16 hours at 100° C. in air. The two corresponding thermal controls were kept at room temperature and at 100° C., respectively, for 16 hours in air without doping. All four samples were cut in halves and one half was accelerated aged in a convection oven for 5 weeks at 80° C., in air. The other half was unaged.

Figure 10:
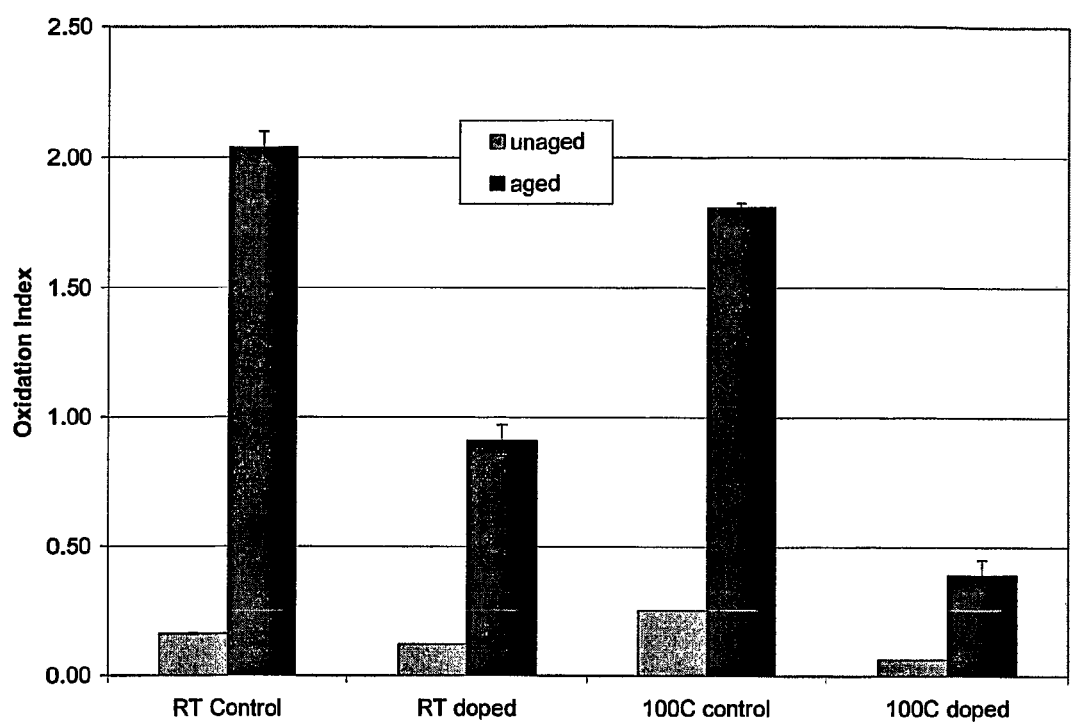
FIG. 10 shows average maximum oxidation levels for unaged and aged high pressure crystallized, 100-kGy e-beam irradiated, and α-tocopherol doped UHMWPE. Doping was done in air for 16 hours at room temperature and at 100° C. Corresponding thermal controls also were kept at room temperature and at 100° C., respectively, for 16 hours in air without doping.
Figure 11:
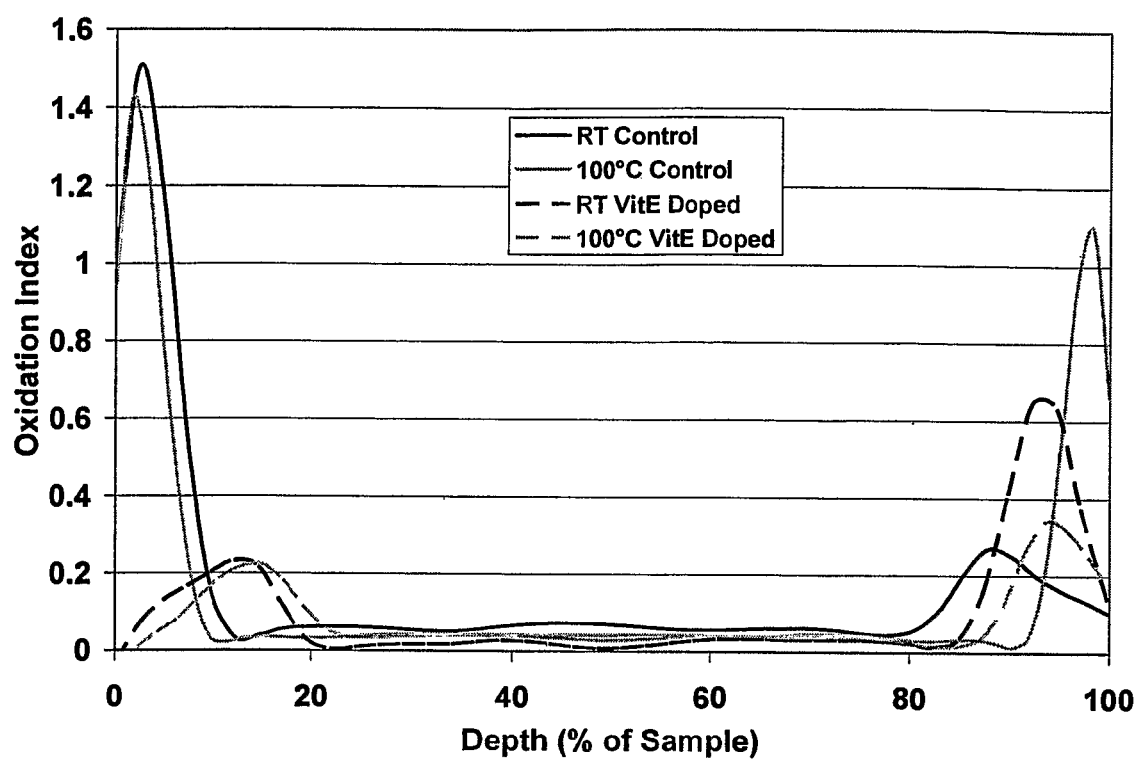
FIG. 11 depicts splined averages (n=3) of the oxidation profiles of high pressure crystallized, 100-kGy irradiated, α-tocopherol doped, and accelerated aged UHMWPEs.

The oxidation profiles for all samples were assessed as described in Example 8. There was significant subsurface oxidation in the aged thermal controls while the α-tocopherol doped samples showed significantly lower oxidation levels than controls ($p<0.01$, and $p<0.9001$ for room temperature (RT) and 100° C. doped samples, see FIGS. 10 and 11).

Example 25

Oxidative Stabilization of High Pressure Crystallized and Irradiated UHMWPE by Mechanical Deformation Compression-molded GUR 1050 (diameter 2") block is high pressure crystallized, as described in Example 3. The block is machined into thin sections of approximately 8.5 mm thickness. These thin sections are irradiated to a dose of 100-kGy by electron beam as described in Example 1.

One thin section is heated to 137° C. and mechanically deformed under uniaxial compression at this temperature to a compression ratio of about 2.5 (initial/final height). The compressed rod is held under constant deformation and cooled back down to room temperature under constant deformation. The load is then released and the dimensions of the rod were recorded. This section is subsequently heated to 144° C. to recover the residual deformation. The thin section is cut in halves and one half was accelerated aged at 80° C. in air for 5 weeks.

A thin piece (cross-section approximately 3 mm by 3 mm) is machined out of the remaining piece for electron spin resonance (ESR) analysis (at Department of Physics, University of Memphis, Tenn.).

The high pressure crystallized and 100-kGy irradiated UHMWPE is stabilized by mechanical deformation and ESR values for this sample are not expected to be significantly different than the background number of spins.

Aggressively accelerated aged UHMWPE, which was high pressure crystallized, 100-kGy irradiated UHMWPE, and stabilized by mechanical deformation can show significantly less oxidation than that of accelerated aged, high pressure crystallized, and 100-kGy irradiated control.

Example 26

Pin-on-Disk (POD) Wear Testing of UHMWPE Doped with Vitamin E After Irradiation

Consolidated GUR 1050 UHMWPE bar stock was gamma irradiated to 65 and 100 kGy. Cylindrical pins (9 mm diameter, 13 mm length) for POD wear testing were machined from these irradiated polyethylenes. The samples were doped with vitamin E (α-T) for 16 hours at room temperature in air. Following doping, the samples were further gamma sterilized at a dose of 27 kGy. These two groups are referred to as α-T-92 and α-T-127 with a total radiation dose of 92 and 127 kGy, respectively.

Control samples were 1) 100-kGy gamma irradiated GUR 1050 followed by melting at 150° C., 2) 105-kGy gamma irradiated GUR 1050 followed by annealing at 120° C. and 3) 25-kGy gamma sterilized GUR 1050 in nitrogen. Gamma irradiation was done as described in Example 2.

Half of the cylindrical samples were subjected to accelerated aging at 80° C. in air for five weeks. Both unaged and aged samples were then subjected to POD wear testing, as described in Example 10.

Figure 12:
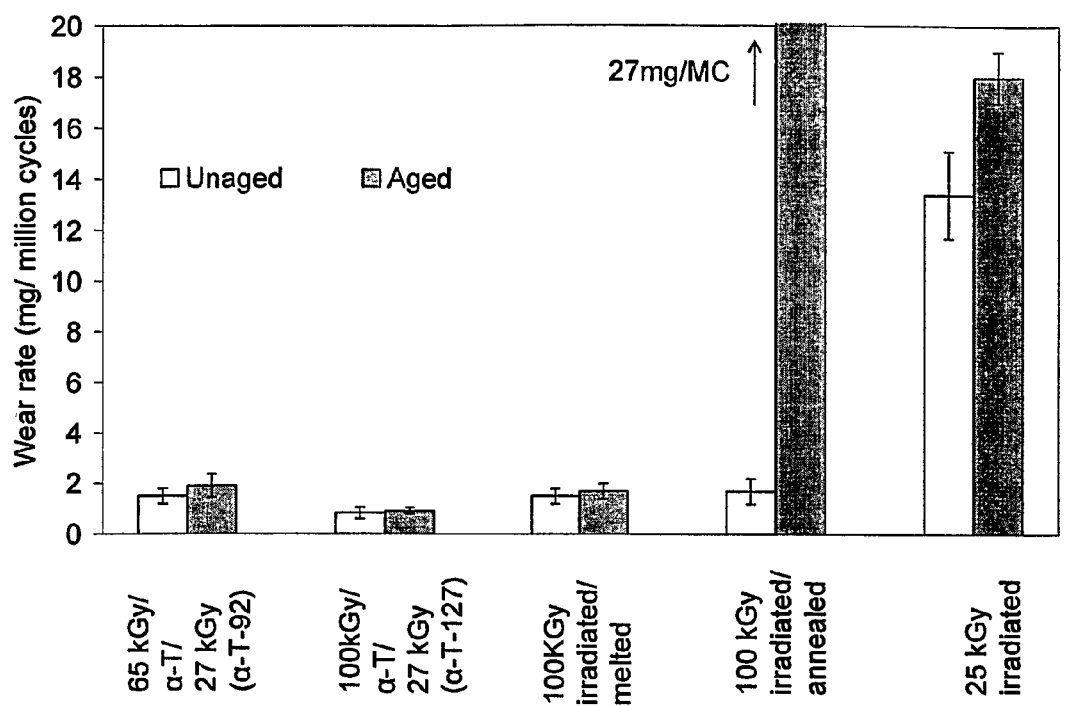
FIG. 12 indicates Pin-on-Disk (POD) wear rates of unaged and aged Vitamin E doped and undoped samples.

The wear rates of doped and undoped cross-linked and conventional polyethylenes before and after accelerated aging are shown in FIG. 12. The wear rate measured for the two groups of α-T-doped, highly cross-linked polyethylene groups are reported along with the wear rate of 25 kGy irradiated conventional polyethylene (γ-sterilized in nitrogen), 100 kGy irradiated/melted and 105 kGy irradiated/annealed samples before or after aging. The wear rate of the 100 kGy irradiated/annealed and conventional polyethylenes increased after aging. The wear rates of α-T-92 and α-T-127 were equivalent to that of irradiated and melted UHMWPE. Aging did not change the wear behavior of either α-T-92 or α-T-127 (p>0.05). This result indicates that α-T was able to protect UHMWPE against oxidation and since α-T doped samples did not oxidize, their wear rate was similar to unaged specimens.

Example 27

The Effect of Extraction by Ethanol on the Oxidation and Wear Behavior of Irradiated UHMWPE Consolidated GUR 1050 UHMWPE bar stock was gamma irradiated to 65 kGy and 100 kGy. Cylindrical pins (9 mm diameter, 13 mm length) for POD wear testing and cubes (2 cm) for accelerated aging and oxidation testing were machined from these irradiated polyethylenes. The samples were doped with vitamin E (α-T) for 16 hours at room temperature in air. Following doping, the samples were further gamma sterilized at a dose of 27 kGy. These two groups are referred to as α-T-92 and α-T-127 with a total radiation dose of 92 kGy and 127 kGy, respectively.

Half of the cubes and pins were placed in boiling ethanol overnight to remove α-tocopherol from the UHMWPE. Then, they were placed in a convection oven for 5 weeks in air at 80° C. for accelerated aging. The other half were just accelerated aged for 5 weeks at 80° C. in air.

Figure 13:
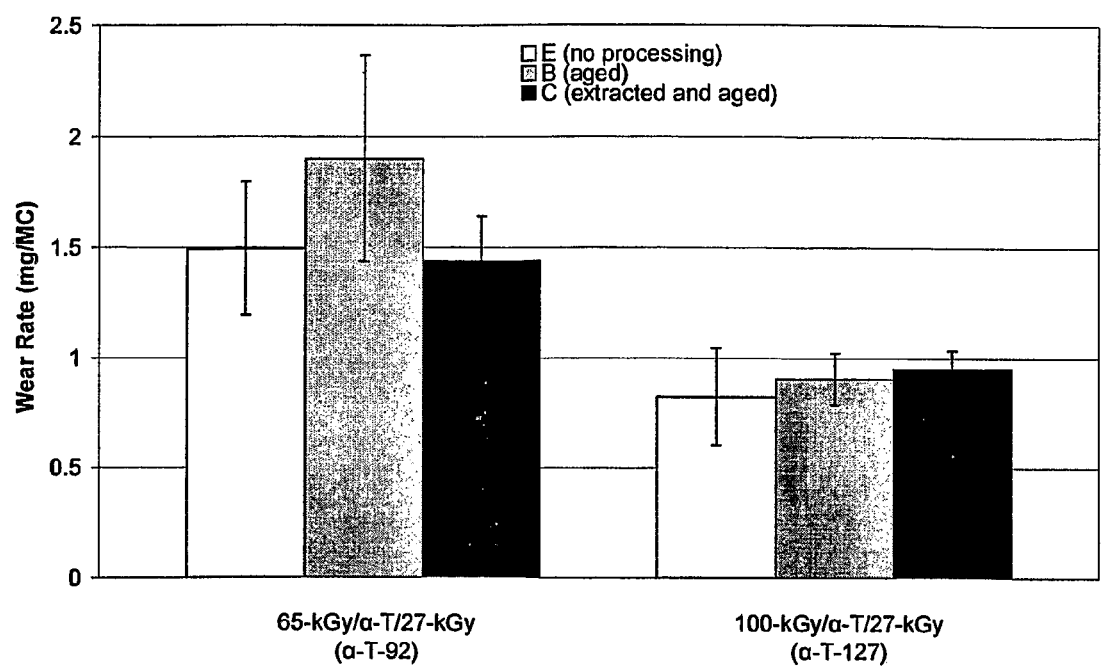
FIG. 13 shows the wear rates of unaged, just accelerated aged and ethanol extracted and accelerated aged α-T-92 and α-T-127.

Oxidation profiles for the cubes were assessed as described in Example 8 and POD wear testing was done on the pins as described in Example 10. Average maximum oxidation levels observed are as shown in Table 4. There was a significant (p<0.05) but small difference between aged and extracted and aged samples for 100-kGy irradiated control and α-T-127 (FIG. 13 and Table 4). Therefore, there was no appreciable difference in oxidation behavior between just aged and extracted and aged samples. Extraction in boiling ethanol did not remove the α-tocopherol from UHMWPE and α-tocopherol was able to protect UHMWPE against oxidation.

Also, the oxidation levels of α-T-92 and α-T-127 were significantly lower than that for the 100-kGy irradiated control for extracted and aged samples. This showed that α-tocopherol was able to protect against oxidation of irradiated UHMWPE after it was subjected to boiling ethanol treatment.

TABLE 4

Maximum oxidation values for accelerated aged and ethanol extracted/aged α-tocopherol doped irradiated UHMWPE and 100-kGy irradiated control.

| Material | Aged Oxidation values | Ethanol Extracted and Aged |
|---|---|---|
| 100-kGy control | 3.74 ± 0.16 | 4.55 ± 0.33 |
| α-T-92 | 0.48 ± 0.25 | 0.62 ± 0.14 |
| α-T-127 | 0.44 ± 0.06 | 0.60 ± 0.08 |

Similarly, the wear rates of aged α-T-92 and α-T-127 were not affected significantly by the extraction process (see FIG. 13).

Example 28

The Effect of Cleaning by Washing on the Oxidation and Wear Behavior of Irradiated UHMWPE Slab compression-molded GUR 1050 UHMWPE blocks (Perplas Ltd., Lancashire, UK) (3" diameter) were gamma-irradiated in vacuum to a dose of III-kGy (Steris Isomedix, Northborough, Mass.). These blocks were then machined into half-cubes (2 cm×2 cm×1 cm).

The half-cubes were immersed in α-tocopherol (α-D, L-tocopherol, Fischer Scientific, Houston, Tex.) at room temperature and 100° C. in air for 1 and 16 hours, respectively (n=3 each). Three thermal controls (room temperature, 100° C. for 1 and 16 hours) were subjected to the same doping temperature without α-tocopherol.

Cleaning was performed by a portable Kenmore dishwasher (Sears Inc, Hoffman Estates, Ill.) on normal cycle with rinse and heat drying. During cleaning, all half-cube test samples were placed in a cylindrical nonelastic polyethylene mesh of 2" diameter and closed at the ends. This ensured that the samples did not move around, but the cleaning medium could get through. Electrasol™ (Reckitt Benckiser Inc., Berkshire, UK) was used as cleaning agent.

Oxidation profiles for the cubes were assessed as described in Example 8 and the average of maximum oxidation levels are reported in Table 5.

TABLE 5

Maximum oxidation values for cleaned and accelerated aged control and α-T doped 111-kGy irradiated UHMWPE. RT denotes that doping was done at room temperature.

| Conditions | Average Maximum Oxidation Index |
|---|---|
| 111-kGy RT control | 3.68 ± 0.15 |
| RT 1 hr | 038 ± 0.05 |
| RT 16 hrs | 0.40 ± 0.03 |
| 111-kGy 100° C. 1 hr control | 0.97 ± 0.04 |
| 100° C. 1 hr | 0.098 ± 0.003 |
| 111-kGy 100° C. 16 hrs control | 0.70 ± 0.18 |
| 100° C. 16 hr | 0.080 ± 0.003 |

These oxidation values for cleaned and aged α-tocopherol-doped 111-kGy irradiated UHMWPE are similar to that of the samples in Example 27 that had been irradiated to 65 and 100-kGy, α-tocopherol doped, and then gamma sterilized (27-kGy) and aged without cleaning; A. U. 0.48±0.25 and 0.44±0.06, respectively (Table 4). The cleaning procedure could not to remove the α-tocopherol already diffused through the surface of the UHMWPE.

Figure 14:
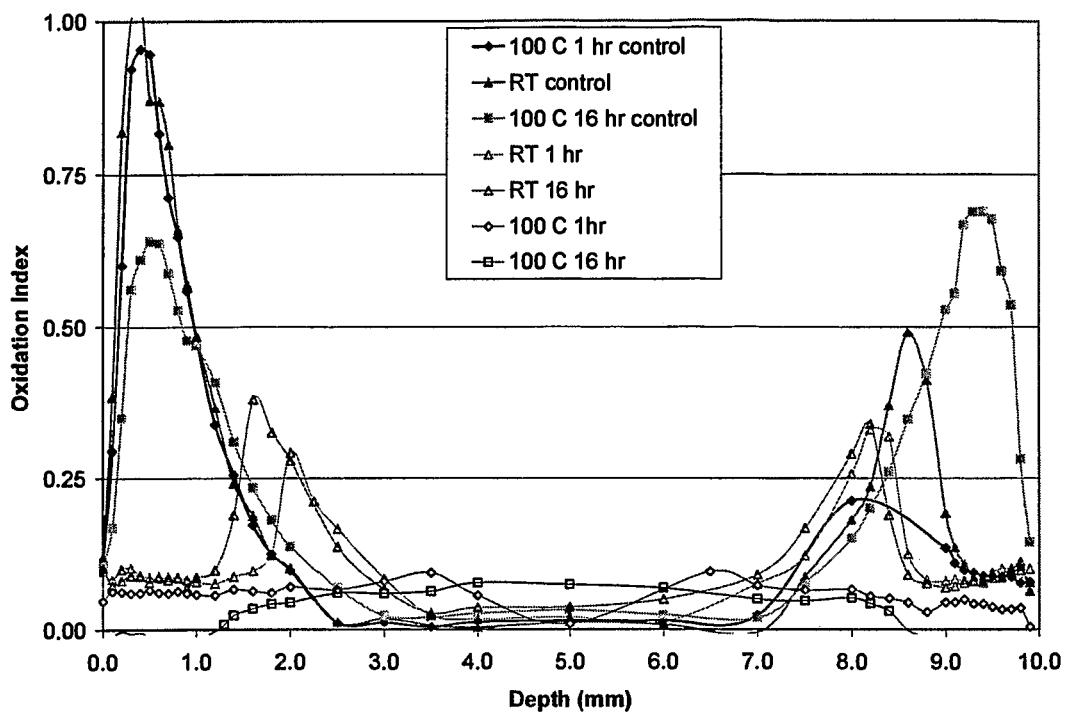
FIG. 14 shows the oxidation profiles of accelerated aged 111-kGy irradiated control and 111-kGy irradiated and α-tocopherol-doped and cleaned UHMWPE.

Thermal control for 111-kGy irradiated, cleaned and aged samples for UHMWPE diffused with α-tocopherol at 100° C. for 1 hour showed higher levels of oxidation than that of the α-tocopherol-diffused test samples (p<0.0005). Similarly, thermal control for 111-kGy irradiated, cleaned and aged samples for UHMWPE diffused with α-tocopherol at 100° C. for 16 hours showed higher levels of oxidation than that of the α-tocopherol-diffused test samples (p<0.0005). The oxidation levels of the controls and test samples did not show significant difference between a soak time of 1 hour and 16 hours. The oxidation levels for doped samples at 100° C. were significantly less than those doped at room temperature (p<0.01 and p<0.005 for 1 and 16 hours, respectively). The oxidation profile of a representative sample of each preparation is shown in FIG. 14.

Example 29

Calculating Crosslink Density of UHMWPE by Dynamic Mechanical Analyzer

Crosslink density measurements were performed with a dynamic mechanical analyzer (DMA 7e, Perkin Elmer, Wellesley, Mass.). Rectangular pieces of UHMWPE were set in dental cement and sliced into thin sections (2 mm thick). Small sections were cut out by razor blade from these thin sections to be analyzed (approximately 2 mm by 2 mm). These small pieces were placed under the quartz probe of the DMA and the initial height of the sample was recorded. Then, the probe was immersed in xylene, which was subsequently heated to 130° C. and held for 45 minutes. The UHMWPE samples swelled in boiling xylene until equilibrium was reached (the weight change was less than 0.1%). The final weight was recorded.

The crosslink density was calculated in the following manner:

The ratio of the final height to the initial height was cubed to obtain the swell ratio, q, assuming homogeneous expansion in all three directions. Then the crosslink density, $v_c$, was calculated from:

$$v_c = -\frac{\ln(1-q^{-1}) + q^{-1} + \chi q^{-2}}{\overline{V}_1 q^{-1/3}}$$

where $\overline{V}_1$ is the partial volume of xylene (136 cm$^3$/mol) and $\chi$ is the Flory-Huggins interaction parameter defined as $\chi=0.33+0.55/q$. Average molecular weight between crosslinks was also calculated.

$$\overline{M}_c = \frac{\rho}{v_c}$$

A more densely cross-linked structure will have higher cross-linking density and lower molecular weight between crosslinks than a more loosely cross-linked structure.

Example 30

Cross-Linking Density of Cold and Warm Irradiated High Pressure Crystallized Polyethylene The crosslink density and molecular weight between crosslinks was calculated as described in Example 29 for I-HPC CI and I-HPC WI to investigate the differences in cross-linking between these two UHMWPEs due to the increased amorphous phase in the warm irradiation process (see Table 6).

TABLE 6

Crosslink density and molecular weight between crosslinks for warm and cold irradiated previously high pressure crystallized UHMWPEs.

| Sample | Crosslink Density (mol/m$^3$) | Molecular Weight between Crosslinks (g/mol) |
|---|---|---|
| I-HPC CI opaque | 173 ± 8 (n = 3) | 4990 ± 230 (n = 3) |
| I-HPC WI | 155 ± 31 (n = 3) | 5711 ± 1042 (n = 3) |

TABLE 6-continued

Crosslink density and molecular weight between crosslinks for warm and cold irradiated previously high pressure crystallized UHMWPEs.

| Sample | Crosslink Density (mol/m$^3$) | Molecular Weight between Crosslinks (g/mol) |
|---|---|---|
| I-HPC CI opaque transparent | 148 ± 36 (n = 3) | 6075 ± 1670 (n = 3) |
| I-HPC WI transparent | 155 ± 13 (n = 2) | 5580 ± 487 (n = 2) |

Although the warm and cold irradiated I-HPC polyethylenes did not show significant differences, these 150-kGy irradiated UHMWPEs showed lower cross-linking ratios than 150-kGy cold-irradiated and melted UHMWPE (209 mol/m$^3$; Muratoglu et al., 1999). This is because during irradiation, there was less amorphous phase available in the high pressure crystallized UHMWPE, as discussed in Example 12 (for example, a 78% crystalline UHMWPE will only have 21% amorphous content available for cross-linking as opposed to about 36% for a 100-kGy cold-irradiated UHMWPE). The present approach can provide highly crystalline UHMWPE with a markedly higher degree of cross-linking than previous approaches in the prior art.

Example 31

Vitamin E

Vitamin E (Acros™ 99% D-α-Tocopherol, Fisher Brand), was used in the experiments described herein, unless otherwise specified. The vitamin E used is very light yellow in color and is a viscous fluid at room temperature. Its melting point is 2-3° C.

Example 32

Plasticization of UHMWPE

Compression-molded GUR 1050 UHMWPE was machined into thin sections (diameter approximately 90 mm, thickness 3.2 mm). One thin section was placed in α-tocopherol at 132° C. for 5 hours under partial vacuum/nitrogen. Then, it was taken out of the α-tocopherol, the surface was wiped clean with a cotton gauze. The thin section was then placed at 132° C. for 48 hours under partial vacuum/nitrogen. α-tocopherol profile in the sample was measured as described in Example 7. The profile was found to be uniform with an average α-tocopherol index of 0.92±0.10 taken from 16 points along the sample thickness. A thin section of consolidated GUR 1050 of the same dimensions was used as control without doping with α-tocopherol.

Dogbone specimens (n=5) were stamped out of this thin section and testing was done according to ASTM D-638 Standard test method for tensile properties of plastics at a crosshead speed of 10 mm/min. The engineering strain at break was 521±16% for control UHMWPE and 1107±36% for α-tocopherol-doped and annealed UHMWPE. This result showed that engineering strain at break was significantly increased when UHMWPE was doped uniformly with α-tocopherol. This increase in engineering strain at break may be an indication of the plasticization effect of α-tocopherol on UHMWPE.

Example 33

Plasticization of Irradiated UHMWPE

Figure 15:
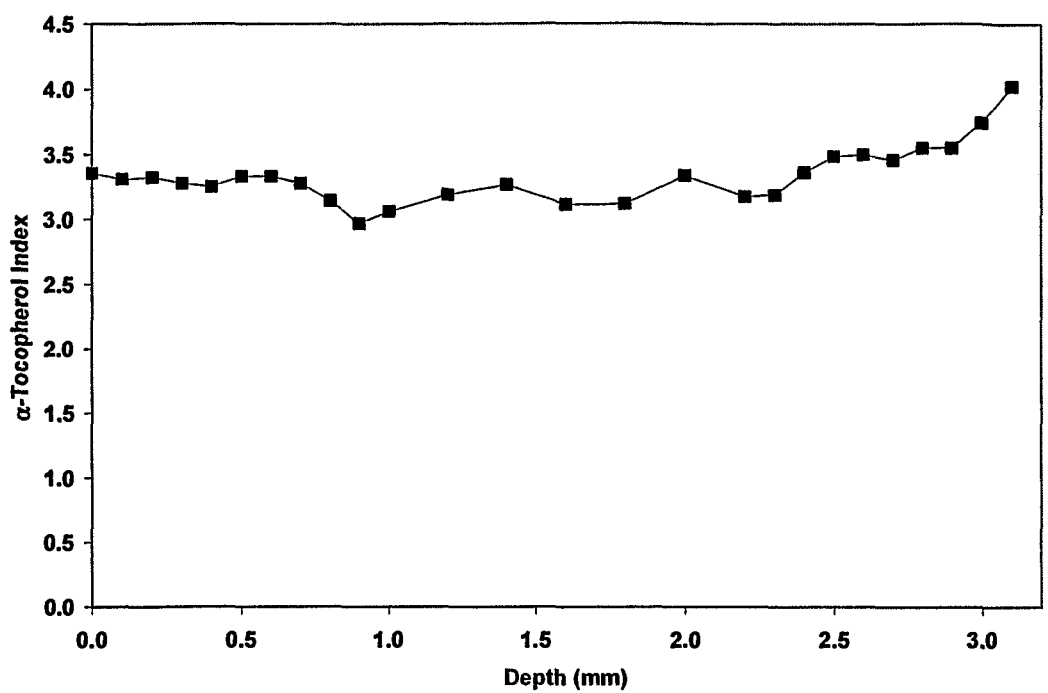
FIG. 15 shows α-tocopherol profile of 100-kGy irradiated UHMWPE, which was doped for 72 hours and annealed for 100 hours at 136° C.

A compression-molded GUR 1050 UHMWPE block (3" diameter, 3' length) was irradiated to 100 kGy. Thin sections (thickness 3.2 mm) were machined from the block. One thin section of the block was placed in α-tocopherol at 136° C. for 72 hours under partial vacuum/nitrogen. The thin section of the block was taken out of α-tocopherol, the surface was wiped clean with a cotton gauze. The thin section was then placed at 136° C. for 100 hours under partial vacuum/nitrogen. α-tocopherol profile was measured as described in Example 7. The profile was found to be uniform (see FIG. 15) with an average α-tocopherol index of 3.33±0.22 taken from 16 points along the sample thickness. A thin section of 100 kGy-irradiated GUR 1050 UHMWPE was used as control without doping with α-tocopherol.

Dogbone specimens (n≧3) were stamped out of these thin sections and testing was done according to ASTM D-638 Standard test method for tensile properties of plastics at a crosshead speed of 10 mm/min. The elongation-to-break (EAB), ultimate tensile stress (UTS) and yield strength (YS) of 100 kGy-irradiated and 100 kGy-irradiated and α-tocopherol doped UHMWPE are shown in Table 7.

TABLE 7

Mechanical properties of 100 kGy irradiated and 100 kGy irradiated and α-tocopherol doped UHMWPE.

| Material | UTS (MPa) | YS (MPa) | EAB (%) | Average Vitamin E Index |
|---|---|---|---|---|
| 100-kGy | 33 ± 1 | 21 ± 2 | 214 ± 7 | — |
| α-Tocopherol doped 100-kGy | 40 ± 3 | 21 ± 2 | 241 ± 6 | 3.33 ± 0.22 |

The engineering strain at break was 741±46% for 100 kGy irradiated UHMWPE and 1049±135% for α-tocopherol-doped, irradiated UHMWPE. These results showed that UTS, EAB and engineering strain at break were significantly increased when irradiated UHMWPE was doped with α-tocopherol. These increases are indications of the plasticization effect of α-tocopherol on irradiated UHMWPE.

Example 34

High Pressure Crystallization of UHMWPE Blended with Vitamin E Prior to Consolidation The effects of vitamin E on the mechanical properties of high pressure crystallized UHMWPE were determined. Vitamin E (α-tocopherol) was mixed with GUR 1050 UHMWPE powder at a concentration of 0.1 wt % and consolidated. The consolidation of UHMWPE into blocks was achieved by compression molding.

A block of approximately 2" in diameter and 2" in height was high pressure crystallized through Route I, as described in Example 3.

Thin sections (thickness=3.2 mm) were machined from high pressure crystallized, vitamin E-blended UHMWPE.

First heat crystallinity of blended UHMWPE and high pressure crystallized, blended UHMWPE was determined as described in Example 11.

Dogbone specimens (n≧2) were stamped out of these thin sections and testing was done according to ASTM D-638 Standard test method for tensile properties of plastics at a crosshead speed of 10 mm/min. The elongation-to-break (EAB), ultimate tensile stress (UTS) and yield strength (YS) of blended UHMWPE and high pressure crystallized, blended UHMWPE are shown in Table 8.

TABLE 8

The elongation-to-break, ultimate tensile stress, and yield strength of blended UHMWPE.

| | Crystallinity (%) | UTS (MPa) | YS (MPa) | EAB (%) |
|---|---|---|---|---|
| 0.1 wt % blended UHMWPE | 64 ± 0.5 | 55 ± 3 | 23 ± 1 | 423 ± 8 |
| HPC 0.1 wt % blended UHMWPE | 77 ± 1 | 63 ± 4 | 26 ± 3 | 576 |
| HPC UHMWPE | 77 ± 2 | 56 ± 6 | 24 ± 2 | 361 ± 31 |

0.1 wt % blended UHMWPE showed an increase in UTS, YS and EAB compared to high pressure crystallized virgin UHMWPE and 0.1 wt % blended UHMWPE prior to high pressure crystallization. The deformed sections of the dogbone samples of the high pressure crystallized 0.1 wt % blended UHMWPE showed extensive whitening, which is an indication of cavitation in these samples.

Example 35

Irradiation of UHMWPE Blended with Vitamin E Prior to Consolidation

The effects of vitamin E on the mechanical and wear properties of irradiated UHMWPE were determined. Vitamin E (α-tocopherol) was mixed with GUR 1050 UHMWPE powder at a concentration of 0.1 wt % and consolidated. The consolidation of UHMWPE into blocks was achieved by compression molding.

A 5 cm×10 cm×10 cm blended block was irradiated by gamma irradiation to a dose of 150 kGy. Thin sections (thickness=3.2 mm) and cylindrical pins (diameter 9 mm, height 13 mm) were machined from the irradiated block.

The crystallinity of blended and irradiated UHMWPE was determined as described in Example 11.

The cross-linking density of blended and irradiated UHMWPE was determined as described in Example 29.

Dogbone specimens (n≧2) were stamped out of these thin sections and testing was done according to ASTM D-638 Standard test method for tensile properties of plastics at a crosshead speed of 10 mm/min.

The pin-on-disc (POD) wear rate of blended and irradiated UHMWPE was quantified using POD testing as described in Example 10.

The crystallinity of 0.1 wt % α-tocopherol blended and 150 kGy irradiated UHMWPE was 65±4%. The cross-linking density, as measured by dynamic mechanical analyzer, was 166±2 mol/m$^3$. The ultimate tensile strength was 40±3 MPa, the yield strength was 20±1 MPa, and the elongation-at-break was 244±22%. The POD wear rate was 1.9±0.3 mg/million-cycles. In comparison, a 150 kGy electron beam irradiated UHMWPE showed a ultimate tensile strength (UTS) of 29±1 MPa, a yield strength (YS) of 22±1 MPa and an elongation-at-break (EAB) of 219±16%.

Example 36

High Pressure Crystallization of Irradiated UHMWPE Blended with Vitamin E Prior to Consolidation The effects of vitamin E on the mechanical properties of high pressure crystallized, irradiated UHMWPE. Vitamin E (α-tocopherol) was mixed with GUR 1050 UHMWPE powder at a concentration of 0.1 wt % and consolidated were determined. The consolidation of UHMWPE into blocks was achieved by compression molding.

A 5 cm×10 cm×10 cm blended block was irradiated by gamma irradiation to a dose of 150 kGy.

A block of approximately 2" in diameter and 2" in height was machined from the above-described block and placed in a pressure chamber in water. The samples were heated to 185° C. for 5 hours, and then isothermally pressurized to 45,000 psi. The pressure and temperature was held constant for 5 hours. At the completion of the pressurizing cycle, the samples were cooled to room temperature under pressure. Subsequently, the pressure was released.

The crystallinity of blended and irradiated UHMWPE was determined as described in Example 11.

Thin sections (thickness=3.2 mm) were machined from this high pressure crystallized, irradiated block. Dogbone specimens (n≧9) were stamped out of these thin sections and testing was done according to ASTM D-638 Standard test method for tensile properties of plastics at a crosshead speed of 10 mm/min.

The crystallinity of high pressure crystallized, 150-kGy irradiated, 0.1 wt % α-tocopherol blended UHMWPE was 70±1%. The ultimate tensile strength of high pressure crystallized, 150-kGy irradiated, 0.1 wt % α-tocopherol blended UHMWPE was 37±2 MPa, the yield strength was 23±1 mPa and the elongation-at-break was 234±0%.

Example 37

Cross-Link Density of α-Tocopherol Blended and Irradiated UHMWPE

The effects of vitamin E on the cross-linking efficiency of irradiated UHMWPE, were determined. Vitamin E (α-tocopherol) was mixed with GUR 1050 UHMWPE powder at a concentration of 0.1, 0.3 and 1.0 wt % and consolidated. The consolidation of UHMWPE into blocks (5×10×10 cm) was achieved by compression molding. Virgin UHMWPE was used as control.

One block of each was irradiated by gamma irradiation to 65, 100, 150 and 200 kGy.

Thin sections (thickness=3.2 mm) were machined from the α-tocopherol blended and irradiated UHMWPEs.

Cross-link density of α-tocopherol-blended, irradiated UHMWPE was determined as described in Example 29.

TABLE 9

Cross-link density (mol/m$^3$) of α-tocopherol blended and subsequently irradiated UHMWPEs.

| α-Tocopherol Concentration | Radiation Dose | | | |
| --- | --- | --- | --- | --- |
|  | 65 kGy | 100 kGy | 150 kGy | 200 kGy |
| Virgin | 132 ± 25 | 175 ± 19 | 203 ± 14 | 220 ± 5 |
| 0.1 wt % | 119 ± 3 | 146 ± 4 | 166 ± 2 | 212 ± 13 |
| 0.3 wt % | 71 ± 2 | 93 ± 4 | 146 ± 5 | 144 ± 4 |
| 1.0 wt % | 61 ± 5 | 73 ± 4 | 75 ± 3 | 89 ± 6 |

The results showed that increased α-tocopherol concentration in UHMWPE prior to irradiation decreased the cross-linking of irradiated UHMWPE (see Table 9).

Example 38

High Pressure Crystallized, Irradiated, and Subsequently Melted UHMWPE

A block of approximately 2" in diameter and 2" in height was machined from GUR 1050 ram extruded stock and placed in a pressure chamber in water. The block was heated to 185° C. for 5 hours, and then isothermally pressurized to 45,000 psi. The pressure and temperature was held constant for 5 hours. At the completion of the pressurizing cycle, the samples were cooled to room temperature under pressure. Subsequently, the pressure was released.

A 1 cm-thick circular piece was machined from the high pressure crystallized UHMWPE. This piece was irradiated to 150 kGy by using electron beam irradiation in air as described in Example 1. Thin sections (3.2 mm) were machined from this piece and one of these thin sections was melted in vacuum at 170° C. It was kept two hours in the melt and cooled down to room temperature under vacuum.

The crystallinity of high pressure crystallized, irradiated and melted UHMWPE was determined as described in Example 11, and the tensile properties were determined by mechanical testing according to ASTM D-638.

The crystallinity of high pressure crystallized, 150-kGy irradiated and melted UHMWPE was 59±1%, the ultimate tensile strength was 36±0 MPa and the elongation at break was 223±26%.

Example 39

High Pressure Crystallized, Irradiated and Subsequently High Pressure Crystallized UHMWPE A block of approximately 2" in diameter and 3" in height is machined from GUR 1050 ram extruded stock and placed in a pressure chamber in water. The block is heated to 185° C. for 5 hours, and then isothermally pressurized to 45,000 psi. The pressure and temperature are held constant for 5 hours. At the completion of the pressurizing cycle, the samples are cooled to room temperature under pressure. Subsequently, the pressure is released.

A 1 cm-thick circular piece is machined from the high pressure crystallized UHMWPE. The piece is irradiated to 150 kGy by using electron beam irradiation in air as described in Example 1.

The irradiated piece is placed in a pressure chamber in water. The block is heated to 195° C. for 5 hours, and then isothermally pressurized to 55,000 psi. The pressure and temperature are held constant for 5 hours. At the completion of the pressurizing cycle, the samples are cooled to room temperature under pressure. Subsequently, the pressure is released.

Example 40

Cycles of High Pressure Crystallization and Subsequent Irradiation on UHMWPE

A block of approximately 2" in diameter and 3" in height is machined from GUR 1050 ram extruded stock and placed in a pressure chamber in water. The block is heated to 185° C. for 5 hours, and then isothermally pressurized to 45,000 psi. The pressure and temperature are held constant for 5 hours. At the completion of the pressurizing cycle, the samples are cooled to room temperature under pressure. Subsequently, the pressure is released.

A 1 cm-thick circular piece is machined from the high pressure crystallized UHMWPE. The piece is irradiated to 50 kGy by using electron beam irradiation in air as described in Example 1.

The 50 kGy irradiated piece is placed in a pressure chamber in water. The block is heated to 190° C. for 5 hours, and then isothermally pressurized to 50,000 psi. The pressure and temperature are held constant for 5 hours. At the completion of the pressurizing cycle, the samples are cooled to room temperature under pressure. Subsequently, the pressure is released.

This piece is irradiated to 50 kGy by using electron beam irradiation in air as described in Example 1 for a cumulative irradiation dose of 100 kGy.

This 100-kGy irradiated piece is placed in a pressure chamber in water. The block is heated to 190° C. for 5 hours, and then isothermally pressurized to 55,000 psi. The pressure and temperature are held constant for 5 hours. At the completion of the pressurizing cycle, the samples are cooled to room temperature under pressure. Subsequently, the pressure is released.

This piece is irradiated to 50 kGy by using electron beam irradiation in air as described in Example 1 for a cumulative irradiation dose of 150 kGy.

This 150-kGy irradiated piece is placed in a pressure chamber in water. The block is heated to 195° C. for 5 hours, and then isothermally pressurized to 60,000 psi. The pressure and temperature are held constant for 5 hours. At the completion of the pressurizing cycle, the samples are cooled to room temperature under pressure. Subsequently, the pressure is released.

The cross-link density, crystallinity and mechanical properties are determined after each irradiation and crystallization step.

Example 41

High Pressure Crystallization of Highly-Crosslinked UHMWPE

A block of approximately 2" in diameter and 3" in height was machined from GUR 1050 UHMWPE stock that has been compression molded, electron beam irradiated at 120° C. to 65 kGy and subsequently melted. The block was placed in a pressure chamber in water. The block was heated to 195° C. for 5 hours, and then isothermally pressurized to 52,000 psi. The pressure and temperature were held constant for 5 hours. At the completion of the pressurizing cycle, the sample was cooled to room temperature under pressure. Subsequently, the pressure was released.

Thin sections (3.2 mm thick) were machined from this high pressure crystallized highly cross-linked and melted UHMWPE. Mechanical testing was done on dog-bone shaped specimens in accordance with ASTM D-638. Crystallinity was measured as described in Example 11. The crystallinity was 63±1%, the ultimate tensile strength was 42±4 MPa and the elongation at break was 354±20%. Before high pressure crystallization, the crystallinity was 59±0% and the ultimate tensile strength was 35±2 MPa.

Example 42

High Pressure Crystallization of a Highly-Crosslinked Medical Device

A highly cross-linked medical device, such as a tibial knee insert or acetabular liner, machined from a ram extruded or thermally annealed GUR 1050 UHMWPE stock is placed in a pressure chamber in water. The liner is heated to 195° C. for 5 hours and then isothermally pressurized to 60,000 psi. The pressure and temperature are held constant for 5 hours. At the completion of the pressurizing cycle, the sample is cooled to room temperature under pressure. Subsequently, the pressure is released.

Example 43

High Pressure Crystallization of Irradiated and Doped UHMWPE by Heating Before Pressurizing (Route I)

A medical device, such as tibial knee insert or acetabular liner, is machined out of UHMWPE stock material. The device is irradiated to 65 or 100 kGy with electron beam or gamma irradiation in an inert environment. Subsequently, the device is doped with α-tocopherol. The device is then placed in a pressure chamber in water. The device is heated to 195° C. for 5 hours, and then isothermally pressurized to at least 45,000 psi, preferably 55,000 psi. The pressure and temperature are held constant for 5 hours. At the completion of the pressurizing cycle, the sample is cooled to room temperature under pressure. Subsequently, the pressure is released.

Example 44

High Pressure Crystallization of Irradiated and Doped UHMWPE by Pressurizing Before Heating (Route II)

A medical device, such as tibial knee insert or acetabular liner, is machined out of UHMWPE stock material. The device is irradiated to 65 or 100 kGy with electron beam or gamma irradiation in an inert environment. Subsequently, the device is doped with α-tocopherol. The device is then placed in a pressure chamber in water. The device is first pressurized to at least 45,000 psi, preferably 55,000 psi and subsequently heated to 195° C. for 5 hours. The pressure and temperature are held constant for 5 hours. At the completion of the pressurizing cycle, the sample is cooled to room temperature under pressure. Subsequently, the pressure is released.

Example 45

High Pressure Crystallization of Irradiated UHMWPE Containing Residual Free Radicals by Pressurizing Before Heating (Route II)

UHMWPE stock is annealed to reduce thermal stresses locked-in during the consolidation of the UHMWPE powder.

The annealing is carried out as follows: heat to 130° C. and hold for 5 hour; cool down to 125° C. at 1° C./hour and hold for 5 hours; cool down to 120° C. at 1° C./hour and hold for 5 hours; cool down to 115° C. at 1° C./hour and hold for 5 hours; cool down to 110° C. at 1° C./hour and hold for 5 hours; cool down to 105° C. at 1° C./hour and hold for 5 hours; cool down to 100° C. at 1° C./hour and hold for 5 hours; and cool down to room temperature at 1° C./hour.

A medical device, such as tibial knee insert or acetabular liner, is machined out of the annealed UHMWPE stock material. The device is irradiated to 65 or 100 kGy with electron beam or gamma irradiation in an inert environment. The device contains residual free radicals at this stage. Subsequently, the device is placed in a pressure chamber in water. The device is first pressurized to at least 45,000 psi, preferably to 55,000 psi, and subsequently heated to at least 180° C. or preferably to 195° C. for 5 hours. The pressure and temperature are held constant for at least 5 hours. At the completion of the pressurizing cycle, the sample is cooled to room temperature under pressure. Subsequently, the pressure is released. At the completion of the high pressure crystallization the device is expected to have no detectable residual free radicals and high crystallinity.

Example 46

High Pressure Crystallization of Irradiated UHMWPE Containing Residual Free Radicals by Heating Before Pressurizing (Route I)

UHMWPE stock is annealed to reduce thermal stresses locked-in during the consolidation of the UHMWPE powder. The annealing is carried out as follows: heat to 130° C. and hold for 5 hour; cool down to 125° C. at 1° C./hour and hold for 5 hours; cool down to 120° C. at 1° C./hour and hold for 5 hours; cool down to 115° C. at 1° C./hour and hold for 5 hours; cool down to 110° C. at 1° C./hour and hold for 5 hours; cool down to 105° C. at 1° C./hour and hold for 5 hours; cool down to 100° C. at 1° C./hour and hold for 5 hours; and cool down to room temperature at 1° C./hour.

A medical device, such as tibial knee insert or acetabular liner, is machined out of the annealed UHMWPE stock material. The device is irradiated to 65 or 100 kGy with electron beam or gamma irradiation in an inert environment. The device contains residual free radicals at this stage. Subsequently, the device is placed in a pressure chamber in water. The device is first heated to at least 180° C. or preferably to 195° C. for 5 hours, and subsequently pressurized to at least 45,000 psi, preferably to 55,000 psi. The pressure and temperature are held constant for at least 5 hours. At the completion of the pressurizing cycle, the sample is cooled to room temperature under pressure. Subsequently, the pressure is released. At the completion of the high pressure crystallization the device is expected to have no detectable residual free radicals and high crystallinity.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A method of making an oxidation resistant, cross-linked polymeric blend comprising:

a) mixing a polymeric material with one or more additives to form a polymeric blend in the absence of a supercritical fluid;
b) consolidating the polymeric blend;
c) irradiating the polymeric blend by ionizing radiation, thereby forming a cross-linked polymeric blend;
d) mechanically deforming the cross-linked polymeric blend below its melting point, thereby forming a mechanically deformed cross-linked polymeric blend; and
e) annealing the mechanically deformed cross-linked polymeric blend at a temperature that is above or below the melting point, thereby forming an oxidation resistant cross-linked polymeric blend.

2. The method of claim 1, wherein the polymeric material is a polyolefin, a polypropylene, a polyamide, a polyether ketone, or a mixture thereof.

3. The method of claim 2, wherein polyolefin is selected from a group consisting of a low-density polyethylene, high-density polyethylene, linear low-density polyethylene, ultra-high molecular weight polyethylene (UHMWPE), or a mixture thereof.

4. The method of claim 1, wherein the polymeric material is polymeric resin powder, polymeric flakes, polymeric particles, or a mixture thereof or an additive.

5. The method of claim 1, wherein the radiation dose is between about 25 and about 1000 kGy.

6. The method of claim 1, wherein the radiation dose is about 65 kGy, about 75 kGy, about 150 kGy or about 200 kGy.

7. The method of claim 1, wherein the radiation is a gamma irradiation.

8. The method of claim 1, wherein the radiation is an electron beam irradiation.

9. The method of claim 1 further comprising:

a) doping the cross-linked polymeric blend with an antioxidant by diffusion in the absence of a supercritical fluid, thereby forming an antioxidant-doped cross-linked polymeric blend; and
b) annealing the antioxidant-doped, cross-linked polymeric blend at a temperature below the melting point of the antioxidant-doped, cross-linked polymeric blend, thereby forming a cross-linked, oxidation resistant and homogenized polymeric blend.

10. The method of claim 1 further comprising:

a) machining the oxidation resistant cross-linked polymeric blend, thereby forming an oxidation resistant cross-linked medical implant;
b) doping the oxidation resistant cross-linked medical implant with an additive by diffusion in the absence of a supercritical fluid, thereby forming an additive-doped oxidation resistant cross-linked medical implant; and
c) annealing the additive-doped polymeric blend at a temperature below the melting point of the additive-doped polymeric blend, thereby forming a medical implant comprising an additive-doped and homogenized polymeric blend.

11. The method of claim 1, wherein the polymeric material is irradiated at a temperature between about room temperature and about the peak melting temperature of the polymeric blend.

12. The method of claim 1, wherein the polymeric blend is irradiated at a temperature above the peak melting point of the polymeric blend.

13. The method of claim 1, wherein at least one additive is an antioxidant.

14. A method of claim 1, wherein at least one additive is vitamin E.

15. The method in claim 1, wherein the additive concentration is about 0.01 wt/wt %, 0.02 wt/wt %, 0.05 wt/wt %, 0.1 wt/wt %, 0.2 wt/wt %, 0.5 wt/wt %, or 1.0 wt/wt %.

16. The method according to claim 1, wherein the polymeric blend contains more than one antioxidant.

17. The method of claim 1, wherein the cross-linked polymeric blend is mechanically deformed at a temperature below the melting point of the cross-linked polymeric blend.

18. The method of claim 1, wherein the annealing is carried out in air for at least for one minute to about 5 hours or more at about 130° C.

19. The method of claim 1, wherein the cross-linked polymeric blend is mechanically deformed uniaxially.

20. The method of claim 1, wherein the cross-linked polymeric blend is mechanically deformed to a compression ratio of about 2.5 at about 130° C.

21. The method of claim 1, wherein the cross-linked polymeric blend is heated to a temperature between above the room temperature and below the melt, and then mechanically deformed.

22. The method of claim 1, wherein the cross-linked polymeric blend is heated to a temperature of about 130° C., and then mechanically deformed.

23. The method of claim 1, wherein the polymeric blend is compression molded to a second material, and wherein the second material is a porous material.

24. The method of claim 1, wherein the polymeric blend is compression molded to a second material, and wherein the second material is metallic.

25. A method of making an oxidation resistant cross-linked blend of polymeric material comprising:
   a) blending the polymeric material with one or more additives in the absence of a supercritical fluid;
   b) consolidating the blend; and
   c) irradiating the blend of polymeric material with ionizing radiation at an elevated temperature that is above room temperature and below the melting point of the blend of polymeric material, thereby forming a cross-linked blend of polymeric material.

26. The method of claim 25, wherein at least one of the additives is an antioxidant.

27. The method of claim 25, wherein the polymeric material is a polyolefin, a polypropylene, a polyamide, a polyether ketone, or a mixture thereof.

28. The method of claim 27, wherein polyolefin is selected from a group consisting of a low-density polyethylene, high-density polyethylene, linear low-density polyethylene, ultra-high molecular weight polyethylene (UHMWPE), or a mixture thereof.

29. The method of claim 25, wherein the polymeric material is irradiated at a temperature between about room temperature and less than about 155° C.

30. The method of claim 25, wherein the blend of polymeric material is irradiated at a temperature of about 90° C.

31. The method of claim 25, wherein the blend of polymeric material is irradiated at a temperature of about 100° C.

32. The method of claim 25, wherein the blend of polymeric material is irradiated at a temperature of about 110° C.

33. The method of claim 25, wherein the blend of polymeric material is irradiated at a temperature of about 120° C.

34. The method of claim 25, wherein the blend of polymeric material is irradiated at a temperature of about 130° C.

35. The method of claim 25, wherein the blend of polymeric material is irradiated at a temperature of about 135° C.

36. The method of claim 25, wherein the irradiation dose is more than 1 kGy to 100 kGy, or more.

37. A method of making oxidation resistant cross-linked and interlocked hybrid material comprising:
   a) blending the polymeric material with one or more additives, thereby forming a polymeric blend in the absence of a supercritical fluid;
   b) compression molding the polymeric blend to the counterface of a second material, thereby forming an interlocked hybrid material having an interface between the polymeric blend and the second material; and
   c) irradiating the interlocked hybrid material with ionizing radiation at an elevated temperature that is above room temperature and below the melting point of the polymeric blend, thereby forming a cross-linked and interlocked hybrid material.

38. The method of claim 37, wherein the second material is a metallic mesh or back, a non-metallic mesh or back, a tibial tray, a patella tray, or an acetabular shell.

39. The method of claim 37, wherein the polymeric material is a polyolefin, a polypropylene, a polyamide, a polyether ketone, or a mixture thereof.

40. The method of claim 39, wherein polyolefin is selected from a group consisting of a low-density polyethylene, high-density polyethylene, linear low-density polyethylene, ultra-high molecular weight polyethylene (UHMWPE), or a mixture thereof.

41. The method of claim 37, wherein the interlocked hybrid material is irradiated at a temperature between about room temperature and less than about 155° C.

42. The method of claim 37, wherein the interlocked hybrid material is irradiated at a temperature of about 90° C.

43. The method of claim 37, wherein the interlocked hybrid material is irradiated at a temperature of about 100° C.

44. The method of claim 37, wherein the interlocked hybrid material is irradiated at a temperature of about 110° C.

45. The method of claim 37, wherein the interlocked hybrid material is irradiated at a temperature of about 120° C.

46. The method of claim 37, wherein the interlocked hybrid material is irradiated at a temperature of about 130° C.

47. The method of claim 37, wherein the interlocked hybrid material is irradiated at a temperature of about 135° C.

48. The method of claim 37, wherein the irradiation dose is more than 1 kGy to 100 kGy, or more.

49. The method of claim 37, wherein the second material is a porous.

50. The method of claim 37, wherein the second material is metallic.

* * * * *

UNITED STATES PATENT AND TRADEMARK OFFICE
CERTIFICATE OF CORRECTION

Page 1 of 1

PATENT NO.         : 8,426,486 B2
APPLICATION NO.    : 10/597652
DATED              : April 23, 2013
INVENTOR(S)        : Muratoga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this
Seventh Day of October, 2014

Michelle K. Lee
*Deputy Director of the United States Patent and Trademark Office*